United States Patent
Desbordes et al.

(10) Patent No.: US 10,626,109 B2
(45) Date of Patent: Apr. 21, 2020

(54) N-HETARYL(THIO)CARBONYL-2-(BENZOCYCLOALKEN-1-YL)CYCLAMINES AND THEIR USE AS FUNGICIDES

(71) Applicant: BAYER CROPSCIENCE AKTIENGESELLSCHAFT, Monheim am Rhein (DE)

(72) Inventors: Philippe Desbordes, Lyons (FR); Philippe Rinolfi, Chatillon d'Azergues (FR); Tomoki Tsuchiya, Lyons (FR)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 532 days.

(21) Appl. No.: 15/028,004

(22) PCT Filed: Oct. 7, 2014

(86) PCT No.: PCT/EP2014/071397
§ 371 (c)(1),
(2) Date: Apr. 7, 2016

(87) PCT Pub. No.: WO2015/052160
PCT Pub. Date: Apr. 16, 2015

(65) Prior Publication Data
US 2016/0244433 A1 Aug. 25, 2016

(30) Foreign Application Priority Data
Oct. 8, 2013 (EP) ..................... 13356013

(51) Int. Cl.
| | | |
|---|---|---|
| *C07D 403/06* | (2006.01) | |
| *A01N 43/36* | (2006.01) | |
| *C07D 405/14* | (2006.01) | |
| *C07D 401/06* | (2006.01) | |
| *C07D 405/06* | (2006.01) | |
| *C07D 409/06* | (2006.01) | |
| *C07D 417/06* | (2006.01) | |
| *C07D 211/12* | (2006.01) | |
| *C07D 207/06* | (2006.01) | |
| *C07D 405/04* | (2006.01) | |
| *A01N 43/56* | (2006.01) | |
| *A01N 43/647* | (2006.01) | |
| *A01N 43/78* | (2006.01) | |
| *A01N 61/00* | (2006.01) | |

(52) U.S. Cl.
CPC ........... *C07D 403/06* (2013.01); *A01N 43/36* (2013.01); *A01N 43/56* (2013.01); *A01N 43/647* (2013.01); *A01N 43/78* (2013.01); *A01N 61/00* (2013.01); *C07D 207/06* (2013.01); *C07D 211/12* (2013.01); *C07D 401/06* (2013.01); *C07D 405/04* (2013.01); *C07D 405/06* (2013.01); *C07D 405/14* (2013.01); *C07D 409/06* (2013.01); *C07D 417/06* (2013.01)

(58) Field of Classification Search
None
See application file for complete search history.

(56) References Cited

U.S. PATENT DOCUMENTS

| 4,994,486 A | 2/1991 | Schoenleber et al. ........ 514/456 |
|---|---|---|
| 2011/0207781 A1 | 8/2011 | Stierli et al. .................. 514/343 |
| 2011/0294863 A1 | 12/2011 | Benting et al. ............... 514/406 |
| 2013/0102790 A1 | 4/2013 | Benting et al. ............. 548/364.4 |
| 2013/0131119 A1 | 5/2013 | Benting et al. ............... 514/341 |
| 2013/0217727 A1 | 8/2013 | Benting et al. ............... 514/314 |
| 2013/0261155 A1 | 10/2013 | Benting et al. ............... 514/326 |

FOREIGN PATENT DOCUMENTS

| CN | 103313977 A | 9/2013 |
|---|---|---|
| EP | 0325963 A1 | 8/1989 |
| WO | WO 89/06645 A1 | 7/1989 |
| WO | WO 96/38435 | 12/1996 |
| WO | WO 2009/153191 | 12/2009 |
| WO | WO 2010/086311 A1 | 8/2010 |
| WO | WO 2011/151369 A1 | 12/2011 |
| WO | WO 2012/052489 A1 | 4/2012 |

(Continued)

OTHER PUBLICATIONS

International Search Report dated Nov. 27, 2014 in corresponding International Application No. PCT/EP2014/071397.
Murat Kizil et al.: "Tandam Radical Cyclizations on Iodoaryl Azides: Synthesis of the Core Tetracycle of *Aspidosperma* Alkaloids", The Journal of Organic Chemistry, vol. 64, No. 21, Oct. 15, 1999, pp. 7856-7862, XP055149548, ISSN: 0022-3263.
Database Registry [Online] Chemical Abstracts Service, Columbus, OH, US; Dec. 5, 2011, XP002731800, Databases accession No. 1349136-05-5, abstract.
Database Registry [Online] Chemical Abstracts Service, Columbus, Ohio, US; Dec. 4, 2011, XP002731801, Database accession No. 1348350-15-1, abstract.

(Continued)

*Primary Examiner* — Hasan S Ahmed
*Assistant Examiner* — Frank Choi
(74) *Attorney, Agent, or Firm* — Morrison & Foerster LLP

(57) ABSTRACT

The present invention relates to fungicidal N-hetarylcarbonyl-2-(benzocycloalken-1-yl)piperidines or pyrrolidines of formula (I), and their thiocarbonyl derivatives, wherein A represents a carbo-linked, unsaturated or partially saturated, 5-membered heterocyclyl group that can be substituted by up to four groups R that can be the same or different; T represents 0 or S; n represents 1 or 2; m represents 1, 2 or 3; p represents 1, 2, 3 or 4, $L^1$ and $L^2$ independently represent $CZ^4Z^5$, $NZ^6$, 0, S, S(O) or $S(0)_2$; and R and $Z^1$-$Z^6$ are as defined in the claims; their process of preparation and intermediate compounds for their preparation, their use as fungicides, particularly in the form of fungicidal compositions and methods for the control of phytopathogenic fungi of plants using these compounds or their compositions.

21 Claims, No Drawings

(56) References Cited

FOREIGN PATENT DOCUMENTS

| WO | WO 2012/052491 A1 | 4/2012 |
| WO | WO-2012052489 A1 | 4/2012 |

OTHER PUBLICATIONS

Database Registry [Online] Chemical Abstracts Service, Columbus, Ohio, US; Nov. 9, 2011, XP002731802, Database accession No. 1342896-20-1, abstract.
Database Registry [Online] Chemical Abstracts Service, Columbus, Ohio, US; Nov. 3, 2010, Database accession No. 1251007-56-3, abstract.
Database Registry [Online] Chemical Abstracts Service, Columbus, Ohio, US; Dec. 29, 2004, XP002731804, Database accession No. 803650-32-0, abstract.
Database Registry [Online] Chemical Abstracts Service, Columbus, Ohio, US; Feb. 4, 2014, XP002731805, Database accession No. 1536740-28-9, abstract.

N-HETARYL(THIO)CARBONYL-2-(BENZOCYCLOALKEN-1-YL)CYCLAMINES AND THEIR USE AS FUNGICIDES

CROSS-REFERENCE TO RELATED APPLICATION(S)

The present application is a 35 U.S.C. § 371 national phase conversion of PCT/EP2014/071397 filed on Oct. 7, 2014, which claims priority of European Application No. 13356013.6 filed on Oct. 8, 2013. Applicants claim priority to each of the foregoing patent applications. The PCT International Application was published in the English language.

FIELD OF THE INVENTION

The present invention relates to fungicidal N-hetarylcarbonyl-2-(benzocycloalken-1-yl)piperidines or pyrrolidines, and their thiocarbonyl derivatives, their process of preparation and intermediate compounds for their preparation, their use as fungicides, particularly in the form of fungicidal compositions and methods for the control of phytopathogenic fungi of plants using these compounds or their compositions.

BACKGROUND OF THE INVENTION

In international patent application WO-2009/153191 certain fungicidal proline amides are generically embraced in a broad disclosure of numerous compounds of the following formula:

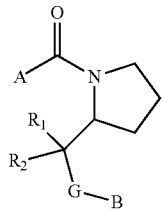

wherein A can represent a substituted pyrazole or a substituted pyridine, $R_1$ and $R_2$ can represent various substituents among which a hydrogen atom or a $C_1$-$C_8$-alkyl group, G can represent a bond, an oxygen atom, a sulfur atom, a $CH_2$ or a $(CH_2)_2$ moiety, and B can represent a (un)substituted phenyl ring. However, there is no explicit disclosure or suggestion to select in this document of any such derivative wherein G can represent a bond and $R_1$ be cyclized together with the B ring.

In international patent application WO-2012/052489 certain fungicidal piperidines are generically embraced in a broad disclosure of numerous compounds of the following formula:

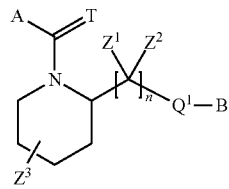

wherein A can represent a carbo-linked, partially saturated or unsaturated, 5-membered heterocyclyl group, T can represent an oxygen or a sulfur atom, n can represent 0, 1 or 2, $Z^1$ and $Z^2$ can represent various substituents among which a hydrogen atom or a $C_1$-$C_8$-alkyl group, $Q^1$ can represent a bond, an oxygen atom, an oxidized or unoxidized sulfur atom and B can represent various rings among which a phenyl ring. However, there is no explicit disclosure or suggestion to select in this document of any such derivative wherein n can represent 1, $Q^1$ can represent a bond and $Z^1$ be cyclized together with the B ring.

In international patent application WO-2012/052491 certain fungicidal pyrrolidines are generically embraced in a broad disclosure of numerous compounds of the following formula:

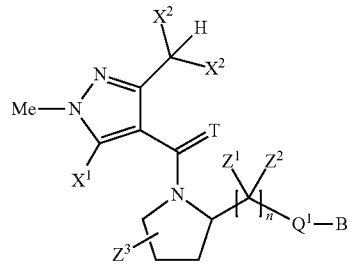

wherein $X^1$ and $X^2$ can represent a halogen atom, T can represent an oxygen or a sulfur atom, n can represent 0, 1 or 2, $Z^1$ and $Z^2$ can represent various substituents among which a hydrogen atom or a $C_1$-$C_6$-alkyl group, $Q^1$ can represent a bond, an oxygen atom, an oxidized or unoxidized sulfur atom and B can represent various rings among which a phenyl ring. However, there is no explicit disclosure or suggestion to select in this document of any such derivative wherein n can represent 1, $Q^1$ can represent a bond and $Z^1$ be cyclized together with the B ring.

In international patent application WO-2010/086311 certain fungicidal N-cycloalkyl-N-bicyclicmethylene(thio)carboxamides are generically embraced in a broad disclosure of numerous compounds of the following formula:

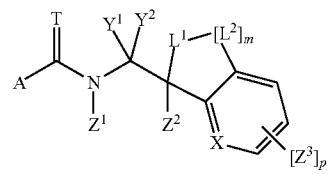

wherein A can represent a carbo-linked, partially saturated or unsaturated, 5-membered heterocyclyl group, T can represent an oxygen or a sulfur atom, $Z^1$ can represent a non substituted or substituted $C_3$-$C_7$-cycloalkyl and $Y^1$ or $Y^2$ can represent an alkyl group. However, there is no explicit disclosure or suggestion to select in this document of any such derivative wherein $Z^1$ and $Y^1$ or $Y^2$ are cyclized to form a 5- or 6-membered heterocyclic ring.

In international patent application WO-2011/151369 certain fungicidal N-[(het)arylethyl)]pyrazole(thio)carboxamides are generically embraced in a broad disclosure of numerous compounds of the following formula:

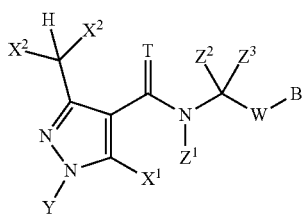

wherein $X^1$ and $X^2$ can represent a halogen atom, T can represent an oxygen or a sulfur atom, $Z^1$ can represent a non substituted or substituted $C_3$-$C_7$-cycloalkyl, $Z^2$ or $Z^3$ can represent an alkyl group, W can represent a $CZ^4Z^5$ group wherein $Z^4$ or $Z^5$ can represent an alkyl group, and B can represent a phenyl ring. However, there is no explicit disclosure or suggestion to select in this document of any such derivative wherein $Z^1$ and $Z^2$ or $Z^3$ and, B and $CZ^4Z^5$ are both cyclized to form a 5- or 6-membered heterocyclic ring substituted by a benzo-fused 5- to 7-membered hetero- or carbo-cycle.

SUMMARY OF THE INVENTION

It is always of high interest in the field of agrochemicals to use pesticidal compounds more active than the compounds already known by the man ordinary skilled in the art whereby reduced amounts of compound can be used whilst retaining equivalent efficacy.

Furthermore, the provision of new pesticidal compounds with a higher efficacy strongly reduces the risk of appearance of resistant strains in the fungi to be treated.

We have now found a new family of compounds which show enhanced fungicidal activity over the general known family of such compounds.

Accordingly, the present invention provides a N-hetaryl (thio)carbonyl-2-(benzocycloalken-1-yl)piperidine or pyrrolidine derivative of formula (I)

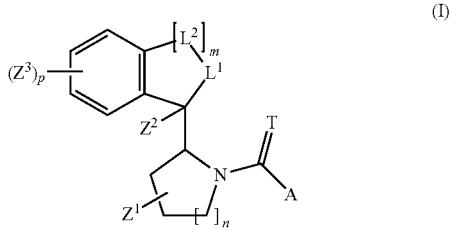

wherein
A represents a carbo-linked, unsaturated or partially saturated, 5-membered heterocyclyl group that can be substituted by up to four groups R that can be the same or different;
T represents O or S;
n represents 1 or 2;
m represents 1, 2 or 3;
p represents 1, 2, 3 or 4,
$L^1$ and $L^2$ independently represent $CZ^4Z^5$, $NZ^6$, O, S, S(O) or $S(O)_2$,
$Z^1$ represents a hydrogen atom; or substituted or non-substituted $C_1$-$C_8$-alkyl,
$Z^2$ represents a hydrogen atom, a halogen atom, hydroxyl group, cyano, substituted or non-substituted $C_1$-$C_8$-alkyl, substituted or non-substituted $C_1$-$C_8$-alkoxy, $C_1$-$C_8$-halogenoalkyl comprising up to 9 halogen atoms that can be the same or different, amino or $C_1$-$C_8$-alkylamino,
$Z^3$ represents a hydrogen atom, a halogen atom, nitro, cyano; isonitrile; hydroxy; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-halogenoalkyl having 1 to 9 halogen atoms; substituted or non-substituted $C_2$-$C_8$-alkenyl; $C_2$-$C_8$-halogenoalkenyl having 1 to 9 halogen atoms; substituted or non-substituted $C_2$-$C_8$-alkynyl; $C_2$-$C_8$-halogenoalkynyl having 1 to 9 halogen atoms; substituted or non-substituted $C_1$-$C_8$-alkoxy; $C_1$-$C_8$-halogenoalkoxy having 1 to 9 halogen atoms; substituted or non-substituted $C_1$-$C_8$-alkylsulfanyl; $C_1$-$C_8$-halogenoalkylsulfanyl having 1 to 9 halogen atoms; substituted or non-substituted $C_1$-$C_8$-alkylsulfinyl; $C_1$-$C_8$-halogenoalkylsulfinyl having 1 to 9 halogen atoms; substituted or non-substituted $C_1$-$C_8$-alkylsulfonyl; $C_1$-$C_8$-halogenoalkylsulfonyl having 1 to 9 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-halogenoalkenyloxy having 1 to 9 halogen atoms; substituted or non-substituted $C_3$-$C_8$-alkynyloxy; $C_2$-$C_8$-halogenoalkynyloxy having 1 to 9 halogen atoms; substituted or non-substituted $C_3$-$C_7$-cycloalkyl; $C_3$-$C_7$-halogenocycloalkyl having 1 to 9 halogen atoms; substituted or non-substituted $C_4$-$C_7$-cycloalkenyl; $C_4$-$C_7$-halogenocycloalkenyl having 1 to 9 halogen atoms; substituted or non-substituted ($C_3$-$C_7$-cycloalkyl)-$C_1$-$C_8$-alkyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri($C_1$-$C_8$)alkylsilyl; substituted or non-substituted tri ($C_1$-$C_8$)alkylsilyl-$C_1$-$C_8$-alkyl; substituted or non-substituted $C_1$-$C_8$-alkylcarbonyl; $C_1$-$C_8$-halogenoalkylcarbonyl having 1 to 9 halogen atoms; substituted or non-substituted $C_1$-$C_8$-alkylcarbonyloxy; $C_1$-$C_8$-halogenoalkylcarbonyloxy having 1 to 9 halogen atoms; substituted or non-substituted $C_1$-$C_8$-alkylcarbonylamino; $C_1$-$C_8$-halogenoalkylcarbonylamino having 1 to 9 halogen atoms; substituted or non-substituted $C_1$-$C_8$-alkoxycarbonyl; $C_1$-$C_8$-halogenoalkoxycarbonyl having 1 to 9 halogen atoms; substituted or non-substituted $C_1$-$C_8$-alkyloxycarbonyloxy; $C_1$-$C_8$-halogenoalkoxycarbonyloxy having 1 to 9 halogen atoms; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl that can be substituted by up to 6 groups Q which can be the same or different; aryl-$C_1$-$C_8$-alkyl that can be substituted by up to 6 groups Q which can be the same or different; aryl-$C_2$-$C_8$-alkenyl that can be substituted by up to 6 groups Q which can be the same or different; aryl-$C_2$-$C_8$-alkynyl that can be substituted by up to 6 groups Q which can be the same or different; aryloxy that can be substituted by up to 6 groups Q which can be the same or different; arylsulfanyl that can be substituted by up to 6 groups Q which can be the same or different; or arylamino that can be substituted by up to 6 groups Q which can be the same or different; aryl-$C_1$-$C_8$-alkyloxy that can be substituted by up to 6 groups Q which can be the same or different; aryl-$C_1$-$C_8$-alkylsulfanyl that can be substituted by up to 6 groups Q which can be the same or different; aryl-$C_1$-$C_8$-alkylamino that can be substituted by up to 6 groups Q which can be the same or different; pyridinyl which can be substituted by up to 4 groups Q; pyridinyloxy which can be substituted by up to 4 groups Q, $Z^4$ and $Z^5$ independently represents a hydrogen atom, a halogen atom, cyano, nitro, substituted or non-substituted $C_1$-$C_8$-alkyl, $C_1$-$C_8$-halogenoalkyl comprising up to 9 halogen atoms that can be the same or different, substituted or non-substituted $C_1$-$C_8$-alkoxy, $C_1$-$C_8$-halogenoalkoxy comprising up to 9 halogen atoms that can be the same or different, substituted or non-substituted $C_1$-$C_8$-alkoxy-$C_1$-$C_8$-alkyl, substituted or non-substituted $C_2$-$C_8$-alkenyl, $C_2$-$C_8$-halogenoalkenyl comprising up to 9 halogen atoms that can be the same or different, substituted or non-substituted $C_2$-$C_8$-alkynyl, $C_2$-$C_8$-halogenoalkynyl comprising up to 9 halogen atoms that can be the same or different, substituted or non-substituted $C_3$-$C_7$-cycloalkyl, substituted or non-substituted $C_3$-$C_7$-cycloalkyl-$C_1$-$C_8$-alkyl, $C_3$-$C_7$-halogenocycloalkyl comprising up to 9 halogen atoms that can be the same or different, formyl, substituted or non-substituted $C_1$-$C_8$-alkylcarbonyl, $C_1$-$C_8$-halogenoalkylcarbonyl comprising up to 9 halogen atoms that can be the same or different, substituted or non-substituted $C_1$-$C_8$-alkylsulfanyl, $C_1$-$C_8$-halogenoalkylsulfanyl comprising up to 9 halogen atoms that can be the same or different, substituted or non-substituted $C_1$-$C_8$-alkylsulfinyl, $C_1$-$C_8$-halogenoalkylsulfinyl comprising up to 9 halogen atoms that can be the same or different, substituted or non-substituted $C_1$-$C_8$-alkylsulfonyl, or $C_1$-$C_8$-halogenoalkylsulfonyl comprising up to 9 halogen atoms that can be the same or different, $Z^6$ represents a hydrogen atom, substituted or non-substituted $C_1$-$C_8$-alkyl, $C_1$-$C_8$-halogenoalkyl comprising up to 9 halogen atoms that can be the same or different, substituted or non-substituted $C_1$-$C_8$-alkoxy-$C_1$-$C_8$-alkyl, substituted or non-substituted $C_2$-$C_8$-alkenyl, $C_2$-$C_8$-halogenoalkenyl comprising up to 9 halogen atoms that can be the same or different, substituted or non-substituted $C_2$-$C_8$-alkynyl, $C_3$-$C_8$-halogenoalkynyl comprising up to 9 halogen atoms that can be the same or different, substituted or non-substituted $C_3$-$C_7$-cycloalkyl, substituted or non-substituted $C_3$-$C_7$-cycloalkyl-$C_1$-$C_8$-alkyl, $C_3$-$C_7$-halogenocycloalkyl comprising up to 9 halogen atoms that can be the same or different, formyl, substituted or non-substituted $C_1$-$C_8$-alkylcarbonyl, $C_1$-$C_8$-halogenoalkylcarbonyl comprising up to 9 halogen atoms that can be the same or different, substituted or non-substituted $C_1$-$C_8$-alkoxycarbonyl, substituted or non-substituted $C_1$-$C_8$-alkylsulfonyl, $C_1$-$C_8$-halogenoalkylsulfonyl comprising up to 9 halogen atoms that can be the same or different, phenylsulfonyl can be substituted by up to 5 groups Q that can be the same or different, or benzyl that can be substituted by up to 5 groups Q that can be the same or different, Q independently represents a halogen atom, cyano, nitro, substituted or non-substituted $C_1$-$C_8$-alkyl, $C_1$-$C_8$-halogenoalkyl comprising up to 9 halogen atoms that can be the same or different, substituted or non-substituted $C_1$-$C_8$-alkoxy, $C_1$-$C_8$-halogenoalkoxy comprising up to 9 halogen atoms that can be the same or different, substituted or non-substituted $C_1$-$C_8$-alkylsulfanyl, $C_1$-$C_8$-halogenoalkylsulfanyl comprising up to 9 halogen atoms that can be the same or different, substituted or non-substituted tri($C_1$-$C_8$)alkylsilyl, substituted or non-substituted tri($C_1$-$C_8$)alkylsilyl-$C_1$-$C_8$-alkyl, substituted or non-substituted ($C_1$-$C_8$-alkoxyimino)-$C_1$-$C_8$-alkyl, or substituted or non-substituted (benzyloxyimino)-$C_1$-$C_8$-alkyl, R independently represents hydrogen atom; halogen atom; nitro; cyano; hydroxy; amino; sulfanyl; pentafluoro-$\lambda^6$-sulfanyl; substituted or non-substituted ($C_1$-$C_8$-alkoxyimino)-$C_1$-$C_8$-alkyl; substituted or non-substituted (benzyloxyimino)-$C_1$-$C_8$-alkyl; substituted or non-substituted $C_1$-$C_8$-alkyl; $C_1$-$C_8$-halogenoalkyl having 1 to 9 halogen atoms; substituted or non-substituted $C_2$-$C_8$-alkenyl; $C_2$-$C_8$-halogenoalkenyl having 1 to 9 halogen atoms; substituted or non-substituted $C_2$-$C_8$-alkynyl; $C_2$-$C_8$-halogenoalkynyl having 1 to 9 halogen atoms; substituted or non-substituted $C_1$-$C_8$-alkoxy; $C_1$-$C_8$-halogenoalkoxy having 1 to 9 halogen atoms; substituted or non-substituted $C_1$-$C_8$-alkylsulfanyl; $C_1$-$C_8$-halogenoalkylsulfanyl having 1 to 9 halogen atoms; substituted or non-substituted $C_1$-$C_8$-alkylsulfinyl; $C_1$-$C_8$-halogenoalkylsulfinyl having 1 to 9 halogen atoms; substituted or non-substituted $C_1$-$C_8$-alkylsulfonyl; $C_1$-$C_8$-halogenoalkylsulfonyl having 1 to 9 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; substituted or non-substituted $C_3$-$C_8$-alkynyloxy; substituted or non-substituted $C_3$-$C_7$-cycloalkyl; $C_3$-$C_7$-halogenocycloalkyl having 1 to 9 halogen atoms; substituted or non-substituted tri($C_1$-$C_8$)alkylsilyl; substituted or non-substituted $C_1$-$C_8$-alkylcarbonyl; $C_1$-$C_8$-halogenoalkylcarbonyl having 1 to 9 halogen atoms; substituted or non-substituted $C_1$-$C_8$-alkoxycarbonyl; $C_1$-$C_8$-halogenoalkoxycarbonyl having 1 to 9 halogen atoms; substituted or non-substituted $C_1$-$C_8$-alkylcarbamoyl; substituted or non-substituted di-$C_1$-$C_8$-alkylcarbamoyl; phenoxy; phenylsulfanyl; phenylamino; benzyloxy; benzylsulfanyl; or benzylamino;

as well as salts, N-oxides, metal complexes, metalloid complexes and optically active or geometric isomers thereof.

DETAILED DESCRIPTION OF THE INVENTION

Unless indicated otherwise, a group or a substituent that is substituted according to the invention can be substituted by one or more of the following groups or atoms: a halogen atom; nitro; hydroxyl; cyano; isonitrile; amino; sulfanyl; a pentafluoro-$\lambda^6$-sulfanyl group; formyl; formyloxy; formylamino; carbamoyl; N-hydroxycarbamoyl; carbamate; (hydroxyimino)-$C_1$-$C_8$-alkyl; $C_1$-$C_8$-alkyl; a tri($C_1$-$C_8$-alkyl)silyl; $C_3$-$C_8$-cycloalkyl; $C_1$-$C_8$-halogenoalkyl having 1 to 5 halogen atoms; a $C_3$-$C_8$-halogenocycloalkyl having 1 to 5 halogen atoms; $C_2$-$C_8$-alkenyl; $C_2$-$C_8$-alkynyl; $C_2$-$C_8$-alkenyloxy; $C_2$-$C_8$-alkynyloxy; $C_1$-$C_8$-alkylamino; di-$C_1$-

$C_8$-alkylamino; $C_1$-$C_8$-alkoxy; $C_1$-$C_8$-halogenoalkoxy having 1 to 5 halogen atoms; $C_1$-$C_8$-alkylsulfanyl; $C_1$-$C_8$-halogenoalkylsulfanyl having 1 to 5 halogen atoms; $C_2$-$C_8$-alkenyloxy; $C_2$-$C_8$-halogenoalkenyloxy having 1 to 5 halogen atoms; $C_3$-$C_8$-alkynyloxy; $C_3$-$C_8$-halogenoalkynyloxy having 1 to 5 halogen atoms; $C_1$-$C_8$-alkylcarbonyl; $C_1$-$C_8$-halogenoalkylcarbonyl having 1 to 5 halogen atoms; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl having 1 to 5 halogen atoms; $C_1$-$C_8$-alkylcarbonyloxy; $C_1$-$C_8$-halogenoalkylcarbonyloxy having 1 to 5 halogen atoms; $C_1$-$C_8$-alkylcarbonylamino; $C_1$-$C_8$-halogenoalkylcarbonylamino having 1 to 5 halogen atoms; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfanyl; $C_1$-$C_8$-halogenoalkylsulfanyl having 1 to 5 halogen atoms; $C_1$-$C_8$-alkylsulfinyl; $C_1$-$C_8$-halogenoalkylsulfinyl having 1 to 5 halogen atoms; $C_1$-$C_8$-alkylsulfonyl; $C_1$-$C_8$-halogenoalkylsulfonyl having 1 to 5 halogen atoms; $C_1$-$C_8$-alkylaminosulfamoyl; di-$C_1$-$C_8$-alkylaminosulfamoyl; ($C_1$-$C_6$-alkoxyimino)-$C_1$-$C_6$-alkyl; ($C_1$-$C_6$-alkenyloxyimino)-$C_1$-$C_8$-alkyl; ($C_1$-$C_6$-alkynyloxyimino)-$C_1$-$C_8$-alkyl; 2-oxopyrrolidin-1-yl; (benzyloxyimino)-$C_1$-$C_8$-alkyl; $C_1$-$C_8$-alkoxyalkyl; $C_1$-$C_8$-halogenoalkoxyalkyl having 1 to 5 halogen atoms; benzyloxy; benzylsulfanyl; benzylamino; aryloxy; arylsulfanyl or arylamino.

For the compounds according to the invention, the following generic terms are generally used with the following meanings:
halogen means fluorine, bromine, chlorine or iodine.
carboxy means —C(=O)OH;
carbonyl means —C(=O)—;
carbamoyl means —C(=O)NH$_2$;
N-hydroxycarbamoyl means —C(=O)NHOH;
SO represents a sulfoxide group;
SO$_2$ represents a sulfone group;
methylene means the diradical —CH$_2$—;
an alkyl group, an alkenyl group and an alkynyl group as well as moieties containing these terms, can be linear or branched;
heteroatom means sulfur, nitrogen or oxygen.
halogenated groups, notably haloalkyl, haloalkoxy and halocycloalkyl groups, can comprise up to nine identical or different halogen atoms;
the term "aryl" means phenyl or naphthyl;
in the case of an amino group or the amino moiety of any other amino-comprising group, substituted by two substituent that can be the same or different, the two substituent together with the nitrogen atom to which they are linked can form a heterocyclyl group, preferably a 5- to 7-membered heterocyclyl group, that can be substituted or that can include other hetero atoms, for example a morpholino group or piperidinyl group.

Any of the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions) and to the mixtures of all the possible stereoisomers, in all proportions. The diastereoisomers and/or the optical isomers can be separated according to the methods which are known per se by the man ordinary skilled in the art.

Any of the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compounds of the present invention can also exist in one or more geometric isomer forms depending on the relative position (syn/anti or cis/trans or endo/exo) of the substituents of any chain or ring. The invention thus relates equally to all syn/anti (or cis/trans or endo/exo) isomers and to all possible syn/anti (or cis/trans or endo/exo) mixtures, in all proportions. The syn/anti (or cis/trans or endo/exo) isomers can be separated according to general methods, which are known per se by the man ordinary skilled in the art.

Preferred compounds according to the invention are compounds of formula (I) wherein A is selected in the list consisting of:
a heterocycle of formula (A$^1$)

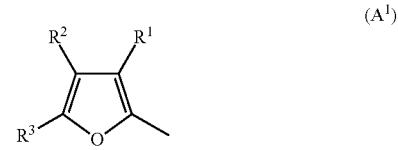

wherein:
R$^1$ to R$^3$ that can be the same or different represent a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or $C_1$-$C_5$-halogenoalkoxy comprising up to 9 halogen atoms that can be the same or different;
a heterocycle of formula (A$^2$)

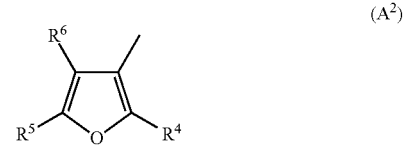

wherein:
R$^4$ to R$^6$ that can be the same or different represent a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or $C_1$-$C_5$-halogenoalkoxy comprising up to 9 halogen atoms that can be the same or different;
a heterocycle of formula (A$^3$)

wherein:

$R^7$ represents a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or $C_1$-$C_5$-halogenoalkoxy comprising up to 9 halogen atoms that can be the same or different;

$R^8$ represents a hydrogen atom or a substituted or non-substituted $C_1$-$C_5$-alkyl;

a heterocycle of formula ($A^4$)

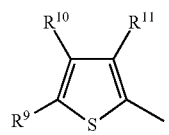

($A^4$)

wherein:

$R^9$ to $R^{11}$ that can be the same or different represent a hydrogen atom; a halogen atom; substituted or non-substituted $C_1$-$C_5$-alkyl; amino; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different or $C_1$-$C_5$-halogenoalkoxy comprising up to 9 halogen atoms that can be the same or different;

a heterocycle of formula ($A^5$)

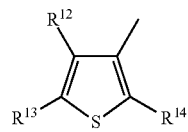

($A^5$)

wherein:

$R^{12}$ and $R^{13}$ that can be the same or different represent a hydrogen atom; a halogen atom; substituted or non-substituted $C_1$-$C_5$-alkyl; substituted or non-substituted $C_1$-$C_5$-alkoxy; amino; $C_1$-$C_5$-halogenoalkyl comprising up to 9 halogen atoms that can be the same or different or $C_1$-$C_5$-halogenoalkoxy comprising up to 9 halogen atoms that can be the same or different;

$R^{14}$ represents a hydrogen atom; a halogen atom; substituted or non-substituted $C_1$-$C_5$-alkyl; substituted or non-substituted $C_1$-$C_5$-alkoxy; amino; $C_1$-$C_5$-halogenoalkyl comprising up to 9 halogen atoms that can be the same or different or $C_1$-$C_5$-halogenoalkoxy comprising up to 9 halogen atoms that can be the same or different;

a heterocycle of formula ($A^6$)

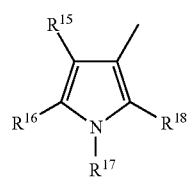

($A^6$)

wherein:

$R^{15}$ represents a hydrogen atom; a halogen atom; a cyano; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{16}$ and $R^{18}$ that can be the same or different represent a hydrogen atom; a halogen atom; substituted or non-substituted $C_1$-$C_5$-alkoxycarbonyl; substituted or non-substituted $C_1$-$C_5$-alkyl; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{17}$ represent a hydrogen atom or substituted or non-substituted $C_1$-$C_5$-alkyl;

a heterocycle of formula ($A^7$)

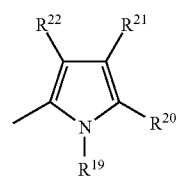

($A^7$)

wherein:

$R^{19}$ represents a hydrogen atom or a $C_1$-$C_5$-alkyl $R^{20}$ to $R^{22}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;

a heterocycle of formula ($A^8$)

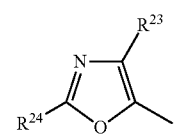

($A^8$)

wherein:

$R^{23}$ represents a hydrogen atom; a halogen atom; substituted or non-substituted $C_1$-$C_5$-alkyl or $C_1$-$C_5$-halogenoalkyl comprising up to 9 halogen atoms that can be the same or different;

$R^{24}$ represents a hydrogen atom or substituted or non-substituted $C_1$-$C_5$-alkyl or $C_1$-$C_5$-halogenoalkyl comprising up to 9 halogen atoms that can be the same or different;

a heterocycle of formula ($A^9$)

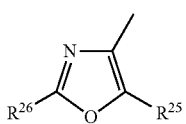

($A^9$)

wherein:

$R^{25}$ represents a hydrogen atom; a halogen atom; substituted or non-substituted $C_1$-$C_5$-alkyl or $C_1$-$C_5$-halogenoalkyl comprising up to 9 halogen atoms that can be the same or different;

$R^{26}$ represents a hydrogen atom; substituted or non-substituted $C_1$-$C_5$-alkyl or $C_1$-$C_5$-halogenoalkyl comprising up to 9 halogen atoms that can be the same or different;

a heterocycle of formula ($A^{10}$)

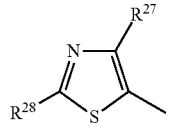

($A^{10}$)

wherein:

$R^{27}$ represents a hydrogen atom; a halogen atom; substituted or non-substituted $C_1$-$C_5$-alkyl or $C_1$-$C_5$-halogenoalkyl comprising up to 9 halogen atoms that can be the same or different;

$R^{28}$ represents a hydrogen atom; a halogen atom; substituted or non-substituted $C_1$-$C_5$-alkyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or substituted or non-substituted di($C_1$-$C_5$-alkyl)amino;

a heterocycle of formula ($A^{11}$)

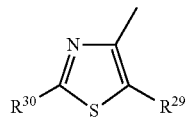

($A^{11}$)

wherein:

$R^{29}$ represents a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{30}$ represents a hydrogen atom; a halogen atom; substituted or non-substituted $C_1$-$C_5$-alkyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or substituted or non-substituted di($C_1$-$C_5$-alkyl)amino;

a heterocycle of formula ($A^{12}$)

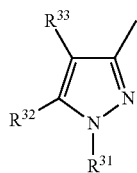

($A^{12}$)

wherein:

$R^{31}$ represents a hydrogen atom or a substituted or non-substituted $C_1$-$C_5$-alkyl $R^{32}$ represents a hydrogen atom; a halogen atom; substituted or non-substituted $C_1$-$C_5$-alkyl or $C_1$-$C_5$-halogenoalkyl comprising up to 9 halogen atoms that can be the same or different;

$R^{33}$ represents a hydrogen atom; a halogen atom; a nitro; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

a heterocycle of formula ($A^{13}$)

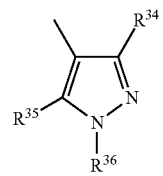

($A^{13}$)

wherein:

$R^{34}$ represents a hydrogen atom; a halogen atom; substituted or non-substituted $C_1$-$C_5$-alkyl; substituted or non-substituted $C_3$-$C_5$-cycloalkyl; $C_1$-$C_5$-halogenoalkyl comprising up to 9 halogen atoms that can be the same or different; substituted or non-substituted $C_1$-$C_5$-alkoxy; substituted or non-substituted $C_2$-$C_5$-alkynyloxy or $C_1$-$C_5$-halogenoalkoxy comprising up to 9 halogen atoms that can be the same or different;

$R^{35}$ represents a hydrogen atom; a halogen atom; substituted or non-substituted $C_1$-$C_5$-alkyl; a cyano; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or substituted or non-substituted di($C_1$-$C_5$-alkyl)amino;

$R^{36}$ represents a hydrogen atom or substituted or non-substituted $C_1$-$C_5$-alkyl;

a heterocycle of formula ($A^{14}$)

($A^{14}$)

wherein:

$R^{37}$ and $R^{38}$ that can be the same or different represent a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or a substituted or non-substituted $C_1$-$C_5$-alkylsulfanyl;

$R^{39}$ represents a hydrogen atom or substituted or non-substituted $C_1$-$C_5$-alkyl;

a heterocycle of formula ($A^{15}$)

($A^{15}$)

wherein:

R$^{40}$ and R$^{41}$ that can be the same or different represent a hydrogen atom; a halogen atom; substituted or non-substituted C$_1$-C$_5$-alkyl or C$_1$-C$_5$-halogenoalkyl comprising up to 9 halogen atoms that can be the same or different;

a heterocycle of formula (A$^{16}$)

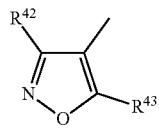
(A$^{16}$)

wherein:

R$^{42}$ and R$^{43}$ that can be the same or different represent a hydrogen atom; a halogen atom; substituted or non-substituted C$_1$-C$_5$-alkyl; C$_1$-C$_5$-halogenoalkyl comprising up to 9 halogen atoms that can be the same or different or amino;

a heterocycle of formula (A$^{17}$)

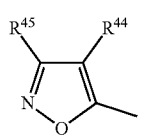
(A$^{17}$)

wherein:

R$^{44}$ and R$^{45}$ that can be the same or different represent a hydrogen atom; a halogen atom; substituted or non-substituted C$_1$-C$_5$-alkyl or C$_1$-C$_5$-halogenoalkyl comprising up to 9 halogen atoms that can be the same or different;

a heterocycle of formula (A$^{18}$)

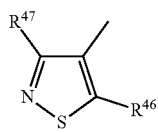
(A$^{18}$)

wherein:

R$^{47}$ represents a hydrogen atom; a halogen atom; substituted or non-substituted C$_1$-C$_5$-alkyl or C$_1$-C$_5$-halogenoalkyl comprising up to 9 halogen atoms that can be the same or different;

R$^{46}$ represents a hydrogen atom; a halogen atom; substituted or non-substituted C$_1$-C$_5$-alkyl; C$_1$-C$_5$-halogenoalkyl comprising up to 9 halogen atoms that can be the same or different or substituted or non-substituted C$_1$-C$_5$-alkylsulfanyl;

a heterocycle of formula (A$^{19}$)

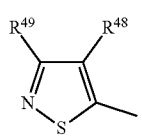
(A$^{19}$)

wherein:

R$^{49}$ and R$^{48}$ that can be the same or different represent a hydrogen atom; a halogen atom; substituted or non-substituted C$_1$-C$_5$-alkyl; substituted or non-substituted C$_1$-C$_5$-alkoxy; C$_1$-C$_5$-halogenoalkoxy comprising up to 9 halogen atoms that can be the same or different or C$_1$-C$_5$-halogenoalkyl comprising up to 9 halogen atoms that can be the same or different;

a heterocycle of formula (A$^{20}$)

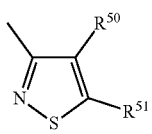
(A$^{20}$)

wherein:

R$^{50}$ and R$^{51}$ that can be the same or different represent a hydrogen atom; a halogen atom; substituted or non-substituted C$_1$-C$_5$-alkyl; substituted or non-substituted C$_1$-C$_5$-alkoxy; C$_1$-C$_5$-halogenoalkoxy comprising up to 9 halogen atoms that can be the same or different or C$_1$-C$_5$-halogenoalkyl comprising up to 9 halogen atoms that can be the same or different;

a heterocycle of formula (A$^{21}$)

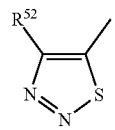
(A$^{21}$)

wherein:

R$^{52}$ represents a hydrogen atom; a halogen atom; substituted or non-substituted C$_1$-C$_5$-alkyl or C$_1$-C$_5$-halogenoalkyl comprising up to 9 halogen atoms that can be the same or different.

a heterocycle of formula (A$^{22}$)

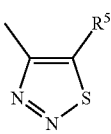
(A$^{22}$)

wherein:

R$^{53}$ represents a hydrogen atom; a halogen atom; substituted or non-substituted C$_1$-C$_5$-alkyl or C$_1$-C$_5$-halogenoalkyl comprising up to 9 halogen atoms that can be the same or different.

a heterocycle of formula (A$^{23}$)

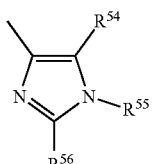
(A$^{23}$)

wherein:

$R^{54}$ and $R^{56}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;

$R^{55}$ represents a hydrogen atom or substituted or non-substituted $C_1$-$C_5$-alkyl;

a heterocycle of formula ($A^{24}$)

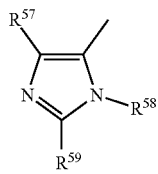

wherein:

$R^{57}$ and $R^{59}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;

$R^{58}$ represents a hydrogen atom or substituted or non-substituted $C_1$-$C_5$-alkyl;

a heterocycle of formula ($A^{25}$)

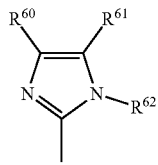

wherein:

$R^{60}$ and $R^{61}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;

$R^{62}$ represents a hydrogen atom or substituted or non-substituted $C_1$-$C_5$-alkyl;

a heterocycle of formula ($A^{26}$)

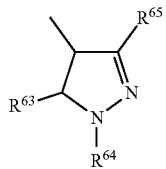

wherein:

$R^{65}$ represents a hydrogen atom; a halogen atom; substituted or non-substituted $C_1$-$C_5$-alkyl; substituted or non-substituted $C_3$-$C_5$-cycloalkyl; $C_1$-$C_5$-halogenoalkyl comprising up to 9 halogen atoms that can be the same or different; substituted or non-substituted $C_1$-$C_5$-alkoxy; substituted or non-substituted $C_2$-$C_6$-alkynyloxy or $C_1$-$C_5$-halogenoalkoxy comprising up to 9 halogen atoms that can be the same or different;

$R^{63}$ represents a hydrogen atom; a halogen atom; substituted or non-substituted $C_1$-$C_5$-alkyl; a cyano; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or di($C_1$-$C_8$-alkyl)amino;

$R^{64}$ represents a hydrogen atom or substituted or non-substituted $C_1$-$C_5$-alkyl.

More Preferred compounds according to the invention are compounds of formula (I) wherein A is selected in the list consisting of $A^2$; $A^5$; $A^6$; $A^{10}$ and $A^{13}$ as herein-defined.

Even More preferred compounds according to the invention are compounds of formula (I) wherein A represents $A^{13}$ wherein $R^{34}$ represents a substituted or non-substituted $C_1$-$C_5$-alkyl, $C_1$-$C_5$-halogenoalkyl comprising up to 9 halogen atoms that can be the same or different; substituted or non-substituted $C_1$-$C_5$-alkoxy; $R^{35}$ represents a hydrogen atom or a halogen atom and $R^{36}$ represents a substituted or non-substituted $C_1$-$C_5$-alkyl.

Even more preferred compounds according to the invention are compounds of formula (I) wherein A represents $A^{13}$ wherein $R^{34}$ represents $C_1$-$C_5$-alkyl, $C_1$-$C_5$-halogenoalkyl comprising up to 3 halogen atoms that can be the same or different; $R^{35}$ represents a hydrogen atom; a chlorine atom; or a fluorine atom; and $R^{36}$ represents a methyl.

Other preferred compounds according to the invention are compounds of formula (I) wherein T represents O.

Other preferred compounds according to the invention are compounds of formula (I) wherein n represents 1.

Other preferred compounds according to the invention are compounds of formula (I) wherein n represents 2.

Other preferred compounds according to the invention are compounds of formula (I) wherein m represents 1 or 2.

Other preferred compounds according to the invention are compounds of formula (I) wherein $L^1$ represents $CZ^4Z^5$.

Other preferred compounds according to the invention are compounds of formula (I) wherein $L^2$ represents $CZ^4Z^5$, O or S.

Other more preferred compounds according to the invention are compounds of formula (I) wherein $L^2$ represents $CZ^4Z^5$.

Other more preferred compounds according to the invention are compounds of formula (I) wherein $L^2$ represents O.

Other preferred compounds according to the invention are compounds of formula (I) wherein $Z^1$ represents a hydrogen atom.

Other preferred compounds according to the invention are compounds of formula (I) wherein $Z^2$ represents a hydrogen atom.

Other preferred compounds according to the invention are compounds of formula (I) wherein $Z^3$ represents a hydrogen atom, a halogen atom, $C_1$-$C_8$-alkyl, $C_1$-$C_8$-halogenoalkyl comprising up to 9 halogen atoms that can be the same or different, $C_1$-$C_8$-alkoxy or $C_1$-$C_8$-halogenoalkoxy comprising up to 9 halogen atoms that can be the same or different.

Other preferred compounds according to the invention are compounds of formula (I) wherein $Z^4$ and $Z^5$, independently represent a hydrogen atom or $C_1$-$C_8$-alkyl.

Other more preferred compounds according to the invention are compounds of formula (I) wherein $Z^4$ and $Z^5$ both represent a hydrogen atom.

The above mentioned preferences with regard to the substituents of the compounds according to the invention can be combined in various manners. These combinations of preferred features thus provide sub-classes of compounds according to the invention. Examples of such sub-classes of preferred compounds according to the invention are:

preferred features of A with preferred features of T, n, m, $Z^1$ to $Z^5$, $L^1$ and $L^2$;
preferred features of T with preferred features of A, n, m, $Z^1$ to $Z^5$, $L^1$ and $L^2$;
preferred features of n with preferred features of A, T, m, $Z^1$ to $Z^5$, $L^1$ and $L^2$;
preferred features of m with preferred features of A, T, n, $Z^1$ to $Z^5$, $L^1$ and $L^2$;
preferred features of $Z^1$ with preferred features of A, T, n, m, $Z^2$ to $Z^5$, $L^1$ and $L^2$;
preferred features of $Z^2$ with preferred features of A, T, n, m, $Z^1$, $Z^3$ to $Z^5$, $L^1$ and $L^2$;
preferred features of $Z^3$ with preferred features of A, T, n, m, $Z^1$ to $Z^2$, $Z^4$ to $Z^5$, $L^1$ and $L^2$;
preferred features of $Z^4$ with preferred features of A, T, n, m, $Z^1$ to $Z^3$, $Z^5$, $L^1$ and $L^2$;
preferred features of $Z^5$ with preferred features of A, T, n, m, $Z^1$ to $Z^4$, $L^1$ and $L^2$;
preferred features of $L^1$ with preferred features of A, T, n, m, $Z^1$ to $Z^5$ and $L^2$;
preferred features of $L^2$ with preferred features of A, T, n, m, $Z^1$ to $Z^5$ and $L^1$.

In these combinations of preferred features of the substituents of the compounds according to the invention, the said preferred features can also be selected among the more preferred features of each of A, T, n, m, $Z^1$ to $Z^5$, $L^1$ and $L^2$ so as to form most preferred subclasses of compounds according to the invention.

The present invention also relates to a process for the preparation of the compound of formula (I).

Thus, according to a further aspect of the present invention there is provided a process P1 for the preparation of a compound of formula (I) as herein-defined and wherein T represents O and that comprises reaction of a piperidine or pyrrolidine of formula (II) or one of its salts:

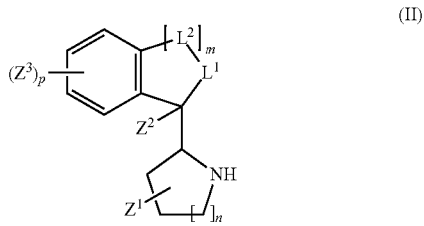

(II)

wherein $Z^1$, $Z^2$, $Z^3$, n, m, p, $L^1$ and $L^2$ are as herein-defined; with a carboxylic acid derivative of formula (III):

(III)

wherein A is as herein-defined and $U^1$ represents a leaving group selected in the list consisting of a halogen atom, a hydroxyl group, —$OR^a$, —OC(=O)$R^a$, $R^a$ being a substituted or non-substituted $C_1$-$C_8$-alkyl, a substituted or non-substituted $C_1$-$C_6$-haloalkyl, a benzyl, 4-methoxybenzyl or pentafluorophenyl group, or a group of formula O—C(=O) A; in the presence of a catalyst and in the presence of a condensing agent in case $U^1$ represents a hydroxyl group, and in the presence of an acid binder in case $U^1$ represents a halogen atom.

Pyrrolidines of formula (II) (n=1) can be prepared by condensation of the Grignard reagent derived from 1-(3-bromopropyl)-2,2,5,5-tetramethyl-1,2,5-azadisilolidine on an alpha-cyanobenzocycloalkene followed by an acidic cyclization to give the cylic imine which is further reduced to the wanted pyrrolidine according to Synthetic Communication (1996), 26, 3097.

In a similar way, piperidines of formula (II) (n=2) can be prepared by condensation of the Grignard reagent derived from 1-(4-bromobutyl)-2,2,5,5-tetramethyl-1,2,5-azadisilolidine on an alpha-cyanobenzo-cycloalkene followed by an acidic cyclization to give the cylic imine which is further reduced to the wanted piperidine according to Synthetic Communication (1996), 26, 3097.

Carboxylic acid derivatives of formula (III) can be prepared by known processes.

In case $U^1$ represents a hydroxy group, process P1 according to the present invention is conducted in the presence of condensing agent. Suitable condensing agent may be selected in the non limited list consisting of acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]-triazin-2-yl)-4-methylmorpholinium chloride hydrate, bromotripyrrolidinophosphoniumhexafluorophosphate or propanephosphonic anhydride (T3P).

Process P1 according to the present invention can be conducted in the presence of a catalyst. Suitable catalyst may be selected in the list consisting of N,N-dimethylpyridin-4-amine, 1-hydroxy-benzotriazole or N,N-dimethylformamide.

In case $U^1$ represents a halogen atom, process P1 according to the present invention is conducted in the presence of an acid binder. Suitable acid binders for carrying out process P1 according to the invention are in each case all inorganic and organic bases that are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as caesium carbonate, sodium carbonate, potassium carbonate, potassium bicarbonate, sodium bicarbonate, alkali metal or alkaline earth metal acetates, such as sodium acetate, potassium acetate, calcium acetate and also tertiary amines, such as trimethylamine, triethylamine, diisopropylethylamine, tributylamine, N,N-dimethylaniline, pyridine, N-methylpiperidine, N,N-dimethylpyridin-4-amine, diazabicyclooctane (DABCO), diazabicyclo-nonene (DBN) or diazabicycloundecene (DBU).

It is also possible to work in the absence of an additional condensing agent or to employ an excess of the piperidine or pyrrolidine or formula (II), so that it simultaneously acts as acid binder agent.

Suitable solvents for carrying out process P1 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone, or hexamethylphosphoric triamide; alcohols such as methanol, ethanol, propanol, iso-propanol; esters, such as methyl acetate or ethyl acetate, sulfoxides, such as dimethyl sulfoxide, or sulfones, such as sulfolane.

When carrying out process P1 according to the invention, the piperidine or pyrrolidine of formula (II) can be employed as its salt, such as chlorhydrate or any other convenient salt.

When carrying out process P1 according to the invention, 1 mole or an excess of the piperidine or pyrrolidine of formula (II) and from 1 to 3 moles of the acid binder can be employed per mole of the reagent of formula (III).

It is also possible to employ the reaction components in other ratios. Work-up is carried out by known methods.

According to a further aspect according to the invention, there is provided a process P2 for the preparation of a compound of formula (I) wherein T represents S, starting from a compound of formula (I) wherein T represents O and illustrated according to the following reaction scheme:

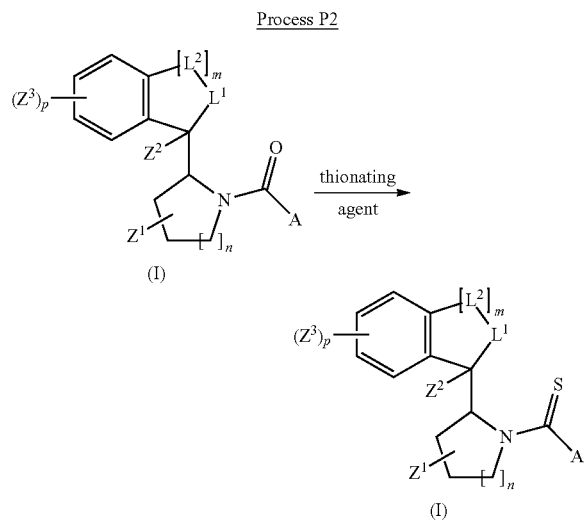

wherein A, $Z^1$, $Z^2$, $Z^3$, n, m, p, $L^1$ and $L^2$ are as hereindefined, in the optionally presence of a catalytic or stoichiometric or excess amount, quantity of a base such as an inorganic and organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylaminopyridine or N-methyl-piperidine.

Process P2 according to the invention is performed in the presence of a thionating agent.

Starting amide derivatives of formula (I) can be prepared according to process P1.

Suitable thionating agents for carrying out process P2 according to the invention can be sulfur (S), sulfhydric acid ($H_2S$), sodium sulfide ($Na_2S$), sodium hydrosulfide (NaHS), boron trisulfide ($B_2S_3$), bis(diethylaluminium)sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in Journal of the Chemical Society, Perkin 1 (2001), 358, in the optionally presence of a catalytic or stoichiometric or excess amount, quantity of a base such as an inorganic and organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylpyridin-4-amine or N-methyl-piperidine.

Suitable solvents for carrying out process P2 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin, chlorobenzene, dichlorobenzene, dichloromethane, chloroform, carbon tetrachloride, dichlorethane or trichlorethane, ethers, such as diethyl ether, diisopropyl ether, methyl t-butyl ether, methyl t-amyl ether, dioxane, tetrahydrofuran, 1,2-dimethoxyethane or 1,2-diethoxyethane, nitriles, such as acetonitrile, propionitrile, n- or i-butyronitrile or benzonitrile, sulfurous solvents, such as sulfolane or carbon disulfide.

When carrying out process P2 according to the invention, 1 mole or an excess of the sulfur equivalent of the thionating agent and from 1 to 3 moles of the base can be employed per mole of the amide reactant (I).

It is also possible to employ the reaction components in other ratios. Work-up is carried out by known methods.

Processes P1 and P2 according to the invention are generally carried out under atmospheric pressure. It is also possible to operate under elevated or reduced pressure.

When carrying out processes P1 and P2 according to the invention, the reaction temperatures can be varied within a relatively wide range. In general, these processes are carried out at temperatures from 0° C. to 200° C., preferably from 10° C. to 150° C. A way to control the temperature for the processes according to the invention is to use microwave technology.

In general, the reaction mixture is concentrated under reduced pressure. The residue that remains can be freed by known methods, such as chromatography or crystallization, from any impurities that can still be present.

Work-up is carried out by customary methods. Generally, the reaction mixture is treated with water and the organic phase is separated off and, after drying, concentrated under reduced pressure. If appropriate, the remaining residue can, be freed by customary methods, such as chromatography, crystallization or distillation, from any impurities that may still be present.

The compound according to the present invention can be prepared according to the general processes of preparation described above. It will nevertheless be understood that, on the basis of his general knowledge and of available publications, the skilled worker will be able to adapt this method according to the specifics of each of the compounds, which it is desired to synthesize.

The present invention thus provides compounds of formula (IIa) as well as their acceptable salts:

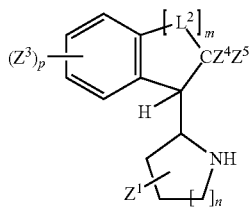

(IIa)

wherein $L^1$ is $CZ^4Z^5$ and $Z^1$, $Z^3$, $Z^4$, $Z^5$, $L^2$, n, m and p are as herein-defined, providing that (IIa) does not represent:
1-[3-(pyrrolidin-2-yl)-2,3-dihydro-1H-indol-1-yl]ethanone hydrochloride (1:1)
2-(6-methoxy-1,2,3,4-tetrahydronaphthalen-1-yl)pyrrolidine
2-(1,2,3,4-tetrahydronaphthalen-1-yl)pyrrolidine
2-(5,6-dimethoxy-1,2,3,4-tetrahydronaphthalen-1-yl)pyrrolidine.

The following compounds of formula (IIa) wherein $Z^2$ is a hydrogen atom, $L^1$ is $CZ^4Z^5$ and $Z^1$, $Z^3$, $Z^4$, $Z^5$, $L^2$, n, m and p are as herein-defined, are also mentioned in chemical databases and/or suppliers' databases but without any references or information which enables it to be prepared and separated:
2-(2,3-dihydro-1-benzothiophen-3-yl)pyrrolidine
8-(pyrrolidin-2-yl)-5,6,7,8-tetrahydronaphthalene-1-carboxamide
4-(piperidin-2-yl)-8-(trifluoromethyl)-1,2,3,4-tetrahydroquinoline
2-(3,4-dihydro-2H-chromen-4-yl)pyrrolidine
tert-butyl 5-(piperidin-2-yl)-2,3,4,5-tetrahydro-1H-1-benzazepine-1-carboxylate
1-[3-(pyrrolidin-2-yl)-2,3-dihydro-1H-indol-1-yl]ethanone
2-(2,3-dihydro-1-benzofuran-3-yl)pyrrolidine.

Preferred compounds of formula (IIa) according to the invention are:
2-(2,3-dihydro-1H-inden-1-yl)piperidine
2-(1,2,3,4-tetrahydronaphthalen-1-yl)piperidine
2-(6,7,8,9-tetrahydro-5H-benzo[7]annulen-5-yl)piperidine
2-(3,4-dihydro-2H-chromen-4-yl)piperidine
as well as their acceptable salts.

Other interesting compounds of formula (IIa) according to the invention are:
2-(4-fluoro-2,3-dihydro-1H-inden-1-yl)pyrrolidine
2-(5-fluoro-2,3-dihydro-1H-inden-1-yl)pyrrolidine
2-(5,7-difluoro-2,3-dihydro-1H-inden-1-yl)pyrrolidine
2-(5,7-dichloro-2,3-dihydro-1H-inden-1-yl)pyrrolidine
2-(6-tert-butyl-2,3-dihydro-1H-inden-1-yl)pyrrolidine,
as well as their acceptable salts.

In a further aspect, the present invention also relates to a fungicide composition comprising an effective and non-phytotoxic amount of an active compound of formula (I).

The expression "effective and non-phytotoxic amount" means an amount of composition according to the invention that is sufficient to control or destroy the fungi present or liable to appear on the crops and that does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials that are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with that the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulfonic acid salts, phenolsulfonic or naphthalenesulfonic acid salts, polycondensates of ethylene oxide with fatty alcohols or with fatty acids or with fatty amines, substituted phenols (in particular alkylphenols or arylphenols), salts of sulfosuccinic acid esters, taurine derivatives (in particular alkyl taurates), phosphoric esters of polyoxyethylated alcohols or phenols, fatty acid esters of polyols and derivatives of the above compounds containing sulfate, sulfonate and phosphate functions. The presence of at least one surfactant is generally essential when the active compound and/or the inert support are water-insoluble and when the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, that complies with the usual formulation techniques.

In general, the composition according to the invention can contain from 0.05 to 99% by weight of active compound, preferably 10 to 70% by weight.

Compositions according to the invention can be used in various forms and formulations such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

The formulations can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The compounds of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa, B. juncea* (e.g. mustard) and *Brassica carinata*, rice, wheat, sugarbeet, sugarcane, oats, rye, barley, millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. Nos. 11/765,491, 11/765, 494, 10/926,819, 10/782,020, 12/032,479, 10/783,417, 10/782,096, 11/657,964, 12/192,904, 11/396,808, 12/166, 253, 12/166,239, 12/166,124, 12/166,209, 11/762,886, 12/364,335, 11/763,947, 12/252,453, 12/209,354, 12/491, 396 or 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in Brassica species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an Eleusine EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312, 866, 11/315,678, 12/421,292, 11/400,598, 11/651,752, 11/681,285, 11/605,824, 12/468,205, 11/760,570, 11/762, 526, 11/769,327, 11/769,255, 11/943801 or 12/362,774. Plants comprising other genes that confer glyphosate tolerance, such as decarboxylase genes, are described in e.g. U.S. patent application Ser. Nos. 11/588,811, 11/185,342, 12/364, 724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from Streptomyces species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024782 and U.S. Patent Application No. 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: lifesci.sussex.ac.uk/Home/Neil_Crickmore/Bt/, or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026, WO 97/20936

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:
  a) Plants, such as cotton plants, containing an altered form of cellulose synthase genes as described in WO 98/00549
  b) Plants, such as cotton plants, containing an altered form of rsw2 or rsw3 homologous nucleic acids as described in WO 2004/053219
  c) Plants, such as cotton plants, with increased expression of sucrose phosphate synthase as described in WO 01/17333
  d) Plants, such as cotton plants, with increased expression of sucrose synthase as described in WO 02/45485
  e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938
  f) Plants, such as cotton plants, having fibers with altered reactivity, e.g. through the expression of N-acetylglucosaminetransferase gene including nodC and chitin synthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:
  a) Plants, such as oilseed rape plants, producing oil having a high oleic acid content as described e.g. in U.S. Pat. Nos. 5,969,169, 5,840,946 or 6,323,392 or 6,063,947
  b) Plants such as oilseed rape plants, producing oil having a low linolenic acid content as described in U.S. Pat. Nos. 6,270,828, 6,169,190, or 5,965,755
  c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230 WO09/068313 and WO10/006732.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (aphis.usda-.gov/). On the filing date of this application the petitions for nonregulated status that were pending with APHIS or granted by APHIS were those which contains the following information:
  Petition: the identification number of the petition. Technical descriptions of the transformation events can be found in the individual petition documents which are obtainable from APHIS, for example on the APHIS website, by reference to this petition number. These descriptions are herein incorporated by reference.
  Extension of Petition: reference to a previous petition for which an extension is requested.
  Institution: the name of the entity submitting the petition.
  Regulated article: the plant species concerned.
  Transgenic phenotype: the trait conferred to the plants by the transformation event.
  Transformation event or line: the name of the event or events (sometimes also designated as lines or lines) for which nonregulated status is requested.
  APHIS documents: various documents published by APHIS in relation to the Petition and which can be requested with APHIS.

Additional particularly useful plants containing single transformation events or combinations of transformation events are listed for example in the databases from various national or regional regulatory agencies.

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO 2006/128569); Event 1143-51B (cotton, insect control, not deposited, described in WO 2006/128570); Event 1445 (cotton, herbicide tolerance, not deposited, described in US-A 2002-120964 or WO 02/034946); Event 17053 (rice, herbicide tolerance, deposited as PTA-9843, described in WO 2010/117737); Event 17314 (rice, herbicide tolerance, deposited as PTA-9844, described in WO 2010/117735); Event 281-24-236 (cotton, insect control—herbicide tolerance, deposited as PTA-6233, described in WO 2005/103266 or US-A 2005-216969); Event 3006-210-23 (cotton, insect control—herbicide tolerance, deposited as PTA-6233, described in US-A 2007-143876 or WO 2005/103266); Event 3272 (corn, quality trait, deposited as PTA-9972, described in WO 2006/098952 or US-A 2006-230473); Event 40416 (corn, insect control—herbicide tolerance, deposited as ATCC PTA-11508, described in WO 2011/075593); Event 43A47 (corn, insect control—herbicide tolerance, deposited as ATCC PTA-11509, described in WO 2011/075595); Event 5307 (corn, insect control, deposited as ATCC PTA-9561, described in WO 2010/077816); Event ASR-368 (bent grass, herbicide tolerance, deposited as ATCC PTA-4816, described in US-A 2006-162007 or WO 2004/053062); Event B16 (corn, herbicide tolerance, not deposited, described in US-A 2003-126634); Event BPS-CV127-9 (soybean, herbicide tolerance, deposited as NCIMB No. 41603, described in WO 2010/080829); Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO 2006/128571); Event CE46-02A (cotton, insect control, not deposited, described in WO 2006/128572); Event COT102 (cotton, insect control, not deposited, described in US-A 2006-130175 or WO 2004/039986); Event COT202 (cotton, insect control, not deposited, described in US-A 2007-067868 or WO 2005/054479); Event COT203 (cotton, insect control, not deposited, described in WO 2005/054480); Event DAS40278 (corn, herbicide tolerance, deposited as ATCC PTA-10244, described in WO 2011/022469); Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO 2009/100188); Event DAS68416 (soybean, herbicide tolerance, deposited as ATCC PTA-10442, described in WO 2011/066384 or WO 2011/066360); Event DP-098140-6 (corn, herbicide tolerance, deposited as ATCC PTA-8296, described in US-A 2009-137395 or WO 2008/112019); Event DP-305423-1 (soybean, quality trait, not deposited, described in US-A 2008-312082 or WO 2008/054747); Event DP-32138-1 (corn, hybridization system, deposited as ATCC PTA-9158, described in US-A 2009-0210970 or WO 2009/103049); Event DP-356043-5 (soybean, herbicide tolerance, deposited as ATCC PTA-8287, described in US-A 2010-0184079 or WO 2008/002872); Event EE-1 (brinjal, insect control, not deposited, described in WO 2007/091277); Event F1117 (corn, herbicide tolerance, deposited as ATCC 209031, described in US-A 2006-059581 or WO 98/044140); Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control—herbicide tolerance, deposited as ATCC PTA-8398, described in WO 2008/151780); Event GHB614 (cotton, herbicide tolerance, deposited as ATCC PTA-6878, described in US-A 2010-050282 or WO 2007/017186); Event GJ11 (corn, herbicide tolerance, deposited as ATCC 209030, described in US-A 2005-188434 or WO 98/044140); Event GM RZ13 (sugar beet, virus resistance, deposited as NCIMB-41601, described in WO 2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO 2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO 03/013224 or US-A 2003-097687); Event LLRICE06 (rice, herbicide tolerance, deposited as ATCC-23352, described in U.S. Pat. No. 6,468,747 or WO 00/026345); Event LLRICE601 (rice, herbicide tolerance, deposited as ATCC PTA-2600, described in US-A 2008-2289060 or WO 00/026356); Event LY038 (corn, quality trait, deposited as ATCC PTA-5623, described in US-A 2007-028322 or WO 2005/061720); Event MIR162 (corn, insect control, deposited as PTA-8166, described in US-A 2009-300784 or WO 2007/142840); Event MIR604 (corn, insect control, not deposited, described in US-A 2008-167456 or WO 2005/103301); Event MON15985 (cotton, insect control, deposited as ATCC PTA-2516, described in US-A 2004-250317 or WO 02/100163); Event MON810 (corn, insect control, not deposited, described in US-A 2002-102582); Event MON863 (corn, insect control, deposited as ATCC PTA-2605, described in WO 2004/011601 or US-A 2006-095986); Event MON87427 (corn, pollination control, deposited as ATCC PTA-7899, described in WO 2011/062904); Event MON87460 (corn, stress tolerance, deposited as ATCC PTA-8910, described in WO 2009/111263 or US-A 2011-0138504); Event MON87701 (soybean, insect control, deposited as ATCC PTA-8194, described in US-A 2009-130071 or WO 2009/064652); Event MON87705 (soybean, quality trait—herbicide tolerance, deposited as ATCC PTA-9241, described in US-A 2010-0080887 or WO 2010/037016); Event MON87708 (soybean, herbicide tolerance, deposited as ATCC PTA9670, described in WO 2011/034704); Event MON87754 (soybean, quality trait, deposited as ATCC PTA-9385, described in WO 2010/024976); Event MON87769 (soybean, quality trait, deposited as ATCC PTA-8911, described in US-A 2011-0067141 or WO 2009/102873); Event MON88017 (corn, insect control—herbicide tolerance, deposited as ATCC PTA-5582, described in US-A 2008-028482 or WO 2005/059103); Event MON88913 (cotton, herbicide tolerance, deposited as ATCC PTA-4854, described in WO 2004/072235 or US-A 2006-059590); Event MON89034 (corn, insect control, deposited as ATCC PTA-7455, described in WO 2007/140256 or US-A 2008-260932); Event MON89788 (soybean, herbicide tolerance, deposited as ATCC PTA-6708, described in US-A 2006-282915 or WO 2006/130436); Event MS11 (oilseed rape, pollination control—herbicide tolerance, deposited as ATCC PTA-850 or PTA-2485, described in WO 01/031042); Event MS8 (oilseed rape, pollination control—herbicide tolerance, deposited as ATCC PTA-730, described in WO 01/041558 or US-A 2003-188347); Event NK603 (corn, herbicide tolerance, deposited as ATCC PTA-2478, described in US-A 2007-292854); Event PE-7 (rice, insect control, not deposited, described in WO 2008/114282); Event RF3 (oilseed rape, pollination control—herbicide tolerance, deposited as ATCC PTA-730, described in WO 01/041558 or US-A 2003-188347); Event RT73 (oilseed rape, herbicide tolerance, not deposited, described in WO 02/036831 or US-A 2008-070260); Event T227-1 (sugar beet, herbicide tolerance, not deposited, described in WO 02/44407 or US-A 2009-265817); Event T25 (corn, herbicide tolerance, not deposited, described in US-A 2001-029014 or WO 01/051654); Event T304-40 (cotton, insect control—herbicide tolerance, deposited as ATCC PTA-8171, described in US-A 2010-077501 or WO 2008/122406); Event T342-142 (cotton, insect control, not deposited, described in WO 2006/128568); Event TC1507 (corn, insect control—herbicide tolerance, not deposited, described in US-A 2005-039226 or WO 2004/099447); Event VIP1034 (corn, insect control—herbicide tolerance, deposited as ATCC PTA-3925., described in WO 03/052073), Event 32316 (corn, insect control-herbicide tolerance, deposited as PTA-11507, described in WO 2011/084632), Event 4114 (corn, insect control-herbicide tolerance, deposited as PTA-11506, described in WO 2011/084621).

Among the diseases of plants or crops that can be controlled by the method according to the invention, mention can be made of:

Powdery mildew diseases such as:
  Blumeria diseases, caused for example by *Blumeria graminis;*
  Podosphaera diseases, caused for example by *Podosphaera leucotricha;*
  Sphaerotheca diseases, caused for example by *Sphaerotheca fuliginea;*
  Uncinula diseases, caused for example by *Uncinula necator;*
Rust diseases such as:
  Gymnosporangium diseases, caused for example by *Gymnosporangium sabinae;*

*Hemileia* diseases, caused for example by *Hemileia vastatrix*;
*Phakopsora* diseases, caused for example by *Phakopsora pachyrhizi* or *Phakopsora meibomiae*;
*Puccinia* diseases, caused for example by *Puccinia recondite*, *Puccinia graminis* or *Puccinia striiformis*;
*Uromyces* diseases, caused for example by *Uromyces appendiculatus*;
Oomycete diseases such as:
*Albugo* diseases caused for example by *Albugo candida*;
*Bremia* diseases, caused for example by *Bremia lactucae*;
*Peronospora* diseases, caused for example by *Peronospora pisi* or *P. brassicae*;
*Phytophthora* diseases, caused for example by *Phytophthora infestans*;
*Plasmopara* diseases, caused for example by *Plasmopara viticola*;
*Pseudoperonospora* diseases, caused for example by *Pseudoperonospora humuli* or *Pseudoperonospora cubensis*;
*Pythium* diseases, caused for example by *Pythium ultimum*;
Leafspot, leaf blotch and leaf blight diseases such as:
*Alternaria* diseases, caused for example by *Alternaria solani*;
*Cercospora* diseases, caused for example by *Cercospora beticola*;
*Cladiosporum* diseases, caused for example by *Cladiosporum cucumerinum*;
*Cochliobolus* diseases, caused for example by *Cochliobolus sativus* (Conidiaform: *Drechslera*, Syn: *Helminthosporium*) or *Cochliobolus miyabeanus*;
*Colletotrichum* diseases, caused for example by *Colletotrichum lindemuthanium*;
*Cycloconium* diseases, caused for example by *Cycloconium oleaginum*;
*Diaporthe* diseases, caused for example by *Diaporthe citri*;
*Elsinoe* diseases, caused for example by *Elsinoe fawcettii*;
*Gloeosporium* diseases, caused for example by *Gloeosporium laeticolor*;
*Glomerella* diseases, caused for example by *Glomerella cingulata*;
*Guignardia* diseases, caused for example by *Guignardia bidwelli*;
*Leptosphaeria* diseases, caused for example by *Leptosphaeria maculans*; *Leptosphaeria nodorum*;
*Magnaporthe* diseases, caused for example by *Magnaporthe grisea*;
*Mycosphaerella* diseases, caused for example by *Mycosphaerella graminicola*; *Mycosphaerella arachidicola*; *Mycosphaerella fijiensis*;
*Phaeosphaeria* diseases, caused for example by *Phaeosphaeria nodorum*;
*Pyrenophora* diseases, caused for example by *Pyrenophora teres*, or *Pyrenophora tritici repentis*;
*Ramularia* diseases, caused for example by *Ramularia collocygni*, or *Ramularia areola*;
*Rhynchosporium* diseases, caused for example by *Rhynchosporium secalis*;
*Septoria* diseases, caused for example by *Septoria apii* or *Septoria lycopercisi*;
*Typhula* diseases, caused for example by *Typhula incamata*;
*Venturia* diseases, caused for example by *Venturia inaequalis*;

Root, Sheath and stem diseases such as:
*Corticium* diseases, caused for example by *Corticium graminearum*;
*Fusarium* diseases, caused for example by *Fusarium oxysporum*;
*Gaeumannomyces* diseases, caused for example by *Gaeumannomyces graminis*;
*Rhizoctonia* diseases, caused for example by *Rhizoctonia solani*;
*Sarocladium* diseases caused for example by *Sarocladium oryzae*;
*Sclerotium* diseases caused for example by *Sclerotium oryzae*;
*Tapesia* diseases, caused for example by *Tapesia acuformis*;
*Thielaviopsis* diseases, caused for example by *Thielaviopsis basicola*;
Ear and panicle diseases such as:
*Alternaria* diseases, caused for example by *Alternaria* spp.;
*Aspergillus* diseases, caused for example by *Aspergillus flavus*;
*Cladosporium* diseases, caused for example by *Cladosporium* spp.;
*Claviceps* diseases, caused for example by *Claviceps purpurea*;
*Fusarium* diseases, caused for example by *Fusarium culmorum*;
*Gibberella* diseases, caused for example by *Gibberella zeae*;
*Monographella* diseases, caused for example by *Monographella nivalis*;
Smut and bunt diseases such as:
*Sphacelotheca* diseases, caused for example by *Sphacelotheca reiliana*;
*Tilletia* diseases, caused for example by *Tilletia caries*;
*Urocystis* diseases, caused for example by *Urocystis occulta*;
*Ustilago* diseases, caused for example by *Ustilago nuda*;
Fruit rot and mould diseases such as:
*Aspergillus* diseases, caused for example by *Aspergillus flavus*;
*Botrytis* diseases, caused for example by *Botrytis cinerea*;
*Penicillium* diseases, caused for example by *Penicillium expansum*;
*Rhizopus* diseases caused by example by *Rhizopus stolonifer*
*Sclerotinia* diseases, caused for example by *Sclerotinia sclerotiorum*;
*Verticilium* diseases, caused for example by *Verticilium alboatrum*;
Seed and soilborne decay, mould, wilt, rot and damping-off diseases:
*Alternaria* diseases, caused for example by *Alternaria brassicicola*;
*Aphanomyces* diseases, caused for example by *Aphanomyces euteiches*;
*Ascochyta* diseases, caused for example by *Ascochyta lentis*;
*Aspergillus* diseases, caused for example by *Aspergillus flavus*;
*Cladosporium* diseases, caused for example by *Cladosporium herbarum*;
*Cochliobolus* diseases, caused for example by *Cochliobolus sativus*;
(Conidiaform: *Drechslera*, *Bipolaris* Syn: *Helminthosporium*);

*Colletotrichum* diseases, caused for example by *Colletotrichum coccodes*;
*Fusarium* diseases, caused for example by *Fusarium culmorum*;
*Gibberella* diseases, caused for example by *Gibberella zeae*;
*Macrophomina* diseases, caused for example by *Macrophomina phaseolina*;
*Monographella* diseases, caused for example by *Monographella nivalis*;
*Penicillium* diseases, caused for example by *Penicillium expansum*;
*Phoma* diseases, caused for example by *Phoma lingam*;
*Phomopsis* diseases, caused for example by *Phomopsis sojae*;
*Phytophthora* diseases, caused for example by *Phytophthora cactorum*;
*Pyrenophora* diseases, caused for example by *Pyrenophora graminea*;
*Pyricularia* diseases, caused for example by *Pyricularia oryzae*;
*Pythium* diseases, caused for example by *Pythium ultimum*;
*Rhizoctonia* diseases, caused for example by *Rhizoctonia solani*;
*Rhizopus* diseases, caused for example by *Rhizopus oryzae*;
*Sclerotium* diseases, caused for example by *Sclerotium rolfsii*;
*Septoria* diseases, caused for example by *Septoria nodorum*;
*Typhula* diseases, caused for example by *Typhula incamata*;
*Verticillium* diseases, caused for example by *Verticillium dahliae*;
Canker, broom and dieback diseases such as:
*Nectria* diseases, caused for example by *Nectria galligena*;
Blight diseases such as:
*Monilinia* diseases, caused for example by *Monilinia laxa*;
Leaf blister or leaf curl diseases such as:
*Exobasidium* diseases caused for example by *Exobasidium vexans*;
*Taphrina* diseases, caused for example by *Taphrina deformans*;
Decline diseases of wooden plants such as:
*Esca* diseases, caused for example by *Phaemoniella clamydospora*;
*Eutypa* dyeback, caused for example by *Eutypa lata*;
*Ganoderma* diseases caused for example by *Ganoderma boninense*;
*Rigidoporus* diseases caused for example by *Rigidoporus lignosus*;
Diseases of Flowers and Seeds such as:
*Botrytis* diseases caused for example by *Botrytis cinerea*;
Diseases of Tubers such as:
*Rhizoctonia* diseases caused for example by *Rhizoctonia solani*;
*Helminthosporium* diseases caused for example by *Helminthosporium solani*;
Club root diseases such as:
*Plasmodiophora* diseases, cause for example by *Plamodiophora brassicae*;
Diseases caused by Bacterial Organisms such as:
*Xanthomonas* species for example *Xanthomonas campestris* pv. *oryzae*;
*Pseudomonas* species for example *Pseudomonas syringae* pv. *lachrymans*;
*Erwinia* species for example *Erwinia amylovora*.

The composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The compounds or mixtures according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus*.

The present invention further relates to the use of compounds of the formula (I) as herein defined for the control of phytopathogenic fungi.

The present invention further relates to the use of compounds of the formula (I) as herein defined for the treatment of transgenic plants.

The present invention further relates to the use of compounds of the formula (I) as herein defined for the treatment of seed and of seed of transgenic plants.

The present invention further relates to a process for producing compositions for controlling phytopathogenic harmful fungi, characterized in that derivatives of the formula (I) as herein defined are mixed with extenders and/or surfactants.

The various aspects of the invention will now be illustrated with reference to the following table of compound examples and the following preparation or efficacy examples.

Table 1 illustrates in a non-limiting manner examples of compounds of formula (I) according to the invention:

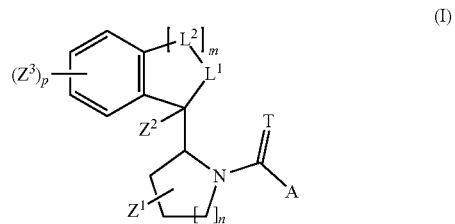

wherein A can be selected in the list consisting of the following groups: A-G1, A-G2, A-G3, A-G4, A-G5, A-G6, A-G7 and A-G8:

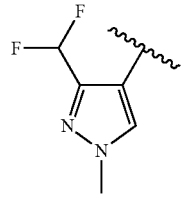

A-G1

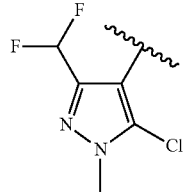

A-G2

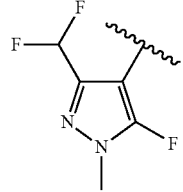

A-G3

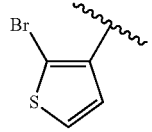

A-G4

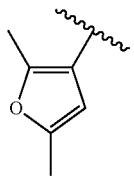

A-G5

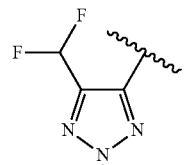

A-G6

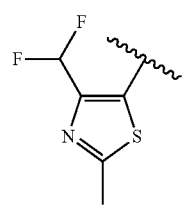

A-G7

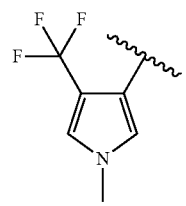

A-G8

In table 1, unless otherwise specified, M+H (Apcl+) means the molecular ion peak plus 1 a.m.u. (atomic mass unit) as observed in mass spectroscopy via positive atmospheric pressure chemical ionisation.

In table 1, the log P values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known log P values (determination of the log P values by the retention times using linear interpolation between two successive alkanones). lambda-max-values were determined using UV-spectra from 200 nm to 400 nm and the peak values of the chromatographic signals.

TABLE 1

| Example | A | T | n | $Z^1$ | m | | logP | Mass (M + H) |
|---|---|---|---|---|---|---|---|---|
| I.01 | A-G1 | O | 0 | H | 1 | 4-fluoro-2,3-dihydro-1H-inden-1-yl | 2.88 + 2.98 [1] | 364 |
| I.02 | A-G2 | O | 0 | H | 1 | 4-fluoro-2,3-dihydro-1H-inden-1-yl | 3.48 | 398 |
| I.03 | A-G3 | O | 0 | H | 1 | 4-fluoro-2,3-dihydro-1H-inden-1-yl | 3.31 + 3.35 [1] | 382 |
| I.04 | A-G4 | O | 0 | H | 1 | 4-fluoro-2,3-dihydro-1H-inden-1-yl [diastereoisomer 2] [2] | 3.87 | 394 |
| I.05 | A-G4 | O | 0 | H | 1 | 4-fluoro-2,3-dihydro-1H-inden-1-yl [diastereoisomer 1] [2] | 3.96 | 394 |
| I.06 | A-G5 | O | 0 | H | 1 | 4-fluoro-2,3-dihydro-1H-inden-1-yl [diastereoisomer 2] [2] | 3.74 | 328 |
| I.07 | A-G5 | O | 0 | H | 1 | 4-fluoro-2,3-dihydro-1H-inden-1-yl [diastereoisomer 1] [2] | 3.90 | 328 |
| I.08 | A-G1 | O | 0 | H | 1 | 5,7-dichloro-2,3-dihydro-1H-inden-1-yl | 3.61 | 414 |
| I.09 | A-G2 | O | 0 | H | 1 | 5,7-dichloro-2,3-dihydro-1H-inden-1-yl | 4.34 + 4.41 [1] | 448 |

TABLE 1-continued

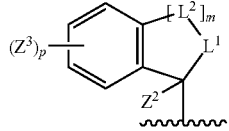

| Example | A | T | n | $Z^1$ | m | (structure) | logP | Mass (M + H) |
|---|---|---|---|---|---|---|---|---|
| I.10 | A-G3 | O | 0 | H | 1 | 5,7-dichloro-2,3-dihydro-1H-inden-1-yl | 4.14 | 432 |
| I.11 | A-G1 | O | 0 | H | 1 | 5,7-dichloro-2,3-dihydro-1H-inden-1-yl | 2.96 | 382 |
| I.12 | A-G2 | O | 0 | H | 1 | 5,7-dichloro-2,3-dihydro-1H-inden-1-yl | 3.55 + 3.59 [1] | 416 |
| I.13 | A-G3 | O | 0 | H | 1 | 5,7-dichloro-2,3-dihydro-1H-inden-1-yl | 3.35 + 3.41 [1] | 400 |
| I.14 | A-G6 | O | 0 | H | 1 | 5,7-dichloro-2,3-dihydro-1H-inden-1-yl [diastereoisomer 2] [2] | 3.41 | 383 |
| I.15 | A-G6 | O | 0 | H | 1 | 5,7-dichloro-2,3-dihydro-1H-inden-1-yl [diastereoisomer 1] [2] | 3.63 | 383 |
| I.16 | A-G2 | O | 0 | H | 1 | 5-fluoro-2,3-dihydro-1H-inden-1-yl | 3.50 | 398 |
| I.17 | A-G1 | O | 0 | H | 1 | 5-fluoro-2,3-dihydro-1H-inden-1-yl | 2.84 + 3.00 [1] | 364 |
| I.18 | A-G3 | O | 0 | H | 1 | 5-fluoro-2,3-dihydro-1H-inden-1-yl | 3.29 + 3.37 [1] | 382 |
| I.19 | A-G1 | O | 0 | H | 1 | 6-chloro-2,3-dihydro-1H-inden-1-yl | 3.19 + 3.27 [1] | 380 |
| I.20 | A-G2 | O | 0 | H | 1 | 6-chloro-2,3-dihydro-1H-inden-1-yl | 3.87 + 3.92 [1] | 414 |
| I.21 | A-G3 | O | 0 | H | 1 | 6-chloro-2,3-dihydro-1H-inden-1-yl | 3.68 + 3.70 [1] | 398 |
| I.22 | A-G1 | O | 0 | H | 1 | 6-tert-butyl-2,3-dihydro-1H-inden-1-yl | 4.16 | 402 |
| I.23 | A-G2 | O | 0 | H | 1 | 6-tert-butyl-2,3-dihydro-1H-inden-1-yl | 4.82 | 436 |
| I.24 | A-G3 | O | 0 | H | 1 | 6-tert-butyl-2,3-dihydro-1H-inden-1-yl | 4.67 | 406 [3] |
| I.25 | A-G2 | O | 0 | H | 2 | 1,2,3,4-tetrahydronaphthalen-1-yl | 3.68 + 3.79 [1] | 394 |
| I.26 | A-G3 | O | 0 | H | 2 | 1,2,3,4-tetrahydronaphthalen-1-yl | 3.48 + 3.61 [1] | 378 |
| I.27 | A-G1 | O | 0 | H | 2 | 1,2,3,4-tetrahydronaphthalen-1-yl | 2.94 + 3.21 [1] | 360 |
| I.28 | A-G2 | S | 0 | H | 2 | 1,2,3,4-tetrahydronaphthalen-1-yl | 4.56 + 4.77 [1] | 410 |
| I.29 | A-G1 | O | 1 | H | 1 | 2,3-dihydro-1H-inden-1-yl | 2.96 + 3.13 [1] | 360 |
| I.30 | A-G3 | O | 1 | H | 1 | 2,3-dihydro-1H-inden-1-yl | 3.44 + 3.55 [1] | 378 |
| I.31 | A-G3 | O | 1 | H | 2 | 1,2,3,4-tetrahydronaphthalen-1-yl | 3.67 | 392 |
| I.32 | A-G1 | O | 1 | H | 2 | 1,2,3,4-tetrahydronaphthalen-1-yl | 3.17 | 374 |
| I.33 | A-G1 | O | 1 | H | 3 | 6,7,8,9-tetrahydro-5H-benzo[7]annulen-5-yl | 3.50 + 3.68 [1] | 388 |
| I.34 | A-G3 | O | 1 | H | 3 | 6,7,8,9-tetrahydro-5H-benzo[7]annulen-5-yl | 3.96 + 4.15 [1] | 406 |
| I.35 | A-G1 | O | 1 | H | 2 | 3,4-dihydro-2H-chromen-4-yl | 2.46 + 2.90 [1] | 376 |
| I.36 | A-G3 | O | 1 | H | 2 | 3,4-dihydro-2H-chromen-4-yl | 2.86 + 3.27 [1] | 394 |
| I.37 | A-G7 | O | 0 | H | 1 | 5,7-difluoro-2,3-dihydro-1H-inden-1-yl [diastereoisomer 2] [2] | 3.52 | 399 |
| I.38 | A-G7 | O | 0 | H | 1 | 5,7-difluoro-2,3-dihydro-1H-inden-1-yl [diastereoisomer 1] [2] | 3.55 | 399 |
| I.39 | A-G8 | O | 0 | H | 1 | 5,7-difluoro-2,3-dihydro-1H-inden-1-yl [diastereoisomer 2] [2] | 3.68 | 399 |
| I.40 | A-G8 | O | 0 | H | 1 | 5,7-difluoro-2,3-dihydro-1H-inden-1-yl [diastereoisomer 1] [2] | 3.70 | 399 |
| I.41 | A-G3 | S | 0 | H | 1 | 4-fluoro-2,3-dihydro-1H-inden-1-yl | 4.01 | 398 |

Note

[1] mixture of two diastereoisomers

Note

[2] diastereoisomer 1: isomer with the highest Rf (retardation factor) by TLC (thin layer chromatography) on silica gel; diastereoisomer 2: isomer with the lowest Rf by TLC on silica gel Note

[3] (M—CH3) fragment

Table 2 illustrates in a non limiting manner examples of compounds of formula (IIa) according to the invention,

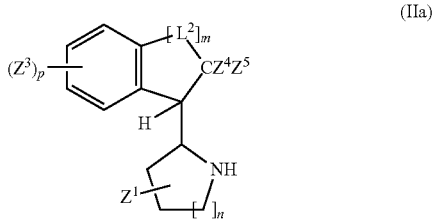
(IIa)

wherein $L^1$ is $CZ^4Z^5$ and $Z^1$, $Z^3$, $Z^4$, $Z^5$, $L^2$, n, m and p are as herein-defined.

In table 2, M+H (ApcI+) and log P are defined as for table 1.

TABLE 2

| Example | n | $Z^1$ | m | | logP | Mass (M + H) |
|---|---|---|---|---|---|---|
| IIa.01 | 1 | H | 1 | 2,3-dihydro-1H-inden-1-yl | 0.52 | |
| IIa.02 | 1 | H | 2 | 1,2,3,4-tetrahydronaphthalen-1-yl | 1.21 | |
| IIa.03 | 1 | H | 3 | 6,7,8,9-tetrahydro-5H-benzo[7]annulen-5-yl | 1.31 | |
| IIa.04 | 1 | H | 2 | 3,4-dihydro-2H-chromen-4-yl | 0.82 | |

Table 3 provides the NMR data ($^1$H) of a selected number of compounds from table 1.

The $^1$H-NMR data of selected examples are stated in the form of $^1$H-NMR peak lists. For each signal peak, the δ value in ppm and the signal intensity in brackets are listed.

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

The $^1$H-NMR peak lists are similar to classical $^1$H-NMR prints and contain therefore usually all peaks, which are listed at classical NMR-interpretation. Additionally they can show like classical $^1$H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-d6 and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values), can isolate the peaks of the target compounds as needed optionally using additional intensity filters. This isolation would be similar to relevant peak picking at classical $^1$H-NMR interpretation.

Further details of NMR-data description with peak lists can be found in the publication "Citation of NMR Peaklist Data within Patent Applications" of the Research Disclosure Database Number 564025.

TABLE 3

| | | NMR peak lists | |
|---|---|---|---|
| Example | Solvent | Frequency (Mhz) | $^1$H-NMR |
| I.01 | DMSO-d6 | 400 | 8.352 (3.1); 8.327 (1.2); 8.311 (1.3); 8.284 (3.3); 7.390 (0.7); 7.340 (0.4); 7.331 (0.5); 7.298 (1.0); 7.254 (1.7); 7.215 (1.0); 7.196 (3.2); 7.177 (3.0); 7.162 (3.6); 7.118 (1.0); 7.081 (2.2); 7.062 (2.0); 7.026 (1.1); 7.012 (1.7); 6.989 (2.5); 6.967 (1.9); 6.940 (2.1); 6.914 (2.8); 6.895 (2.1); 4.639 (1.3); 4.624 (1.3); 4.374 (0.6); 4.357 (1.4); 4.343 (1.4); 4.326 (0.7); 4.079 (1.3); 4.062 (1.4); 4.045 (1.4); 3.984 (0.4); 3.943 (12.5); 3.922 (11.1); 3.910 (6.3); 3.765 (0.5); 3.673 (1.5); 3.658 (1.4); 3.648 (1.5); 3.625 (1.9); 3.608 (2.0); 3.584 (1.1); 3.348 (521.9); 3.181 (0.5); 3.133 (1.5); 3.115 (4.2); 3.103 (4.4); 3.097 (4.8); 3.085 (4.2); 3.067 (1.5); 2.971 (0.9); 2.952 (1.5); 2.933 (1.8); 2.914 (1.9); 2.893 (2.2); 2.879 (1.2); 2.863 (1.6); 2.844 (1.6); 2.823 (1.5); 2.803 (0.9); 2.783 (0.7); 2.750 (0.4); 2.733 (1.1); 2.673 (1.2); 2.669 (1.0); 2.550 (2.3); 2.504 (172.8); 2.500 (146.3); 2.401 (0.3); 2.331 (1.3); 2.299 (0.4); 2.276 (0.7); 2.270 (0.7); 2.244 (0.9); 2.224 (0.8); 2.201 (0.4); 2.102 (0.5); 2.080 (1.0); 2.065 (1.3); 2.055 (1.1); 2.046 (1.5); 2.032 (1.3); 2.010 (0.8); 1.981 (0.9); 1.967 (1.1); 1.949 (1.2); 1.936 (1.4); 1.917 (2.0); 1.897 (2.6); 1.884 (2.9); 1.811 (0.3); 1.799 (0.4); 1.719 (2.2); 1.689 (1.6); 1.679 (1.0); 1.670 (1.2); 1.659 (1.1); 1.650 (0.9); 1.638 (1.2); 1.619 (0.8); 1.598 (0.4); 1.571 (0.8); 1.539 (0.9); 1.526 (0.9); 1.512 (0.9); 1.493 (0.9); 1.464 (1.1); 1.379 (1.2); 1.356 (0.7); 1.338 (0.8); 1.234 (0.4); 1.197 (7.9); 1.179 (16.0); 1.161 (7.7); 0.000 (7.1) |
| I.02 | DMSO-d6 | 400 | 8.315 (0.6); 7.341 (0.3); 7.237 (0.5); 7.223 (1.4); 7.219 (1.4); 7.204 (1.9); 7.186 (1.1); 7.151 (2.8); 7.142 (2.5); 7.134 (1.3); 7.123 (1.6); 7.119 (1.8); 7.016 (2.3); 7.000 (1.5); 6.984 (3.5); 6.961 (1.8); 6.940 (1.0); 6.882 (1.3); 6.850 (1.4); 4.684 (0.5); 4.671 (0.6); 4.665 (1.1); 4.652 (1.1); 4.633 (0.5); 4.346 (0.3); 4.329 (0.8); 4.315 (0.9); 4.298 (0.5); 4.187 (0.4); 4.168 (0.9); 4.154 (0.8); 4.135 (0.4); 3.950 (0.5); 3.940 (0.7); 3.928 (0.8); 3.917 (0.7); 3.893 (8.9); 3.881 (12.7); 3.834 (0.7); 3.407 (0.4); 3.345 (364.8); 3.304 (1.4); 3.292 (1.1); 3.275 (0.7); 3.207 (0.7); 3.188 (1.0); 3.169 (0.7); 3.162 (0.7); 3.142 (0.4); 3.133 (1.2); 3.121 (1.3); 3.115 (3.7); 3.103 (3.8); 3.097 (3.9); 3.085 (3.8); 3.079 (1.4); 3.067 (1.2); 2.991 (0.4); 2.978 (0.5); 2.962 (0.8); 2.951 (0.9); 2.934 (1.0); 2.913 (1.0); 2.892 (0.9); 2.885 (0.7); 2.876 (1.0); 2.857 (1.2); 2.836 (1.0); 2.817 (0.7); 2.796 (0.4); 2.677 (0.6); 2.672 (0.9); 2.668 (0.7); 2.550 (0.5); 2.536 (0.5); 2.526 (2.0); 2.521 (3.0); 2.512 (46.6); |

TABLE 3-continued

NMR peak lists

| Example | Solvent | Frequency (Mhz) | ¹H-NMR |
|---|---|---|---|
| | | | 2.508 (96.9); 2.503 (128.9); 2.499 (94.3); 2.494 (46.0); 2.335 (0.6); 2.330 (0.9); 2.326 (0.7); 2.293 (0.5); 2.282 (0.4); 2.271 (0.5); 2.260 (0.6); 2.249 (0.3); 2.239 (0.5); 2.148 (0.5); 2.137 (0.8); 2.126 (0.7); 2.115 (0.9); 2.104 (0.7); 2.094 (0.5); 2.082 (0.4); 2.021 (0.6); 2.004 (0.8); 1.989 (0.9); 1.972 (0.9); 1.956 (1.3); 1.944 (1.1); 1.936 (1.1); 1.927 (0.9); 1.922 (0.9); 1.909 (0.7); 1.904 (0.7); 1.886 (0.4); 1.830 (0.4); 1.821 (0.6); 1.811 (0.8); 1.803 (1.0); 1.792 (1.3); 1.780 (1.2); 1.773 (1.0); 1.762 (0.9); 1.754 (0.7); 1.741 (0.5); 1.734 (0.5); 1.650 (0.5); 1.627 (0.7); 1.606 (0.8); 1.596 (1.0); 1.571 (1.6); 1.554 (1.1); 1.537 (0.5); 1.514 (0.4); 1.494 (0.7); 1.486 (0.5); 1.481 (0.6); 1.468 (0.6); 1.460 (0.7); 1.456 (0.7); 1.438 (0.9); 1.418 (0.7); 1.407 (0.6); 1.385 (1.1); 1.196 (8.0); 1.178 (16.0); 1.159 (7.5); 0.000 (4.3) |
| I.03 | DMSO-d6 | 400 | 8.317 (0.4); 7.342 (0.5); 7.224 (0.8); 7.206 (2.1); 7.188 (2.4); 7.168 (1.7); 7.120 (1.3); 7.100 (2.4); 7.082 (1.8); 7.032 (1.6); 7.023 (1.6); 7.000 (2.2); 6.983 (3.9); 6.979 (3.9); 6.956 (2.5); 6.934 (1.3); 6.898 (0.9); 6.851 (1.3); 4.665 (0.5); 4.645 (1.3); 4.632 (1.3); 4.612 (0.6); 4.359 (0.4); 4.340 (0.8); 4.328 (0.9); 4.309 (0.4); 4.078 (0.5); 4.061 (1.1); 4.044 (1.1); 4.027 (0.5); 3.986 (0.7); 3.975 (0.9); 3.964 (0.9); 3.802 (8.3); 3.787 (11.4); 3.713 (0.3); 3.598 (0.7); 3.576 (1.2); 3.554 (1.2); 3.533 (0.9); 3.520 (0.8); 3.451 (0.7); 3.430 (1.1); 3.411 (1.2); 3.383 (1.1); 3.344 (434.2); 3.212 (0.5); 3.189 (0.9); 3.169 (0.9); 3.147 (0.4); 3.132 (1.2); 3.120 (1.3); 3.114 (3.7); 3.102 (3.8); 3.096 (3.9); 3.084 (3.8); 3.078 (1.5); 3.065 (1.2); 2.994 (0.4); 2.982 (0.5); 2.972 (0.5); 2.956 (1.0); 2.941 (0.9); 2.932 (1.1); 2.917 (1.0); 2.892 (2.4); 2.879 (1.2); 2.869 (1.7); 2.848 (1.3); 2.826 (1.2); 2.806 (0.7); 2.786 (0.5); 2.732 (0.7); 2.677 (0.8); 2.672 (1.1); 2.668 (0.8); 2.563 (0.6); 2.549 (1.1); 2.535 (0.9); 2.525 (2.4); 2.512 (58.6); 2.508 (118.1); 2.503 (155.4); 2.499 (114.4); 2.495 (57.1); 2.334 (0.8); 2.330 (1.1); 2.326 (0.8); 2.284 (0.6); 2.261 (0.6); 2.251 (0.7); 2.229 (0.7); 2.209 (0.4); 2.108 (0.4); 2.096 (0.4); 2.086 (0.7); 2.075 (1.0); 2.063 (1.0); 2.053 (1.3); 2.041 (1.3); 2.031 (1.4); 2.015 (1.2); 1.998 (0.8); 1.983 (0.5); 1.955 (0.5); 1.937 (0.9); 1.915 (1.4); 1.905 (1.3); 1.898 (1.4); 1.883 (1.3); 1.873 (0.9); 1.863 (1.1); 1.853 (1.0); 1.845 (0.9); 1.836 (1.0); 1.822 (0.9); 1.780 (0.4); 1.762 (0.7); 1.752 (0.8); 1.743 (0.8); 1.732 (1.0); 1.708 (0.7); 1.678 (0.7); 1.658 (0.9); 1.631 (0.9); 1.622 (0.8); 1.602 (1.3); 1.584 (1.7); 1.571 (2.0); 1.522 (0.4); 1.503 (0.8); 1.478 (0.9); 1.453 (0.6); 1.384 (0.8); 1.299 (0.6); 1.278 (0.7); 1.269 (0.6); 1.248 (0.6); 1.235 (0.4); 1.196 (7.8); 1.177 (16.0); 1.159 (7.6); 0.000 (8.4) |
| I.04 | CDCl3 | 500 | 7.303 (0.3); 7.281 (13.2); 7.270 (14.3); 7.263 (10.7); 7.167 (3.1); 7.151 (7.1); 7.141 (7.2); 7.125 (4.3); 7.056 (10.6); 7.041 (8.1); 7.033 (4.4); 7.022 (4.0); 6.999 (14.4); 6.988 (13.3); 6.883 (1.8); 6.865 (7.7); 6.847 (10.0); 6.830 (4.7); 6.771 (3.0); 6.756 (2.8); 6.002 (3.4); 5.991 (3.4); 5.296 (11.2); 4.781 (2.5); 4.770 (3.3); 4.765 (5.3); 4.755 (5.4); 4.749 (3.4); 4.739 (2.7); 4.445 (2.3); 4.430 (4.3); 4.418 (4.1); 4.404 (2.2); 4.073 (0.6); 4.059 (1.3); 4.047 (1.1); 4.034 (1.2); 4.021 (0.8); 4.009 (0.9); 3.994 (1.7); 3.981 (1.2); 3.600 (0.7); 3.590 (1.2); 3.582 (0.8); 3.574 (1.5); 3.566 (1.1); 3.559 (0.7); 3.548 (0.9); 3.536 (1.9); 3.524 (2.3); 3.515 (4.9); 3.503 (5.2); 3.494 (3.9); 3.482 (3.6); 3.449 (4.0); 3.438 (4.2); 3.433 (5.6); 3.416 (2.3); 3.412 (2.1); 3.098 (0.8); 3.093 (1.0); 3.082 (1.7); 3.077 (1.7); 3.066 (1.0); 3.060 (1.0); 3.049 (1.7); 3.040 (1.9); 3.031 (1.9); 3.017 (3.7); 3.007 (3.4); 2.998 (3.5); 2.988 (3.2); 2.946 (2.9); 2.929 (4.3); 2.913 (4.6); 2.896 (2.3); 2.881 (1.7); 2.825 (0.7); 2.820 (0.8); 2.807 (0.8); 2.801 (0.9); 2.793 (1.0); 2.787 (1.0); 2.775 (1.0); 2.769 (1.0); 2.599 (0.7); 2.582 (1.5); 2.565 (1.3); 2.549 (1.2); 2.533 (0.6); 2.347 (1.5); 2.337 (1.7); 2.329 (3.0); 2.320 (4.2); 2.311 (3.5); 2.303 (4.4); 2.293 (3.3); 2.285 (1.9); 2.275 (1.6); 2.204 (0.5); 2.186 (1.2); 2.177 (0.8); 2.169 (1.3); 2.160 (1.6); 2.151 (0.8); 2.143 (1.7); 2.132 (1.0); 2.125 (1.1); 2.119 (1.0); 2.104 (1.7); 2.089 (2.9); 2.082 (2.3); 2.072 (2.5); 2.050 (1.2); 2.035 (0.4); 2.009 (1.8); 1.995 (3.5); 1.991 (2.6); 1.982 (3.4); 1.977 (3.8); 1.969 (3.4); 1.963 (3.3); 1.955 (2.1); 1.950 (3.0); 1.936 (1.4); 1.889 (1.2); 1.882 (1.8); 1.874 (3.5); 1.868 (5.0); 1.857 (6.1); 1.853 (6.1); 1.847 (7.3); 1.842 (7.4); 1.835 (5.6); 1.828 (4.9); 1.817 (2.4); 1.810 (1.1); 1.800 (1.1); 1.789 (1.2); 1.784 (1.1); 1.766 (2.0); 1.745 (2.4); 1.739 (1.6); 1.728 (3.6); 1.723 (2.8); 1.719 (2.5); 1.713 (2.5); 1.707 (2.9); 1.703 (3.0); 1.692 (1.6); 1.683 (2.2); 1.670 (16.0); 1.581 (1.8); 1.567 (2.7); 1.562 (2.6); 1.556 (2.4); 1.550 (2.7); 1.546 (3.1); 1.543 (3.1); 1.536 (2.4); 1.530 (2.1); 1.519 (2.5); 1.504 (1.0); 0.000 (10.6) |
| I.05 | CDCl3 | 500 | 7.303 (9.5); 7.292 (11.0); 7.281 (1.8); 7.270 (0.9); 7.264 (7.4); 7.184 (0.4); 7.144 (2.8); 7.137 (10.5); 7.131 (11.0); 7.125 (5.5); 7.115 (4.2); 7.100 (1.7); 7.091 (0.6); 7.056 (0.5); 7.026 (10.2); 7.015 (9.6); 6.996 (2.3); 6.988 (1.4); 6.985 (1.5); 6.894 (2.8); 6.889 (2.5); 6.882 (3.4); 6.876 (5.0); 6.867 (2.3); 6.862 (2.9); 6.859 (2.5); 6.850 (0.8); 5.296 (6.6); 4.523 (2.0); 4.509 (3.6); 4.498 (3.7); 4.484 (1.7); 4.196 (2.0); 4.187 (3.2); 4.178 (3.5); 4.169 (3.1); 4.160 (1.7); 4.136 (0.5); 4.126 (0.7); 4.120 (0.7); 4.103 (0.4); 3.893 (0.4); 3.878 (0.6); 3.867 (0.6); 3.855 (0.6); 3.840 (0.3); 3.396 (2.0); 3.389 (2.6); 3.382 (2.7); 3.375 (4.2); 3.368 (3.5); 3.361 (2.9); 3.353 (2.7); 3.294 (2.2); 3.280 (3.0); 3.277 (3.2); 3.263 (3.0); 3.256 (2.1); 3.242 (1.6); 3.189 (0.6); 3.181 (0.7); 3.173 (0.6); 3.029 (1.0); 3.013 (1.8); 2.996 (3.3); 2.980 (5.0); 2.963 (5.2); 2.955 (3.2); 2.944 (3.1); 2.936 (3.1); 2.922 (1.0); 2.912 (1.2); 2.903 (0.9); 2.825 (0.6); 2.818 (0.6); 2.805 (0.6); 2.799 (0.6); 2.779 (0.5); 2.762 (0.8); 2.745 (0.6); 2.729 (0.4); 2.428 (1.2); 2.409 (2.6); 2.401 (1.6); 2.392 (2.6); 2.383 (2.9); 2.374 (1.3); 2.366 (2.6); 2.347 (1.1); 2.108 (0.4); 2.090 (0.8); 2.082 (0.7); 2.066 (1.3); 2.062 (1.4); 2.054 (1.8); 2.047 (2.4); 2.043 (2.9); 2.033 |

TABLE 3-continued

| | | | NMR peak lists |
|---|---|---|---|
| Example | Solvent | Frequency (Mhz) | $^1$H-NMR |
| | | | (3.7); 2.028 (2.8); 2.018 (3.9); 2.008 (4.2); 1.999 (3.1); 1.990 (3.4); 1.981 (3.0); 1.972 (2.3); 1.963 (2.1); 1.955 (1.1); 1.792 (0.5); 1.780 (0.6); 1.768 (0.8); 1.753 (0.9); 1.744 (1.0); 1.727 (1.0); 1.718 (1.1); 1.708 (1.2); 1.699 (1.5); 1.693 (1.3); 1.682 (2.3); 1.665 (16.0); 1.650 (2.0); 1.643 (3.2); 1.635 (1.2); 1.629 (2.0); 1.618 (0.8); 1.608 (1.2); 1.599 (1.7); 1.595 (2.0); 1.586 (3.0); 1.577 (2.5); 1.572 (2.6); 1.562 (2.5); 1.555 (2.8); 1.549 (2.7); 1.542 (3.0); 1.532 (2.1); 1.526 (2.3); 1.519 (2.6); 1.501 (1.9); 1.487 (0.8); 1.451 (0.4); 1.436 (0.5); 1.424 (0.5); 1.412 (0.5); 0.006 (0.6); 0.000 (7.8) |
| I.06 | CDCl3 | 500 | 7.266 (6.4); 7.146 (1.7); 7.131 (3.6); 7.120 (3.8); 7.105 (2.2); 7.046 (3.0); 7.032 (2.4); 7.006 (0.4); 6.990 (0.4); 6.969 (0.7); 6.955 (0.6); 6.869 (0.7); 6.848 (4.1); 6.831 (6.4); 6.813 (3.4); 6.227 (1.0); 6.041 (4.3); 5.296 (7.1); 4.756 (1.9); 4.746 (1.9); 4.478 (0.4); 4.322 (1.9); 4.312 (2.0); 4.208 (0.4); 4.193 (0.3); 3.721 (1.4); 3.707 (2.2); 3.689 (1.5); 3.454 (1.3); 3.442 (1.6); 3.434 (2.1); 3.422 (2.0); 3.005 (1.2); 2.991 (1.7); 2.977 (1.8); 2.934 (0.5); 2.915 (1.6); 2.900 (2.3); 2.884 (2.2); 2.868 (1.5); 2.851 (1.1); 2.513 (0.5); 2.479 (0.6); 2.466 (0.7); 2.463 (0.7); 2.457 (0.7); 2.437 (6.2); 2.425 (14.6); 2.389 (0.9); 2.380 (0.6); 2.367 (0.5); 2.353 (0.5); 2.346 (0.5); 2.338 (0.6); 2.333 (0.6); 2.316 (3.7); 2.306 (0.7); 2.289 (1.0); 2.265 (3.1); 2.248 (16.0); 2.217 (1.5); 2.212 (1.5); 2.193 (2.0); 2.184 (2.3); 2.175 (2.3); 2.167 (2.5); 2.159 (2.1); 2.116 (0.6); 2.096 (0.4); 2.081 (0.4); 2.074 (0.4); 2.050 (1.0); 2.034 (1.5); 2.006 (0.4); 1.992 (0.5); 1.982 (0.5); 1.961 (0.6); 1.922 (2.1); 1.905 (2.6); 1.893 (2.5); 1.879 (2.6); 1.866 (2.6); 1.861 (2.4); 1.852 (2.7); 1.840 (2.9); 1.829 (3.2); 1.816 (2.9); 1.791 (2.2); 1.773 (1.6); 1.749 (0.8); 1.730 (0.9); 1.710 (1.4); 1.694 (1.8); 1.679 (1.6); 1.673 (1.6); 1.652 (1.0); 1.637 (0.6); 1.618 (0.4); 1.608 (0.4); 1.592 (0.5); 1.573 (0.5); 1.563 (0.4); 1.552 (0.5); 1.523 (0.9); 1.499 (1.5); 1.485 (1.6); 1.446 (0.5); 0.000 (6.8) |
| I.07 | CDCl3 | 500 | 7.267 (3.8); 7.149 (0.5); 7.138 (1.3); 7.122 (2.2); 7.112 (2.1); 7.096 (1.2); 6.937 (2.3); 6.922 (2.1); 6.901 (0.6); 6.880 (2.6); 6.863 (3.7); 6.846 (2.1); 6.828 (0.4); 6.297 (1.1); 6.075 (3.8); 5.297 (3.2); 4.495 (0.7); 4.480 (1.2); 4.470 (1.2); 4.455 (0.7); 4.215 (1.1); 4.206 (1.2); 4.198 (1.2); 3.630 (1.0); 3.620 (1.2); 3.232 (0.7); 3.215 (1.3); 3.198 (1.2); 3.179 (0.5); 2.968 (0.7); 2.952 (2.6); 2.937 (3.4); 2.922 (2.5); 2.529 (0.4); 2.525 (0.3); 2.513 (0.5); 2.486 (10.8); 2.473 (3.9); 2.457 (0.8); 2.445 (0.6); 2.426 (0.5); 2.419 (0.4); 2.411 (0.4); 2.398 (0.7); 2.387 (0.7); 2.377 (1.1); 2.369 (1.0); 2.359 (1.3); 2.352 (1.5); 2.342 (3.6); 2.316 (0.9); 2.273 (16.0); 2.242 (0.5); 2.234 (0.3); 2.228 (0.5); 2.062 (0.7); 2.046 (0.3); 2.032 (0.7); 2.021 (1.1); 2.008 (1.5); 1.997 (1.6); 1.986 (1.3); 1.973 (0.9); 1.960 (0.4); 1.930 (1.1); 1.918 (1.2); 1.911 (1.2); 1.904 (1.3); 1.896 (1.2); 1.869 (0.5); 1.861 (0.4); 1.839 (0.3); 1.829 (0.4); 1.758 (0.3); 1.723 (0.3); 1.714 (0.3); 1.695 (0.4); 1.681 (0.6); 1.673 (0.7); 1.665 (0.6); 1.647 (0.9); 1.613 (2.4); 1.604 (2.2); 1.569 (0.6); 1.558 (0.4); 1.544 (0.4); 1.531 (0.4); 1.516 (0.4); 1.505 (0.4); 1.501 (0.4); 1.492 (0.4); 1.476 (0.3); 1.378 (0.5); 1.360 (0.9); 1.340 (1.0); 1.320 (0.7); 0.000 (3.9) |
| I.08 | DMSO-d6 | 400 | 8.268 (2.3); 8.211 (1.0); 7.952 (2.0); 7.307 (0.8); 7.271 (3.5); 7.223 (0.8); 7.202 (0.7); 7.087 (1.4); 7.065 (0.4); 6.951 (0.7); 4.738 (0.4); 4.720 (1.0); 4.704 (1.0); 4.687 (0.4); 4.470 (0.5); 3.990 (0.6); 3.974 (1.0); 3.953 (1.0); 3.942 (1.1); 3.916 (12.1); 3.788 (0.4); 3.712 (0.7); 3.688 (0.9); 3.669 (0.5); 3.656 (0.7); 3.637 (0.9); 3.626 (0.9); 3.599 (0.6); 3.573 (0.5); 3.560 (0.6); 3.542 (0.4); 3.426 (0.7); 3.409 (0.6); 3.401 (0.7); 3.383 (0.6); 3.344 (443.6); 3.291 (0.5); 3.284 (0.4); 3.272 (0.4); 3.118 (0.6); 3.097 (0.7); 3.076 (0.9); 3.053 (0.7); 2.914 (0.6); 2.892 (16.0); 2.852 (0.8); 2.830 (0.5); 2.812 (0.4); 2.786 (0.4); 2.732 (12.6); 2.677 (0.6); 2.673 (0.8); 2.668 (0.6); 2.526 (1.7); 2.521 (2.6); 2.512 (41.1); 2.508 (85.0); 2.503 (113.0); 2.499 (83.4); 2.495 (41.4); 2.335 (0.5); 2.330 (0.7); 2.326 (0.6); 2.225 (0.4); 2.106 (0.5); 2.097 (0.4); 2.084 (0.6); 2.074 (0.8); 2.051 (0.7); 2.028 (0.4); 2.000 (0.7); 1.966 (1.6); 1.959 (1.5); 1.945 (1.8); 1.805 (0.5); 1.786 (0.7); 1.768 (0.6); 1.756 (0.6); 1.737 (0.4); 1.713 (0.5); 1.694 (0.8); 1.680 (0.9); 1.665 (1.0); 1.648 (0.8); 1.571 (0.4); 1.543 (0.5); 1.527 (0.7); 1.510 (0.7); 1.495 (0.6); 1.477 (0.4); 1.430 (0.3); 0.000 (1.5) |
| I.09 | DMSO-d6 | 400 | 8.315 (0.3); 7.952 (2.0); 7.358 (3.8); 7.304 (4.1); 7.284 (2.4); 7.232 (2.9); 7.129 (1.8); 7.049 (0.6); 6.995 (3.2); 6.914 (1.2); 6.861 (2.0); 6.780 (0.7); 4.795 (0.5); 4.776 (1.2); 4.763 (1.2); 4.744 (0.7); 4.603 (0.7); 4.591 (0.7); 4.577 (0.4); 4.306 (0.7); 4.296 (1.1); 4.283 (1.4); 4.272 (1.1); 4.262 (0.7); 3.897 (0.9); 3.880 (15.6); 3.855 (8.0); 3.808 (0.7); 3.785 (0.4); 3.595 (0.7); 3.584 (0.7); 3.544 (0.4); 3.526 (0.3); 3.514 (0.4); 3.457 (0.5); 3.431 (1.3); 3.415 (1.6); 3.407 (1.8); 3.391 (2.8); 3.344 (471.2); 3.240 (0.5); 3.162 (0.3); 3.143 (0.5); 3.121 (0.8); 3.099 (1.2); 3.078 (1.3); 3.056 (1.2); 3.035 (0.7); 2.961 (0.9); 2.952 (1.0); 2.937 (1.0); 2.926 (1.0); 2.909 (0.8); 2.892 (16.0); 2.844 (0.6); 2.824 (0.6); 2.803 (0.5); 2.782 (0.5); 2.732 (13.1); 2.718 (0.4); 2.677 (0.8); 2.673 (1.1); 2.668 (0.8); 2.526 (2.7); 2.512 (58.7); 2.508 (120.5); 2.503 (161.6); 2.499 (121.9); 2.495 (62.5); 2.335 (0.8); 2.330 (1.1); 2.326 (0.8); 2.194 (0.3); 2.181 (0.6); 2.171 (0.7); 2.158 (0.9); 2.147 (1.2); 2.135 (1.4); 2.124 (1.6); 2.114 (1.2); 2.103 (1.4); 2.079 (0.9); 2.062 (0.7); 2.029 (1.1); 2.018 (1.4); 2.007 (1.1); 1.995 (1.3); 1.985 (1.2); 1.973 (0.9); 1.960 (0.9); 1.923 (0.4); 1.837 (0.8); 1.823 (1.0); 1.807 (1.5); 1.801 (1.5); 1.786 (1.2); 1.747 (0.4); 1.729 (0.6); 1.714 (0.7); 1.697 (0.8); 1.670 (1.1); 1.650 (1.4); 1.631 (2.2); 1.612 (1.8); 1.588 (0.8); 1.563 (0.4); 1.453 (0.5); 1.423 (1.1); 1.409 (1.2); 1.393 (0.9); 1.195 (0.5); 1.165 (0.5); 0.000 (3.2) |
| I.10 | DMSO-d6 | 400 | 8.316 (0.5); 7.953 (0.6); 7.323 (5.2); 7.294 (5.0); 7.250 (2.2); 7.113 (1.9); 6.978 (3.6); 6.844 (2.0); 4.775 (0.7); 4.756 (1.5); 4.740 (1.6); 4.722 (0.7); 4.519 (0.4); |

TABLE 3-continued

| | | NMR peak lists | |
|---|---|---|---|
| Example | Solvent | Frequency (Mhz) | $^1$H-NMR |
| | | | 4.508 (0.8); 4.500 (0.8); 4.490 (0.5); 4.129 (0.9); 4.120 (1.1); 4.116 (1.1); 4.107 (1.8); 4.098 (1.2); 4.085 (0.9); 3.848 (0.6); 3.829 (0.7); 3.804 (1.1); 3.783 (16.0); 3.767 (5.9); 3.720 (1.4); 3.586 (1.6); 3.568 (1.4); 3.531 (1.4); 3.514 (1.8); 3.497 (1.4); 3.470 (0.5); 3.379 (0.4); 3.366 (0.6); 3.335 (527.5); 3.295 (0.9); 3.286 (0.8); 3.275 (0.7); 3.253 (0.5); 3.245 (0.5); 3.228 (0.4); 3.135 (0.5); 3.113 (1.0); 3.091 (1.2); 3.070 (1.5); 3.049 (0.9); 3.026 (0.3); 3.005 (0.4); 2.984 (0.4); 2.936 (0.9); 2.927 (1.0); 2.912 (1.1); 2.903 (1.1); 2.891 (5.6); 2.869 (0.9); 2.860 (0.9); 2.850 (0.8); 2.827 (0.9); 2.809 (0.7); 2.786 (0.5); 2.732 (4.0); 2.681 (0.4); 2.676 (0.9); 2.672 (1.3); 2.667 (0.9); 2.663 (0.5); 2.525 (2.9); 2.521 (4.4); 2.512 (68.6); 2.507 (142.3); 2.503 (189.1); 2.498 (137.6); 2.494 (66.5); 2.339 (0.5); 2.334 (0.9); 2.330 (1.3); 2.325 (0.9); 2.321 (0.5); 2.241 (0.3); 2.211 (0.5); 2.185 (0.4); 2.138 (0.4); 2.115 (1.0); 2.105 (0.9); 2.092 (1.3); 2.082 (1.8); 2.070 (1.1); 2.059 (1.8); 2.037 (1.3); 2.018 (0.9); 2.004 (0.8); 1.984 (0.7); 1.960 (1.2); 1.947 (1.0); 1.937 (1.5); 1.927 (1.4); 1.917 (0.9); 1.903 (1.0); 1.861 (0.9); 1.839 (1.6); 1.815 (1.0); 1.704 (0.7); 1.687 (1.0); 1.667 (1.7); 1.646 (2.8); 1.627 (2.2); 1.588 (0.7); 1.486 (0.7); 1.469 (1.1); 1.453 (1.6); 1.437 (1.1); 0.000 (9.8) |
| I.11 | DMSO-d6 | 400 | 8.322 (0.3); 8.316 (0.6); 8.249 (3.7); 8.211 (4.2); 7.953 (1.9); 7.368 (0.6); 7.277 (1.2); 7.258 (0.6); 7.231 (1.2); 7.158 (0.4); 7.141 (2.3); 7.096 (0.6); 7.006 (1.3); 6.989 (1.4); 6.966 (1.5); 6.954 (1.9); 6.937 (2.8); 6.915 (2.9); 6.891 (1.6); 4.655 (0.5); 4.638 (1.4); 4.622 (1.4); 4.380 (0.5); 4.364 (1.1); 4.350 (1.2); 4.335 (0.6); 4.130 (1.8); 4.112 (1.9); 3.926 (16.0); 3.920 (15.0); 3.907 (2.8); 3.780 (0.4); 3.685 (0.4); 3.677 (0.6); 3.660 (1.5); 3.652 (1.8); 3.642 (2.0); 3.631 (1.8); 3.598 (1.3); 3.585 (0.9); 3.579 (1.1); 3.572 (1.1); 3.566 (0.9); 3.560 (1.0); 3.553 (0.9); 3.540 (0.8); 3.396 (0.6); 3.377 (1.3); 3.336 (505.4); 3.304 (0.8); 3.289 (0.5); 3.034 (1.0); 3.013 (1.3); 2.994 (1.5); 2.975 (0.9); 2.892 (15.5); 2.881 (1.0); 2.870 (1.2); 2.859 (1.4); 2.839 (1.3); 2.799 (0.6); 2.732 (12.2); 2.681 (0.4); 2.677 (0.9); 2.672 (1.2); 2.668 (0.9); 2.526 (2.6); 2.521 (3.9); 2.512 (62.6); 2.508 (131.0); 2.503 (175.4); 2.499 (129.3); 2.494 (63.8); 2.339 (0.4); 2.334 (0.8); 2.330 (1.2); 2.325 (0.9); 2.321 (0.5); 2.256 (0.5); 2.225 (0.7); 2.200 (0.6); 2.106 (0.5); 2.084 (1.0); 2.073 (0.9); 2.067 (0.9); 2.062 (1.0); 2.051 (1.6); 2.033 (1.3); 2.011 (0.7); 1.988 (0.4); 1.958 (1.8); 1.937 (2.6); 1.925 (2.9); 1.911 (2.6); 1.852 (0.4); 1.793 (0.7); 1.772 (1.1); 1.751 (1.2); 1.735 (1.6); 1.718 (1.7); 1.700 (1.5); 1.688 (1.4); 1.669 (1.1); 1.650 (0.5); 1.581 (0.5); 1.567 (0.9); 1.552 (1.0); 1.537 (1.4); 1.519 (1.3); 1.509 (0.9); 1.491 (0.7); 1.378 (1.8); 1.353 (0.6); 1.337 (0.4); 1.184 (1.2); 0.000 (8.9) |
| I.12 | DMSO-d6 | 400 | 7.953 (0.6); 7.122 (1.1); 7.090 (0.6); 6.997 (1.0); 6.987 (3.0); 6.977 (4.1); 6.955 (4.3); 6.914 (0.8); 6.853 (1.2); 6.821 (0.7); 4.671 (0.4); 4.651 (1.0); 4.637 (1.0); 4.618 (0.5); 4.380 (0.7); 4.365 (0.7); 4.350 (0.3); 4.301 (0.5); 4.285 (0.9); 4.266 (0.9); 3.878 (16.0); 3.846 (1.1); 3.835 (1.2); 3.339 (276.1); 3.297 (1.8); 3.275 (1.8); 3.257 (1.0); 3.071 (0.4); 3.052 (0.7); 3.031 (0.9); 3.012 (1.0); 2.998 (0.8); 2.991 (0.8); 2.975 (0.6); 2.926 (0.6); 2.905 (0.9); 2.892 (4.1); 2.867 (0.6); 2.843 (0.7); 2.818 (0.6); 2.797 (0.5); 2.776 (0.4); 2.732 (3.3); 2.673 (0.8); 2.507 (84.6); 2.503 (103.7); 2.500 (82.0); 2.330 (0.7); 2.225 (0.4); 2.194 (0.6); 2.170 (0.6); 2.161 (0.5); 2.153 (0.6); 2.140 (0.7); 2.128 (0.7); 2.118 (0.8); 2.105 (0.7); 2.097 (0.6); 2.081 (0.8); 2.055 (0.7); 2.025 (0.4); 2.001 (0.6); 1.985 (1.1); 1.964 (1.3); 1.951 (1.3); 1.936 (1.0); 1.915 (0.5); 1.803 (1.0); 1.794 (1.0); 1.776 (1.1); 1.760 (1.0); 1.742 (1.1); 1.729 (1.4); 1.712 (1.1); 1.686 (0.7); 1.668 (0.8); 1.659 (0.9); 1.636 (1.0); 1.617 (0.8); 1.587 (0.6); 1.569 (0.6); 1.555 (0.6); 1.539 (0.8); 1.520 (0.9); 1.493 (0.8); 1.468 (0.5); 0.000 (3.9) |
| I.13 | DMSO-d6 | 400 | 7.953 (0.9); 7.146 (0.5); 7.113 (1.2); 7.012 (1.0); 6.978 (3.0); 6.963 (4.5); 6.941 (4.7); 6.917 (1.5); 6.877 (0.7); 6.844 (1.4); 4.657 (0.5); 4.641 (1.2); 4.624 (1.2); 4.606 (0.5); 4.338 (0.6); 4.327 (0.7); 4.149 (0.5); 4.134 (1.0); 4.115 (1.1); 4.099 (0.8); 4.070 (0.6); 3.784 (16.0); 3.716 (0.5); 3.598 (0.6); 3.574 (1.1); 3.554 (0.9); 3.500 (0.7); 3.476 (0.8); 3.451 (1.1); 3.437 (0.9); 3.412 (0.6); 3.391 (0.4); 3.384 (0.4); 3.340 (377.8); 3.215 (0.4); 3.194 (0.6); 3.173 (0.6); 3.057 (0.4); 3.037 (0.6); 3.016 (1.0); 2.997 (1.1); 2.977 (0.9); 2.961 (0.6); 2.940 (0.3); 2.902 (0.7); 2.892 (6.3); 2.863 (1.3); 2.838 (1.0); 2.822 (0.7); 2.796 (0.4); 2.732 (5.2); 2.672 (0.8); 2.668 (0.6); 2.508 (88.8); 2.503 (115.1); 2.499 (87.0); 2.330 (0.8); 2.260 (0.4); 2.228 (0.6); 2.203 (0.5); 2.099 (0.6); 2.083 (0.7); 2.065 (1.1); 2.048 (1.2); 2.035 (0.9); 2.027 (0.9); 2.018 (0.8); 2.004 (0.6); 1.968 (0.8); 1.953 (1.2); 1.943 (1.1); 1.932 (1.2); 1.919 (1.2); 1.897 (0.7); 1.883 (0.6); 1.859 (0.9); 1.853 (0.9); 1.835 (0.9); 1.742 (0.7); 1.721 (1.1); 1.700 (1.2); 1.676 (0.9); 1.650 (1.2); 1.628 (1.4); 1.610 (0.9); 1.588 (0.5); 1.565 (0.6); 1.543 (0.8); 1.518 (0.8); 1.498 (0.5); 1.330 (0.4); 1.300 (0.5); 1.280 (0.3); 0.000 (5.5) |
| I.14 | CDCl3 | 500 | 7.347 (1.3); 7.281 (0.9); 7.265 (3.1); 7.239 (2.6); 7.173 (1.7); 7.131 (1.4); 7.066 (0.9); 6.727 (1.4); 6.711 (1.4); 6.571 (0.7); 6.569 (0.7); 6.553 (1.4); 6.550 (1.4); 6.534 (0.7); 6.531 (0.7); 6.512 (1.0); 6.496 (1.0); 6.480 (0.5); 6.461 (0.9); 6.443 (0.5); 5.298 (0.7); 5.294 (0.6); 5.280 (0.9); 5.264 (0.5); 4.901 (0.5); 4.888 (1.3); 4.875 (1.3); 4.861 (0.5); 4.316 (0.5); 4.303 (1.1); 4.289 (1.2); 4.271 (16.0); 4.126 (10.7); 4.047 (0.6); 4.039 (0.5); 4.031 (0.7); 4.024 (1.1); 4.016 (0.7); 4.009 (0.8); 4.001 (0.5); 3.881 (0.5); 3.871 (0.5); 3.866 (0.4); 3.855 (0.3); 3.840 (0.4); 3.825 (0.7); 3.809 (1.1); 3.802 (0.7); 3.794 (0.7); 3.786 (0.9); 3.771 (0.5); 3.745 (0.4); 3.737 (0.5); 3.728 (0.5); 3.720 (0.7); 3.712 (0.4); 3.695 (0.3); 3.454 (0.5); 3.438 (0.9); 3.422 (0.5); 3.056 (0.4); 3.039 (0.5); 3.024 (1.1); 3.006 (1.1); 2.992 (0.9); 2.972 (0.6); 2.954 (0.4); 2.897 (0.6); 2.880 (0.8); 2.866 (0.9); 2.842 (0.6); 2.835 (0.8); 2.819 (0.6); 2.805 (0.4); 2.790 (0.4); 2.787 (0.4); 2.209 (0.6); 2.204 (0.5); |

TABLE 3-continued

NMR peak lists

| Example | Solvent | Frequency (Mhz) | ¹H-NMR |
|---|---|---|---|
| | | | 2.201 (0.5); 2.191 (0.9); 2.186 (1.0); 2.174 (1.0); 2.165 (1.2); 2.161 (1.0); 2.148 (1.1); 2.130 (0.8); 2.118 (0.8); 2.111 (1.1); 2.105 (0.9); 2.098 (1.0); 2.085 (0.6); 2.067 (0.5); 2.045 (0.4); 2.036 (0.5); 2.026 (0.8); 2.022 (0.9); 2.017 (1.1); 2.008 (0.8); 2.002 (0.9); 1.993 (0.9); 1.984 (0.6); 1.976 (0.8); 1.970 (0.6); 1.964 (0.5); 1.959 (0.6); 1.954 (0.7); 1.950 (0.9); 1.938 (1.2); 1.933 (1.2); 1.921 (1.7); 1.911 (1.6); 1.895 (2.1); 1.887 (1.6); 1.880 (1.8); 1.863 (1.1); 1.856 (0.7); 1.847 (0.6); 1.839 (0.7); 1.823 (0.4); 1.644 (0.4); 1.628 (1.0); 1.614 (5.9); 1.605 (1.0); 1.589 (0.7); 0.000 (3.3) |
| I.15 | CDCl3 | 500 | 7.457 (1.3); 7.349 (2.6); 7.266 (2.1); 7.241 (1.4); 6.757 (1.3); 6.741 (1.4); 6.591 (0.7); 6.589 (0.7); 6.573 (1.3); 6.570 (1.3); 6.554 (0.7); 6.551 (0.7); 5.299 (1.6); 4.547 (0.5); 4.536 (1.0); 4.522 (1.1); 4.511 (0.6); 4.283 (16.0); 4.264 (1.2); 4.220 (2.4); 3.922 (0.5); 3.910 (0.7); 3.907 (0.7); 3.898 (0.9); 3.887 (1.0); 3.884 (0.9); 3.872 (0.7); 3.737 (0.6); 3.723 (1.3); 3.714 (0.7); 3.709 (0.8); 3.700 (1.1); 3.685 (0.6); 3.121 (0.3); 3.103 (0.7); 3.086 (0.7); 3.069 (0.9); 3.051 (0.5); 2.876 (0.8); 2.857 (0.8); 2.843 (0.6); 2.824 (0.6); 2.369 (0.9); 2.361 (0.5); 2.349 (0.9); 2.342 (1.1); 2.330 (0.4); 2.323 (1.0); 2.303 (0.3); 2.022 (0.8); 2.005 (0.8); 2.000 (0.8); 1.995 (0.8); 1.978 (0.7); 1.960 (0.8); 1.945 (1.0); 1.935 (1.0); 1.921 (1.1); 1.906 (0.5); 1.794 (0.5); 1.780 (0.7); 1.768 (0.8); 1.755 (1.0); 1.741 (0.7); 1.668 (0.7); 1.654 (0.9); 1.642 (1.0); 1.628 (0.9); 1.616 (4.4); 1.604 (0.9); 1.592 (0.9); 1.580 (1.0); 1.567 (1.0); 1.556 (0.7); 0.000 (2.2) |
| I.16 | DMSO-d6 | 400 | 8.312 (0.5); 7.953 (0.4); 7.297 (2.2); 7.283 (2.5); 7.276 (2.8); 7.263 (2.7); 7.146 (1.3); 7.114 (1.4); 7.073 (1.3); 7.049 (2.6); 7.020 (1.9); 7.012 (2.8); 6.979 (3.0); 6.969 (2.2); 6.948 (2.1); 6.930 (1.1); 6.924 (0.9); 6.877 (1.5); 6.845 (1.5); 4.674 (0.6); 4.655 (1.3); 4.642 (1.4); 4.623 (0.6); 4.329 (0.5); 4.312 (1.2); 4.297 (1.2); 4.280 (0.5); 4.068 (0.5); 4.051 (1.1); 4.035 (1.1); 4.019 (0.6); 3.892 (12.3); 3.880 (16.0); 3.864 (1.5); 3.851 (1.3); 3.840 (0.7); 3.827 (1.0); 3.816 (1.1); 3.805 (1.0); 3.409 (0.4); 3.403 (0.5); 3.396 (0.6); 3.344 (537.5); 3.313 (2.2); 3.301 (1.8); 3.287 (1.5); 3.273 (0.9); 3.204 (0.8); 3.185 (1.4); 3.165 (0.9); 3.158 (1.0); 3.138 (0.5); 2.966 (0.9); 2.944 (1.1); 2.925 (1.7); 2.913 (1.0); 2.903 (1.4); 2.893 (3.4); 2.868 (0.7); 2.846 (1.6); 2.828 (1.3); 2.808 (1.2); 2.790 (0.6); 2.781 (0.6); 2.769 (0.5); 2.750 (0.4); 2.733 (2.6); 2.678 (0.6); 2.673 (0.9); 2.669 (0.6); 2.526 (2.0); 2.513 (45.4); 2.509 (93.4); 2.504 (124.9); 2.500 (93.7); 2.496 (47.9); 2.335 (0.6); 2.331 (0.9); 2.327 (0.7); 2.264 (0.7); 2.254 (0.4); 2.242 (0.7); 2.232 (0.9); 2.221 (0.4); 2.211 (0.8); 2.130 (0.4); 2.121 (0.6); 2.109 (1.0); 2.099 (0.8); 2.088 (1.1); 2.076 (0.9); 2.067 (0.6); 2.055 (0.5); 2.019 (0.4); 2.001 (0.8); 1.984 (1.0); 1.970 (1.1); 1.951 (1.0); 1.937 (1.3); 1.926 (1.0); 1.916 (1.6); 1.904 (1.4); 1.898 (1.3); 1.883 (1.1); 1.870 (0.8); 1.866 (0.7); 1.847 (0.5); 1.830 (0.6); 1.811 (1.0); 1.803 (1.3); 1.791 (1.6); 1.780 (1.5); 1.773 (1.2); 1.761 (1.1); 1.753 (0.7); 1.741 (0.5); 1.733 (0.5); 1.672 (0.5); 1.651 (0.9); 1.629 (1.0); 1.608 (1.1); 1.596 (1.7); 1.577 (2.4); 1.560 (1.6); 1.544 (0.6); 1.498 (0.4); 1.478 (0.7); 1.471 (0.6); 1.465 (0.6); 1.451 (1.0); 1.444 (0.9); 1.432 (1.1); 1.421 (1.0); 1.402 (0.9); 1.382 (0.6); 1.363 (1.0); 1.255 (1.7); 1.188 (0.7); 0.000 (2.6) |
| I.17 | DMSO-d6 | 400 | 8.346 (3.4); 8.322 (0.6); 8.315 (0.8); 8.281 (3.3); 7.953 (1.6); 7.406 (0.4); 7.390 (0.8); 7.297 (1.0); 7.270 (0.5); 7.256 (1.9); 7.236 (1.1); 7.217 (1.5); 7.202 (1.3); 7.185 (0.3); 7.161 (2.1); 7.142 (0.4); 7.119 (0.9); 7.062 (1.8); 7.040 (3.6); 7.027 (3.4); 7.013 (1.8); 6.951 (1.6); 6.945 (2.1); 6.923 (3.3); 6.908 (1.7); 6.901 (1.9); 4.644 (0.5); 4.628 (1.2); 4.613 (1.3); 4.597 (0.5); 4.354 (0.8); 4.337 (1.7); 4.323 (1.8); 4.306 (0.9); 3.941 (16.0); 3.920 (13.0); 3.906 (4.0); 3.762 (0.6); 3.664 (1.3); 3.637 (1.5); 3.614 (1.9); 3.602 (1.9); 3.577 (1.0); 3.411 (0.6); 3.389 (1.3); 3.341 (649.2); 3.271 (0.4); 3.260 (0.3); 2.987 (0.3); 2.964 (0.8); 2.946 (1.2); 2.924 (1.7); 2.903 (1.5); 2.892 (13.4); 2.842 (1.3); 2.825 (1.8); 2.805 (1.5); 2.783 (1.2); 2.732 (10.4); 2.677 (0.9); 2.672 (1.3); 2.668 (0.9); 2.526 (2.7); 2.521 (4.1); 2.512 (65.4); 2.508 (135.2); 2.503 (179.3); 2.499 (130.5); 2.494 (63.2); 2.339 (0.4); 2.335 (0.9); 2.330 (1.2); 2.326 (0.9); 2.321 (0.5); 2.269 (0.4); 2.246 (0.6); 2.235 (0.5); 2.222 (0.7); 2.214 (0.8); 2.192 (0.7); 2.076 (0.4); 2.061 (0.7); 2.054 (0.9); 2.041 (1.3); 2.029 (1.2); 2.021 (1.3); 2.007 (1.4); 1.985 (0.8); 1.959 (0.8); 1.944 (1.1); 1.926 (1.3); 1.912 (1.4); 1.881 (2.2); 1.867 (2.3); 1.854 (2.2); 1.833 (1.4); 1.822 (1.0); 1.798 (0.5); 1.787 (0.4); 1.764 (0.7); 1.719 (2.0); 1.688 (1.5); 1.676 (0.8); 1.668 (1.1); 1.656 (1.1); 1.648 (0.8); 1.636 (1.3); 1.617 (0.9); 1.551 (0.8); 1.538 (0.8); 1.523 (0.7); 1.506 (0.5); 1.485 (0.6); 1.456 (1.0); 1.378 (1.9); 1.355 (0.7); 1.337 (0.8); 1.324 (0.7); 1.305 (0.6); 1.205 (0.4); 1.185 (1.5); 0.000 (4.8) |
| I.18 | DMSO-d6 | 400 | 8.315 (0.5); 7.952 (1.1); 7.251 (1.5); 7.237 (1.7); 7.231 (1.7); 7.217 (1.7); 7.165 (1.0); 7.125 (1.0); 7.115 (2.5); 7.091 (1.2); 7.076 (1.5); 7.038 (2.5); 7.031 (2.4); 7.015 (2.2); 6.980 (3.2); 6.963 (2.2); 6.958 (2.2); 6.938 (3.7); 6.919 (1.9); 6.915 (1.9); 6.896 (1.1); 6.846 (1.8); 4.653 (0.7); 4.634 (1.7); 4.620 (1.8); 4.601 (0.8); 4.341 (0.5); 4.323 (1.0); 4.310 (1.1); 4.291 (0.5); 3.955 (0.7); 3.937 (1.5); 3.921 (1.5); 3.904 (0.7); 3.871 (0.9); 3.859 (1.0); 3.848 (0.9); 3.800 (10.9); 3.785 (16.0); 3.699 (0.6); 3.592 (0.8); 3.568 (1.6); 3.546 (1.7); 3.529 (1.0); 3.516 (0.9); 3.448 (0.8); 3.427 (1.4); 3.406 (1.4); 3.381 (1.0); 3.372 (1.0); 3.339 (630.9); 3.302 (0.9); 3.293 (0.6); 3.287 (0.5); 3.269 (0.4); 3.205 (0.6); 3.186 (0.7); 3.176 (0.7); 3.163 (1.1); 3.144 (0.4); 2.963 (0.7); 2.942 (1.0); 2.923 (1.7); 2.901 (2.1); 2.891 (10.0); 2.850 (1.4); 2.829 (2.0); 2.810 (1.8); 2.787 (1.1); 2.771 (0.8); 2.732 (7.5); 2.677 (0.9); 2.672 (1.3); 2.668 (0.9); 2.663 (0.5); 2.526 (2.6); 2.521 (4.1); 2.512 (64.7); 2.508 (134.4); 2.503 (179.6); 2.499 (131.9); 2.494 (64.7); 2.339 (0.4); 2.334 (0.9); 2.330 (1.2); 2.325 (0.9); 2.254 (0.6); 2.243 (0.5); 2.231 (0.7); 2.222 (0.8); 2.209 |

TABLE 3-continued

| | | NMR peak lists | |
|---|---|---|---|
| Example | Solvent | Frequency (Mhz) | ¹H-NMR |
| | | | (0.5); 2.199 (0.7); 2.082 (0.6); 2.068 (0.6); 2.060 (1.1); 2.047 (1.4); 2.036 (1.4); 2.027 (2.1); 2.014 (1.9); 2.006 (1.9); 1.992 (1.9); 1.976 (0.9); 1.961 (0.5); 1.918 (0.6); 1.901 (1.4); 1.885 (1.8); 1.879 (1.8); 1.863 (2.2); 1.852 (2.1); 1.846 (2.1); 1.829 (1.8); 1.783 (0.6); 1.764 (1.0); 1.755 (1.0); 1.745 (1.0); 1.735 (1.3); 1.713 (0.9); 1.678 (0.9); 1.657 (1.2); 1.630 (1.2); 1.603 (1.8); 1.589 (2.0); 1.510 (0.5); 1.490 (1.0); 1.466 (1.1); 1.447 (0.6); 1.440 (0.7); 1.437 (0.7); 1.418 (0.3); 1.298 (0.7); 1.278 (0.7); 1.268 (0.7); 1.255 (0.6); 1.247 (0.6); 0.000 (10.3) |
| I.19 | DMSO-d6 | 400 | 8.308 (2.6); 8.305 (2.8); 8.285 (4.2); 7.952 (1.3); 7.387 (0.3); 7.297 (1.2); 7.266 (4.0); 7.241 (1.6); 7.220 (2.3); 7.215 (2.5); 7.205 (3.6); 7.164 (4.7); 7.147 (2.0); 7.132 (1.0); 7.118 (1.0); 7.060 (0.4); 7.037 (2.0); 7.027 (1.5); 4.648 (1.7); 4.633 (1.7); 4.616 (0.7); 4.371 (0.5); 4.355 (0.8); 4.340 (0.8); 4.323 (0.3); 4.038 (0.7); 4.021 (1.5); 4.004 (1.5); 3.987 (0.9); 3.947 (5.9); 3.924 (16.0); 3.786 (0.7); 3.672 (1.6); 3.663 (1.8); 3.651 (2.2); 3.630 (2.2); 3.611 (1.6); 3.452 (0.5); 3.357 (286.8); 3.354 (225.3); 3.350 (368.0); 3.346 (407.1); 3.133 (0.6); 3.121 (0.6); 3.115 (1.1); 3.103 (1.2); 3.097 (1.1); 3.085 (1.1); 3.079 (0.5); 3.066 (0.5); 2.934 (0.7); 2.922 (1.0); 2.913 (0.9); 2.895 (10.8); 2.882 (1.4); 2.859 (1.0); 2.816 (1.2); 2.797 (1.8); 2.777 (1.7); 2.754 (1.3); 2.736 (8.8); 2.679 (1.0); 2.675 (1.3); 2.670 (1.0); 2.564 (0.4); 2.559 (0.3); 2.550 (0.8); 2.536 (0.8); 2.528 (2.6); 2.523 (4.0); 2.515 (63.3); 2.510 (130.3); 2.506 (173.1); 2.501 (126.0); 2.497 (61.4); 2.341 (0.4); 2.337 (0.9); 2.332 (1.2); 2.328 (0.9); 2.228 (0.3); 2.200 (0.4); 2.178 (0.5); 2.063 (0.7); 2.048 (0.7); 2.041 (1.3); 2.029 (1.7); 2.017 (1.4); 2.008 (2.1); 1.994 (1.8); 1.987 (1.4); 1.973 (1.2); 1.962 (0.7); 1.944 (0.8); 1.927 (0.9); 1.897 (2.0); 1.879 (2.4); 1.862 (2.3); 1.851 (1.8); 1.828 (1.2); 1.800 (0.9); 1.753 (2.5); 1.738 (2.1); 1.719 (1.4); 1.712 (1.2); 1.700 (1.2); 1.680 (1.1); 1.662 (0.7); 1.641 (0.4); 1.620 (0.4); 1.458 (1.1); 1.450 (1.3); 1.434 (0.9); 1.418 (0.6); 1.400 (0.5); 1.381 (0.5); 1.201 (1.9); 1.183 (4.0); 1.165 (1.9); 1.092 (0.4); 0.000 (10.6); −0.009 (0.3) |
| I.20 | DMSO-d6 | 400 | 7.340 (4.3); 7.275 (0.4); 7.255 (1.1); 7.239 (2.0); 7.231 (1.0); 7.219 (3.8); 7.187 (2.6); 7.183 (2.6); 7.167 (1.5); 7.162 (1.4); 7.154 (0.7); 7.115 (1.8); 7.019 (1.1); 6.980 (3.2); 6.885 (0.7); 6.846 (2.0); 4.687 (0.5); 4.669 (1.3); 4.655 (1.3); 4.636 (0.6); 4.323 (0.4); 4.310 (0.4); 4.098 (0.6); 4.079 (1.2); 4.065 (1.2); 4.046 (0.5); 3.930 (0.4); 3.917 (0.5); 3.900 (4.7); 3.880 (16.0); 3.858 (0.9); 3.824 (0.3); 3.372 (2.0); 3.341 (413.5); 3.318 (1.8); 3.170 (0.5); 3.163 (0.3); 3.150 (0.4); 3.144 (0.5); 2.943 (0.4); 2.931 (0.6); 2.920 (0.5); 2.903 (0.9); 2.891 (2.4); 2.880 (1.0); 2.868 (1.0); 2.835 (0.8); 2.816 (1.5); 2.795 (1.4); 2.775 (0.8); 2.754 (0.6); 2.732 (1.1); 2.677 (0.5); 2.672 (0.7); 2.668 (0.5); 2.526 (1.6); 2.521 (2.4); 2.512 (36.1); 2.508 (75.2); 2.503 (100.6); 2.499 (73.5); 2.494 (35.8); 2.335 (0.5); 2.330 (0.7); 2.325 (0.5); 2.124 (0.4); 2.114 (0.7); 2.103 (1.0); 2.092 (0.8); 2.082 (1.2); 2.070 (0.9); 2.061 (0.6); 2.048 (0.5); 2.041 (0.4); 2.024 (0.4); 2.008 (0.4); 1.933 (0.6); 1.923 (0.4); 1.914 (1.2); 1.900 (0.8); 1.891 (1.3); 1.881 (1.0); 1.873 (0.7); 1.859 (0.9); 1.840 (0.9); 1.825 (1.5); 1.815 (1.7); 1.803 (1.7); 1.783 (1.0); 1.774 (0.6); 1.667 (0.5); 1.645 (0.8); 1.635 (0.6); 1.624 (0.7); 1.613 (0.8); 1.592 (0.8); 1.578 (0.8); 1.560 (0.5); 1.506 (0.4); 1.490 (0.7); 1.477 (0.6); 1.464 (0.8); 1.447 (0.5); 1.434 (0.6); 0.000 (2.7) |
| I.21 | DMSO-d6 | 400 | 8.310 (0.4); 8.308 (0.4); 8.304 (0.6); 7.953 (0.3); 7.282 (3.7); 7.245 (1.1); 7.227 (2.5); 7.209 (3.5); 7.173 (3.1); 7.153 (2.0); 7.133 (1.5); 7.111 (1.2); 7.021 (0.7); 6.975 (2.0); 6.842 (1.1); 6.837 (1.0); 4.669 (0.7); 4.650 (1.8); 4.635 (1.8); 4.617 (0.7); 4.345 (0.4); 4.333 (0.5); 4.011 (0.7); 3.994 (1.6); 3.976 (1.6); 3.959 (0.8); 3.935 (0.4); 3.925 (0.5); 3.914 (0.4); 3.812 (4.5); 3.790 (16.0); 3.696 (0.6); 3.593 (0.9); 3.570 (1.9); 3.550 (1.4); 3.465 (0.7); 3.442 (1.4); 3.424 (1.4); 3.401 (0.7); 3.342 (251.9); 3.339 (263.0); 3.224 (0.4); 3.202 (0.6); 3.180 (0.6); 3.157 (0.4); 2.941 (0.5); 2.928 (0.7); 2.918 (0.7); 2.896 (3.3); 2.888 (1.5); 2.878 (1.4); 2.867 (1.3); 2.851 (0.4); 2.823 (1.2); 2.803 (1.9); 2.783 (1.6); 2.763 (1.0); 2.736 (2.2); 2.679 (0.7); 2.675 (0.9); 2.670 (0.7); 2.528 (1.8); 2.514 (45.6); 2.510 (91.0); 2.506 (119.2); 2.501 (88.0); 2.337 (0.6); 2.332 (0.8); 2.328 (0.6); 2.226 (0.4); 2.204 (0.3); 2.077 (0.5); 2.064 (0.6); 2.055 (1.1); 2.043 (1.6); 2.033 (1.5); 2.022 (2.0); 2.010 (1.4); 2.001 (1.2); 1.988 (0.8); 1.914 (0.6); 1.895 (1.3); 1.874 (2.0); 1.857 (2.2); 1.843 (2.2); 1.826 (2.1); 1.812 (1.7); 1.793 (1.1); 1.782 (1.3); 1.762 (0.7); 1.722 (0.3); 1.700 (0.7); 1.679 (1.1); 1.652 (1.0); 1.625 (1.0); 1.607 (0.9); 1.518 (0.4); 1.500 (1.0); 1.489 (0.8); 1.476 (1.1); 1.445 (0.7); 1.261 (0.4); 1.237 (0.3); 0.000 (6.4) |
| I.22 | DMSO-d6 | 400 | 8.271 (1.1); 7.952 (0.4); 7.316 (0.6); 7.196 (0.7); 7.177 (1.5); 7.143 (1.1); 7.123 (0.6); 7.023 (1.3); 4.349 (0.6); 4.334 (0.5); 3.941 (6.4); 3.644 (0.5); 3.344 (117.5); 2.891 (2.8); 2.775 (0.3); 2.753 (0.4); 2.732 (2.5); 2.503 (33.8); 2.177 (0.3); 1.922 (0.4); 1.906 (0.4); 1.825 (0.4); 1.656 (0.3); 1.646 (0.4); 1.627 (0.4); 1.464 (0.3); 1.451 (0.4); 1.396 (0.3); 1.381 (0.4); 1.364 (0.4); 1.232 (1.3); 1.205 (16.0); 0.000 (0.5) |
| I.23 | DMSO-d6 | 400 | 7.264 (0.6); 7.200 (0.4); 7.183 (0.5); 7.180 (0.6); 7.155 (0.6); 7.036 (0.5); 3.900 (2.4); 3.874 (0.5); 3.342 (58.4); 2.891 (1.3); 2.732 (1.1); 2.512 (5.6); 2.508 (11.7); 2.503 (15.5); 2.499 (11.4); 2.494 (5.7); 1.272 (0.5); 1.255 (16.0); 0.000 (0.5) |
| I.24 | DMSO-d6 | 400 | 7.206 (0.4); 7.185 (1.0); 7.167 (1.1); 7.150 (0.9); 7.130 (0.5); 7.048 (0.6); 4.334 (0.4); 4.323 (0.4); 3.895 (0.3); 3.803 (3.3); 3.343 (67.8); 3.241 (0.4); 3.218 (0.4); 2.892 (1.3); 2.841 (0.4); 2.748 (0.3); 2.732 (1.2); 2.508 (18.4); 2.503 (23.3); 2.499 (18.2); 1.563 (0.6); 1.256 (16.0); 0.000 (0.9) |
| I.25 | DMSO-d6 | 400 | 7.953 (0.7); 7.322 (0.4); 7.303 (0.5); 7.272 (1.5); 7.264 (1.1); 7.258 (1.5); 7.254 (1.7); 7.154 (2.3); 7.142 (0.3); 7.136 (0.5); 7.123 (1.2); 7.108 (5.9); 7.102 (5.3); |

TABLE 3-continued

NMR peak lists

| Example | Solvent | Frequency (Mhz) | ¹H-NMR |
|---|---|---|---|
| | | | 7.096 (5.2); 7.085 (1.7); 7.071 (1.2); 7.061 (1.0); 7.054 (1.4); 7.042 (0.9); 7.020 (4.4); 6.981 (0.7); 6.886 (2.6); 6.846 (0.4); 4.296 (0.7); 4.285 (0.9); 4.279 (1.3); 4.268 (1.3); 4.250 (0.8); 3.895 (16.0); 3.881 (3.8); 3.869 (0.8); 3.843 (1.3); 3.536 (0.6); 3.523 (1.4); 3.511 (1.4); 3.387 (0.4); 3.379 (0.5); 3.367 (0.5); 3.358 (0.5); 3.327 (94.0); 3.299 (1.2); 3.286 (1.4); 3.273 (1.4); 3.258 (0.9); 3.179 (0.7); 3.160 (1.6); 3.153 (0.8); 3.141 (0.9); 3.134 (1.2); 3.114 (0.6); 2.891 (5.9); 2.748 (0.4); 2.732 (5.2); 2.720 (1.2); 2.706 (2.6); 2.691 (2.7); 2.676 (1.2); 2.650 (0.3); 2.578 (0.5); 2.524 (1.2); 2.511 (22.3); 2.507 (44.9); 2.502 (59.2); 2.497 (42.8); 2.493 (20.6); 2.329 (0.4); 1.971 (0.4); 1.954 (1.0); 1.936 (1.5); 1.923 (1.8); 1.911 (2.0); 1.902 (2.2); 1.888 (2.4); 1.875 (1.4); 1.848 (0.5); 1.778 (0.4); 1.763 (0.4); 1.755 (0.4); 1.744 (0.4); 1.734 (0.5); 1.715 (0.9); 1.692 (1.1); 1.681 (0.9); 1.672 (0.8); 1.657 (0.6); 1.652 (0.5); 1.610 (0.7); 1.595 (1.1); 1.572 (1.6); 1.559 (2.3); 1.542 (3.0); 1.523 (2.3); 1.508 (1.1); 1.494 (0.6); 1.478 (0.3); 1.464 (0.4); 1.450 (0.8); 1.433 (1.2); 1.417 (1.1); 1.402 (1.1); 1.387 (1.1); 1.364 (0.4); 1.235 (0.4); 0.000 (6.8) |
| I.26 | DMSO-d6 | 400 | 7.952 (0.5); 7.269 (0.7); 7.250 (0.9); 7.172 (1.7); 7.134 (0.9); 7.114 (3.7); 7.100 (12.7); 7.084 (5.8); 7.068 (3.1); 7.058 (2.6); 7.051 (2.5); 7.043 (3.1); 7.037 (3.7); 6.969 (1.1); 6.902 (1.8); 6.835 (0.7); 4.826 (0.5); 4.811 (0.5); 4.303 (0.9); 4.285 (1.9); 4.276 (1.9); 4.257 (0.9); 3.806 (16.0); 3.785 (5.6); 3.722 (0.6); 3.624 (0.7); 3.603 (0.9); 3.584 (0.5); 3.533 (2.9); 3.524 (3.1); 3.432 (0.4); 3.412 (0.4); 3.326 (117.9); 3.179 (0.7); 3.159 (1.5); 3.137 (1.5); 3.116 (0.6); 2.891 (3.3); 2.748 (0.3); 2.732 (3.1); 2.684 (4.5); 2.641 (0.5); 2.524 (1.8); 2.511 (33.7); 2.506 (66.4); 2.502 (86.7); 2.497 (63.5); 2.493 (31.5); 2.334 (0.4); 2.329 (0.6); 2.324 (0.4); 1.982 (1.1); 1.968 (1.6); 1.952 (1.8); 1.936 (1.7); 1.922 (1.4); 1.912 (1.3); 1.905 (1.3); 1.882 (2.8); 1.871 (2.6); 1.773 (0.4); 1.747 (0.8); 1.734 (0.8); 1.721 (0.9); 1.705 (0.6); 1.673 (1.1); 1.651 (1.7); 1.633 (1.8); 1.626 (1.8); 1.607 (2.0); 1.572 (4.7); 1.500 (1.2); 1.480 (0.8); 1.455 (0.4); 1.437 (0.6); 1.387 (0.4); 1.366 (0.6); 1.345 (1.2); 1.335 (0.9); 1.324 (1.3); 1.315 (1.3); 1.294 (1.0); 1.273 (0.4); 1.234 (0.5); 0.008 (0.4); 0.000 (10.4); −0.008 (0.4) |
| I.27 | DMSO-d6 | 400 | 8.332 (4.1); 8.284 (1.2); 7.953 (0.9); 7.399 (1.2); 7.263 (2.6); 7.243 (0.6); 7.224 (0.7); 7.127 (2.3); 7.119 (2.3); 7.106 (7.9); 7.097 (8.2); 7.094 (8.9); 7.084 (3.6); 7.070 (1.8); 7.048 (2.3); 7.037 (3.5); 7.026 (2.1); 6.991 (0.6); 4.823 (0.4); 4.808 (0.4); 4.319 (1.0); 4.309 (1.4); 4.301 (1.9); 4.291 (1.9); 4.274 (1.9); 4.012 (1.0); 3.974 (0.5); 3.947 (16.0); 3.917 (4.6); 3.901 (0.5); 3.781 (0.3); 3.695 (0.4); 3.679 (0.3); 3.620 (1.3); 3.610 (1.8); 3.601 (1.8); 3.594 (2.1); 3.590 (2.1); 3.584 (2.2); 3.575 (2.2); 3.564 (2.8); 3.392 (0.7); 3.372 (1.5); 3.330 (192.8); 3.300 (0.6); 2.891 (6.8); 2.748 (0.4); 2.732 (5.9); 2.693 (3.4); 2.681 (3.5); 2.672 (2.3); 2.640 (0.5); 2.525 (1.6); 2.520 (2.6); 2.511 (31.7); 2.507 (63.5); 2.502 (83.5); 2.498 (59.8); 2.493 (28.4); 2.334 (0.4); 2.329 (0.6); 2.324 (0.4); 1.889 (3.6); 1.878 (3.6); 1.733 (0.7); 1.721 (0.8); 1.711 (0.8); 1.693 (0.6); 1.684 (0.6); 1.663 (1.2); 1.652 (1.4); 1.644 (2.0); 1.633 (2.7); 1.624 (2.3); 1.613 (3.2); 1.593 (2.4); 1.539 (2.3); 1.523 (2.1); 1.507 (1.7); 1.434 (0.3); 1.414 (0.6); 1.396 (1.1); 1.387 (1.1); 1.381 (1.2); 1.364 (1.2); 1.347 (0.9); 1.329 (0.4); 1.234 (0.5); 0.000 (2.6) |
| I.28 | DMSO-d6 | 400 | 7.952 (1.7); 7.337 (0.5); 7.316 (0.4); 7.253 (0.4); 7.215 (0.8); 7.192 (1.4); 7.174 (1.3); 7.166 (1.5); 7.159 (2.0); 7.145 (1.4); 7.137 (1.7); 7.129 (7.9); 7.122 (6.6); 7.114 (4.2); 7.111 (4.1); 7.081 (2.8); 7.071 (2.9); 7.056 (3.2); 7.046 (2.2); 7.041 (1.9); 7.033 (1.0); 7.027 (0.6); 7.020 (0.7); 7.013 (0.4); 6.985 (0.5); 6.976 (0.7); 6.955 (1.0); 6.947 (1.2); 6.934 (0.4); 6.923 (1.6); 6.906 (0.6); 4.703 (1.3); 4.693 (1.2); 4.683 (0.9); 4.274 (0.4); 4.185 (0.4); 4.171 (0.7); 4.164 (0.7); 4.155 (1.0); 4.148 (1.0); 4.140 (0.6); 4.132 (0.5); 4.125 (0.5); 4.111 (1.0); 4.098 (1.3); 4.091 (0.7); 4.085 (0.9); 4.074 (0.4); 3.970 (0.5); 3.951 (0.5); 3.936 (0.5); 3.898 (16.0); 3.873 (8.7); 3.851 (1.2); 3.840 (0.8); 3.821 (5.0); 3.638 (0.7); 3.620 (0.6); 3.608 (0.6); 3.529 (0.4); 3.512 (0.7); 3.499 (1.3); 3.483 (1.2); 3.469 (1.1); 3.454 (0.5); 3.437 (0.4); 3.368 (0.6); 3.337 (259.0); 3.236 (0.4); 3.217 (1.0); 3.206 (0.7); 3.198 (1.0); 3.188 (0.9); 3.175 (4.1); 3.162 (3.8); 2.986 (0.4); 2.974 (0.4); 2.891 (12.6); 2.770 (0.6); 2.754 (0.5); 2.731 (11.6); 2.716 (2.6); 2.701 (3.0); 2.688 (1.3); 2.676 (0.8); 2.672 (0.9); 2.667 (0.8); 2.662 (0.7); 2.600 (1.3); 2.547 (2.4); 2.525 (1.5); 2.511 (35.8); 2.507 (73.3); 2.503 (97.3); 2.498 (73.1); 2.494 (37.5); 2.376 (0.4); 2.334 (0.5); 2.329 (0.6); 2.325 (0.5); 2.125 (0.6); 2.111 (0.9); 2.105 (1.0); 2.098 (1.0); 2.092 (1.0); 2.079 (0.8); 2.065 (0.8); 2.041 (0.3); 2.031 (0.3); 2.006 (0.3); 1.982 (0.5); 1.970 (0.7); 1.960 (0.8); 1.952 (0.9); 1.939 (1.1); 1.930 (1.1); 1.918 (1.3); 1.905 (1.2); 1.899 (1.2); 1.891 (1.2); 1.882 (1.0); 1.874 (1.1); 1.865 (1.1); 1.844 (0.9); 1.823 (0.9); 1.810 (1.0); 1.794 (0.9); 1.773 (0.7); 1.745 (0.4); 1.738 (0.5); 1.730 (0.6); 1.714 (0.8); 1.707 (0.9); 1.700 (1.0); 1.692 (1.0); 1.677 (0.9); 1.668 (0.9); 1.662 (0.8); 1.653 (0.8); 1.621 (0.5); 1.580 (1.7); 1.562 (2.5); 1.550 (2.7); 1.543 (3.0); 1.527 (2.5); 1.509 (1.5); 1.493 (0.9); 1.487 (0.9); 1.465 (0.8); 1.446 (0.5); 1.435 (0.5); 1.409 (0.4); 1.392 (0.6); 1.366 (1.1); 1.351 (1.4); 1.335 (1.2); 1.322 (0.9); 1.307 (0.7); 1.301 (0.7); 0.000 (4.5) |
| I.29 | CDCl3 | 400 | 8.016 (1.7); 7.519 (0.3); 7.480 (0.5); 7.310 (0.4); 7.261 (57.8); 7.245 (5.9); 7.219 (1.3); 7.210 (1.7); 7.202 (1.7); 7.164 (4.0); 7.147 (2.1); 7.134 (0.8); 6.803 (2.8); 6.666 (5.7); 6.528 (2.8); 5.212 (0.4); 4.830 (0.4); 3.948 (1.5); 3.882 (0.5); 3.767 (1.0); 3.741 (1.6); 3.720 (1.3); 3.615 (2.6); 3.125 (0.5); 3.117 (0.5); 3.100 (0.5); 3.054 (0.4); 2.955 (16.0); 2.883 (13.5); 2.882 (13.4); 2.839 (0.7); 2.822 (0.8); 2.816 (0.9); 2.805 (1.2); 2.799 (1.2); 2.782 (1.3); 2.776 (1.3); 2.661 (0.4); 2.655 (0.4); 2.284 (0.5); 2.261 (1.0); 2.251 (0.7); 2.240 (1.1); 2.228 (1.3); 2.217 (0.5); 2.207 |

TABLE 3-continued

| | | | |
|---|---|---|---|
| | | NMR peak lists | |
| Example | Solvent | Frequency (Mhz) | $^1$H-NMR |
| | | | (1.1); 2.184 (0.4); 2.081 (0.4); 2.057 (0.4); 2.037 (0.5); 2.002 (0.6); 1.892 (1.1); 1.872 (1.4); 1.832 (2.2); 1.800 (3.1); 1.794 (3.0); 1.769 (3.9); 1.735 (1.5); 1.675 (0.5); 1.615 (1.3); 1.574 (54.1); 1.524 (1.0); 1.478 (0.4); 1.255 (1.4); 0.008 (1.6); 0.000 (51.8); −0.009 (2.0); −0.050 (0.4) |
| I.30 | CDCl3 | 400 | 8.016 (1.7); 7.519 (0.3); 7.310 (0.4); 7.260 (61.5); 7.238 (1.2); 7.219 (1.1); 7.195 (1.2); 7.177 (2.4); 7.167 (3.3); 7.156 (3.5); 7.148 (3.2); 7.138 (2.1); 7.129 (2.1); 7.112 (5.1); 6.996 (0.4); 6.888 (0.4); 6.752 (0.8); 6.615 (0.5); 4.716 (0.5); 4.706 (0.5); 4.691 (0.5); 4.680 (0.4); 3.805 (4.2); 3.733 (3.5); 3.648 (1.2); 3.627 (0.8); 3.339 (0.5); 3.160 (0.4); 3.140 (0.5); 3.124 (0.5); 3.099 (0.4); 3.054 (0.3); 2.955 (16.0); 2.924 (0.3); 2.883 (13.9); 2.882 (13.6); 2.804 (1.0); 2.781 (1.0); 2.744 (0.4); 2.278 (0.8); 2.259 (0.9); 2.246 (1.0); 2.226 (0.8); 2.103 (0.4); 2.091 (0.4); 2.071 (0.7); 2.047 (0.8); 2.025 (0.5); 2.009 (0.5); 1.971 (1.4); 1.951 (1.9); 1.903 (0.7); 1.832 (2.3); 1.808 (2.5); 1.778 (2.9); 1.667 (0.3); 1.618 (1.1); 1.568 (66.9); 1.255 (1.6); 0.008 (1.8); 0.000 (56.7); −0.009 (2.0) |
| I.31 | CDCl3 | 400 | 8.017 (0.4); 7.261 (41.0); 7.104 (1.3); 7.087 (1.4); 6.997 (0.8); 6.954 (1.1); 5.621 (4.0); 4.976 (0.3); 3.825 (0.5); 3.801 (0.7); 3.789 (1.0); 3.766 (1.7); 3.679 (0.8); 3.646 (1.9); 3.628 (4.5); 3.609 (4.4); 3.591 (1.7); 3.279 (0.6); 3.106 (0.6); 3.088 (0.6); 2.955 (3.9); 2.882 (3.3); 2.771 (0.4); 2.654 (0.3); 2.043 (0.7); 2.015 (0.6); 1.931 (0.8); 1.853 (0.6); 1.798 (1.2); 1.737 (2.3); 1.724 (2.4); 1.603 (16.0); 1.546 (2.0); 1.492 (3.1); 1.473 (5.7); 1.455 (2.8); 1.421 (0.8); 1.403 (1.3); 1.385 (0.7); 1.255 (1.4); 0.008 (1.0); 0.000 (38.7); −0.008 (1.6) |
| I.32 | CDCl3 | 400 | 8.016 (0.6); 7.262 (24.9); 7.228 (0.6); 7.212 (0.6); 7.143 (0.7); 7.114 (1.5); 7.096 (1.1); 6.969 (1.2); 6.950 (0.9); 6.648 (0.5); 5.631 (4.6); 5.078 (0.8); 4.841 (0.3); 4.810 (0.4); 3.945 (0.7); 3.786 (0.4); 3.763 (0.4); 3.650 (1.4); 3.632 (4.4); 3.613 (5.0); 3.595 (3.6); 3.356 (0.5); 3.329 (0.5); 3.163 (0.3); 2.955 (5.9); 2.883 (4.8); 2.882 (4.9); 2.806 (0.4); 2.784 (0.7); 2.763 (0.6); 2.740 (0.4); 1.951 (0.5); 1.922 (0.7); 1.887 (0.6); 1.838 (0.4); 1.817 (0.4); 1.775 (0.5); 1.731 (1.3); 1.709 (1.5); 1.676 (1.6); 1.631 (16.0); 1.493 (3.2); 1.475 (6.0); 1.457 (3.0); 1.255 (0.6); 0.008 (0.8); 0.000 (23.2); −0.009 (0.8) |
| I.33 | CDCl3 | 400 | 8.016 (1.7); 7.479 (0.8); 7.261 (32.8); 7.143 (0.8); 7.111 (3.1); 6.997 (0.4); 6.944 (0.4); 6.807 (0.5); 6.671 (0.4); 6.635 (0.4); 3.953 (4.3); 3.790 (2.6); 3.502 (0.4); 3.440 (0.8); 3.124 (0.3); 2.955 (16.0); 2.883 (13.4); 2.882 (13.2); 2.720 (0.3); 1.973 (1.4); 1.779 (1.3); 1.730 (1.6); 1.675 (0.7); 1.625 (1.0); 1.576 (31.8); 1.526 (0.8); 1.395 (0.8); 1.385 (0.8); 1.255 (1.0); 0.008 (0.9); 0.000 (28.1); −0.009 (1.0) |
| I.34 | CDCl3 | 400 | 8.017 (0.9); 7.519 (0.4); 7.310 (0.5); 7.260 (79.3); 7.210 (0.4); 7.159 (0.6); 7.146 (0.7); 7.141 (1.2); 7.111 (3.7); 7.105 (2.2); 7.069 (2.6); 7.064 (3.3); 7.053 (12.4); 7.039 (4.6); 7.031 (2.2); 7.023 (1.8); 6.996 (0.5); 6.907 (0.7); 6.889 (1.3); 6.753 (1.6); 6.616 (0.8); 6.284 (1.5); 6.148 (3.1); 6.013 (1.6); 5.673 (1.0); 5.641 (1.1); 5.485 (0.4); 5.476 (0.3); 5.457 (0.4); 5.444 (0.3); 4.522 (0.6); 4.489 (0.6); 3.806 (5.5); 3.734 (3.9); 3.677 (16.0); 3.635 (0.4); 3.486 (1.3); 3.451 (2.0); 3.415 (2.8); 3.400 (2.1); 3.387 (1.1); 3.368 (1.1); 3.360 (1.3); 3.327 (1.7); 3.301 (0.6); 3.292 (0.7); 3.100 (0.4); 3.085 (0.4); 3.059 (0.5); 2.955 (8.1); 2.883 (7.0); 2.882 (6.9); 2.750 (1.3); 2.733 (1.2); 2.712 (1.1); 2.700 (0.9); 2.087 (0.4); 2.059 (0.5); 2.007 (1.7); 1.987 (2.6); 1.959 (2.2); 1.914 (1.6); 1.877 (1.9); 1.847 (2.4); 1.838 (2.7); 1.828 (2.5); 1.805 (1.9); 1.788 (2.1); 1.781 (2.5); 1.772 (2.2); 1.758 (3.2); 1.743 (3.7); 1.732 (4.0); 1.699 (2.8); 1.665 (2.3); 1.624 (1.0); 1.612 (1.3); 1.602 (1.1); 1.561 (115.6); 1.511 (1.2); 1.486 (0.7); 1.474 (0.9); 1.453 (1.2); 1.441 (1.7); 1.420 (1.9); 1.410 (1.8); 1.396 (1.6); 1.299 (0.5); 1.255 (1.8); 0.050 (0.4); 0.008 (2.4); 0.000 (70.9); −0.009 (2.2); −0.050 (0.3) |
| I.35 | CDCl3 | 400 | 8.016 (1.7); 7.520 (0.6); 7.483 (1.5); 7.450 (0.8); 7.311 (0.5); 7.261 (103.0); 7.212 (1.7); 7.193 (1.0); 7.157 (0.7); 7.140 (1.3); 7.122 (0.8); 7.119 (0.8); 7.043 (1.0); 7.022 (1.2); 6.997 (0.7); 6.952 (1.6); 6.937 (3.1); 6.913 (1.3); 6.892 (1.3); 6.876 (0.8); 6.858 (1.1); 6.842 (1.2); 6.825 (4.8); 6.816 (2.0); 6.807 (4.0); 6.791 (1.4); 6.779 (1.0); 6.722 (0.5); 6.653 (2.1); 6.515 (1.1); 5.538 (9.2); 5.306 (1.4); 5.026 (0.4); 5.006 (0.4); 4.994 (0.4); 4.879 (0.7); 4.848 (0.8); 4.525 (0.5); 4.514 (0.5); 4.261 (0.6); 4.234 (0.5); 4.174 (1.0); 4.152 (1.0); 3.967 (1.0); 3.944 (8.5); 3.916 (0.9); 3.871 (0.9); 3.854 (1.1); 3.753 (1.2); 3.724 (1.0); 3.671 (0.5); 3.622 (7.0); 3.604 (9.4); 3.586 (9.1); 3.567 (3.0); 3.464 (0.4); 3.444 (0.4); 3.407 (0.4); 3.364 (1.2); 3.329 (1.3); 3.297 (0.6); 3.269 (0.4); 3.229 (0.6); 3.194 (0.4); 3.147 (0.5); 3.125 (0.9); 3.107 (0.9); 3.099 (0.6); 3.088 (0.9); 3.070 (0.4); 2.955 (16.0); 2.883 (13.2); 2.882 (13.9); 2.653 (0.4); 2.125 (0.6); 2.088 (1.2); 2.077 (1.0); 2.067 (1.0); 2.057 (1.0); 2.043 (0.7); 2.033 (0.8); 1.998 (0.5); 1.953 (1.7); 1.915 (2.5); 1.885 (1.8); 1.861 (1.3); 1.817 (1.0); 1.742 (1.7); 1.716 (3.1); 1.710 (3.0); 1.687 (3.2); 1.672 (2.4); 1.650 (2.1); 1.598 (51.6); 1.486 (6.1); 1.467 (11.7); 1.449 (5.9); 1.427 (1.1); 1.414 (0.7); 1.408 (1.2); 1.390 (0.8); 1.371 (0.3); 1.333 (0.9); 1.305 (0.6); 1.292 (0.7); 1.284 (1.4); 1.278 (0.8); 1.254 (5.6); 1.219 (0.6); 1.174 (1.0); 0.896 (0.4); 0.880 (1.0); 0.862 (0.5); 0.829 (0.4); 0.087 (0.5); 0.078 (0.7); 0.069 (18.1); 0.060 (0.7); 0.050 (0.4); 0.008 (3.1); 0.000 (95.0); −0.009 (3.3); −0.050 (0.5); −0.150 (0.4) |

The following examples illustrate in a non-limiting manner the preparation and efficacy of the compounds of formula (I) according to the invention.

EXAMPLE 1

Preparation of [2-(5,7-difluoro-2,3-dihydro-1H-inden-1-yl)pyrrolidin-1-yl][5-(difluoromethyl)-2-methyl-2H-1,2,3-triazol-4-yl]methanone (Compounds 1.14 and 1.15)

At ambient temperature, a solution of 77 mg (0.40 mmol) of 5-(difluoromethyl)-2-methyl-2H-1,2,3-triazole-4-carbonyl chloride in 1 mL of tetrahydrofurane is added dropwise to a solution of 121 mg (0.36 mmol) of 2-(5,7-difluoro-2,3-dihydro-1H-inden-1-yl)pyrrolidine trifluoroacetate (1:1) and 76 mg (0.75 mmol) of triethylamine in 5 mL of tetrahydrofurane. The reaction mixture is stirred for 1 hour at room temperature. The mixture is poured over a basic alumina cartridge (2 g) and eluted with tetrahydrofurane to give after concentration 147 mg of crude material. The two diastereoisomers of [2-(5,7-difluoro-2,3-dihydro-1H-inden-1-yl)pyrrolidin-1-yl][5-(difluoromethyl)-2-methyl-2H-1,2,3-triazol-4-yl]methanone are separated by preparative HPLC (gradient acetonitrile/water+0.1% of formic acid): diastereoisomer 1: isomer with the highest Rf by TLC on silica gel: 33 mg (22%) (log P=3.63); diastereoisomer 2: isomer with the lowest Rf by TLC on silica gel: 56 mg (38%) (log P=3.41).

GENERAL PREPARATION EXAMPLE 2

Preparation of Amide of Formula (I) on Chemspeed™ Apparatus

In a 13 mL Chemspeed™ vial is distributed 4 mL of a 0.15 M solution of the amine (II) (0.60 mmol) in dichloromethane followed by 0.72 mmol of triethylamine. At a rate of 1 mL/min, 2 mL of a 0.30 M solution of the acyl chloride (III) (0.60 mmol) are added and the mixture is then stirred at room temperature overnight. 1 mL of water is then added and the mixture is poured over a basic alumina cartridge (2 g) and eluted with dichloromethane. The solvents are removed and the crude amide derivative is analyzed by HPLC-MS and NMR. Insufficiently pure compounds are further purified by preparative LC.

GENERAL PREPARATION EXAMPLE 3

Thionation of Amide of Formula (I) on Chemspeed™ Apparatus

In a 13 mL Chemspeed™ vial is weighted 0.27 mmol of phosphorous pentasulfide ($P_2S_5$). 3 mL of a 0.18 M solution of the amide (I) (0.54 mmol) in dioxane is added and the mixture is heated at reflux for two hours. The temperature is then cooled to 80° C. and 2.5 mL of water are added. The mixture is heated at 80° C. for one more hour. 2 mL of water are then added and the reaction mixture is extracted twice by 4 mL of dichloromethane. The organic phase is deposited on a basic alumina cartridge (2 g) and eluted twice by 8 mL of dichloromethane. The solvents are removed and the crude thioamide derivative is analyzed by HPLC-MS and NMR. Insufficiently pure compounds are further purified by preparative LC.

EXAMPLE A

In Vivo Preventive Test on *Alternaria brassicae* (Leaf Spot on Radish)

| Solvent: | 5% | by volume of Dimethyl sulfoxide |
| --- | --- | --- |
|  | 10% | by volume of Acetone |
| Emulsifier: | 1 μL | of Tween ® 80 per mg of active ingredient |

The active ingredients are made soluble and homogenized in a mixture of Dimethyl sulfoxide/Acetone//Tween® 80 and then diluted in water to the desired concentration.

The young plants of radish are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Alternaria brassicae* spores. The contaminated radish plants are incubated for 6 days at 20° C. and at 100% relative humidity.

The test is evaluated 6 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I.25

In this test the following compounds according to the invention showed efficacy between 80% and 89% at a concentration of 500 ppm of active ingredient: I.19

In this test the following compounds according to the invention showed efficacy between 90% and 100% at a concentration of 500 ppm of active ingredient: I.01; I.03; I.08; I.09; I.10; I.11; I.13; I.17; I.18; I.21; I.26; I.27

EXAMPLE B

In Vivo Preventive Test *Botrytis cinerea* (Grey Mould)

| Solvent: | 5% | by volume of Dimethyl sulfoxide |
| --- | --- | --- |
|  | 10% | by volume of Acetone |
| Emulsifier: | 1 μL | of Tween ® 80 per mg of active ingredient |

The active ingredients are made soluble and homogenized in a mixture of Dimethyl sulfoxide/Acetone//Tween® 80 and then diluted in water to the desired concentration.

The young plants of gherkin are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Botrytis cinerea* spores. The contaminated gherkin plants are incubated for 4 to 5 days at 17° C. and at 90% relative humidity.

The test is evaluated 4 to 5 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I.13

In this test the following compounds according to the invention showed efficacy between 80% and 89% at a concentration of 500 ppm of active ingredient: I.03; I.21

In this test the following compounds according to the invention showed efficacy between 90% and 100% at a concentration of 500 ppm of active ingredient: I.10; I.18; I.26; I.34.

EXAMPLE C

In Vivo Preventive Test on *Puccinia recondita* (Brown Rust on Wheat)

| Solvent: | 5% | by volume of Dimethyl sulfoxide |
| --- | --- | --- |
|  | 10% | by volume of Acetone |
| Emulsifier: | 1 µL | of Tween ® 80 per mg of active ingredient |

The active ingredients are made soluble and homogenized in a mixture of Dimethyl sulfoxide/Acetone//Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Puccinia recondita* spores. The contaminated wheat plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I.32; I.34; I.36

In this test the following compounds according to the invention showed efficacy between 80% and 89% at a concentration of 500 ppm of active ingredient: I.01; I.10; I.11; I.17; I.20; I.24; I.27; I.28

In this test the following compounds according to the invention showed efficacy between 90% and 100% at a concentration of 500 ppm of active ingredient: I.02; I.03; I.12; I.13; I.15; I.16; I.18; I.21; I.25; I.26; I.31

Under the same conditions, excellent (at least 90%) to average (at least 60%) protection is observed at a dose of 500 and 100 ppm of active ingredient with compound of example I.31, whereas average protection, is observed at a dose of 500 and 100 ppm of active ingredient with the uncyclized analogue 136 disclosed in patent application WO-2012/052489, as in table C1:

TABLE C1

| Example | dose (ppm) | Efficacy |
| --- | --- | --- |
| I.31 from this patent | 500 | 93 |
|  | 100 | 64 |
| 136 from WO-2012/052489 | 500 | 65 |
|  | 100 | 50 |

Example 136 disclosed in international patent WO-2012/052489, corresponds to [3-(difluoromethyl)-5-fluoro-1-methyl-1H-pyrazol-4-yl][2-(1-phenylpropyl)piperidin-1-yl]methanone.

These results show that the compounds according to the invention have a much better biological activity than the structurally closest compounds claimed in WO-2012/052489.

Under the same conditions, excellent (at least 90%) to high (at least 80%) protection is observed at a dose of 500 and 100 ppm of active ingredient with compound of example I.26, whereas poor (less than 40%) to no protection, is observed in very similar conditions at a dose of 500 and 100 ppm of active ingredient with the uncyclized analogues 11 and 13 disclosed in patent application WO-2011/151369, as in table C2:

TABLE C2

| Example | dose (ppm) | Efficacy |
| --- | --- | --- |
| I.26 from this patent | 500 | 98 |
|  | 100 | 88 |
| 11 from WO-2011/151369 | 500 | 10 [a] |
|  | 100 | 0 [a] |
| 13 from WO-2011/151369 | 500 | 40 [a] |
|  | 100 | 10 [a] |

Note
[a] formulated in DMF with 2% of alkylarylpolyglycolether

Example 11 disclosed in international patent WO-2011/151369 corresponds to N-cyclopropyl-3-(difluoromethyl)-5-fluoro-1-methyl-N-(2-phenylethyl)-1H-pyrazole-4-carboxamide, Example 13 disclosed in international patent WO-2011/151369 corresponds to N-cyclopropyl-3-(difluoromethyl)-5-fluoro-1-methyl-N-(2-phenylpropyl)-1H-pyrazole-4-carboxamide.

These results show that the compounds according to the invention have a much better biological activity than the structurally closest compounds claimed in WO-2011/151369.

EXAMPLE D

In Vivo Preventive Test on *Pyrenophora teres* (Net Blotch on Barley)

| Solvent: | 5% | by volume of Dimethyl sulfoxide |
| --- | --- | --- |
|  | 10% | by volume of Acetone |
| Emulsifier: | 1 µL | of Tween ® 80 per mg of active ingredient |

The active ingredients are made soluble and homogenized in a mixture of Dimethyl sulfoxide/Acetone//Tween® 80 and then diluted in water to the desired concentration.

The young plants of barley are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Pyrenophora teres* spores. The contaminated barley plants are incubated for 48 hours at 20° C. and at 100% relative humidity and then for 12 days at 20° C. and at 70-80% relative humidity.

The test is evaluated 14 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I.09

In this test the following compounds according to the invention showed efficacy between 80% and 89% at a concentration of 500 ppm of active ingredient: I.06; I.14; I.17; I.20; I.27; I.28

In this test the following compounds according to the invention showed efficacy between 90% and 100% at a concentration of 500 ppm of active ingredient: I.01; I.03; I.05; I.07; I.08; I.10; I.11; I.12; I.13; I.15; I.16; I.18; I.21; I.25; I.26; I.29; I.30; I.34.

EXAMPLE E

In Vivo Preventive Test on *Septoria tritici* (Wheat)

| Solvent: | 5% | by volume of Dimethyl sulfoxide |
| | 10% | by volume of Acetone |
| Emulsifier: | 1 μL | of Tween ® 80 per mg of active ingredient |

The active ingredients are made soluble and homogenized in a mixture of Dimethyl sulfoxide/Acetone//Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Septoria tritici* spores. The contaminated wheat plants are incubated for 72 hours at 18° C. and at 100% relative humidity and then for 21 days at 20° C. and at 90% relative humidity.

The test is evaluated 24 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I.32

In this test the following compounds according to the invention showed efficacy between 80% and 89% at a concentration of 500 ppm of active ingredient: I.02; I.06; I.18

In this test the following compounds according to the invention showed efficacy between 90% and 100% at a concentration of 500 ppm of active ingredient: I.01; I.03; I.05; I.07; I.08; I.09; I.10; I.11; I.12; I.13; I.14; I.15; I.16; I.17; I.19; I.20; I.21; I.25; I.26; I.28; I.29; I.30; I.31; I.34; I.35; I.36

EXAMPLE F

In Vivo Preventive Test on *Sphaerotheca fuliginea* (Powdery Mildew on Cucurbits)

| Solvent: | 5% | by volume of Dimethyl sulfoxide |
| | 10% | by volume of Acetone |
| Emulsifier: | 1 μL | of Tween ® 80 per mg of active ingredient |

The active ingredients are made soluble and homogenized in a mixture of Dimethyl sulfoxide/Acetone//Tween® 80 and then diluted in water to the desired concentration.

The young plants of gherkin are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Sphaerotheca fuliginea* spores. The contaminated gherkin plants are incubated for 72 hours at 18° C. and at 100% relative humidity and then for 12 days at 20° C. and at 70-80% relative humidity.

The test is evaluated 15 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I.06; I.20

In this test the following compounds according to the invention showed efficacy between 80% and 89% at a concentration of 500 ppm of active ingredient: I.09; I.25; I.36

In this test the following compounds according to the invention showed efficacy between 90% and 100% at a concentration of 500 ppm of active ingredient: I.01; I.02; I.03; I.08; I.10; I.11; I.12; I.14; I.15; I.17; I.18; I.19; I.21; I.26; I.27; I.30; I.31; I.34.

Under the same conditions, total protection is observed at a dose of 500 and 100 ppm of active ingredient with compound of example I.26, whereas average (at least 60%) to poor (less than 10%) protection, is observed in very similar conditions at a dose of 500 and 100 ppm of active ingredient with the uncyclized analogue 13 disclosed in patent application WO-2011/151369, as in table F1:

TABLE F1

| Example | dose (ppm) | Efficacy |
| --- | --- | --- |
| I.26 from this patent | 500 | 100 |
| | 100 | 100 |
| 13 from WO-2011/151369 | 500 | 63 [a] |
| | 100 | 3 [a] |

Note
[a] formulated in DMF with 2% of alkylarylpolyglycolether

Example 13 disclosed in international patent WO-2011/151369 corresponds to N-cyclopropyl-3-(difluoromethyl)-5-fluoro-1-methyl-N-(2-phenylpropyl)-1H-pyrazole-4-carboxamide.

These results show that the compounds according to the invention have a much better biological activity than the structurally closest compounds claimed in WO-2011/151369.

EXAMPLE G

In Vivo Preventive Test on *Uromyces appendiculatus* (Bean Rust)

| Solvent: | 5% | by volume of Dimethyl sulfoxide |
| | 10% | by volume of Acetone |
| Emulsifier: | 1 μL | of Tween ® 80 per mg of active ingredient |

The active ingredients are made soluble and homogenized in a mixture of Dimethyl sulfoxide/Acetone//Tween® 80 and then diluted in water to the desired concentration.

The young plants of bean are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Uromyces appendiculatus* spores. The contaminated bean plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 80% and 89% at a concentration of 500 ppm of active ingredient: I.01; I.02; I.08; I.12; I.16; I.23

In this test the following compounds according to the invention showed efficacy between 90% and 100% at a concentration of 500 ppm of active ingredient: I.03; I.09; I.10; I.13; I.18; I.19; I.22; I.24; I.25; I.26; I.27

Under the same conditions, total protection is observed at a dose of 500 and 100 ppm of active ingredient with compound of example I.26, whereas good (at least 70%) to no protection, is observed at a dose of 500 and 100 ppm of active ingredient with the uncyclized analogue 53 disclosed in patent application WO-2012/052491, as in table G1:

TABLE G1

| Example | dose (ppm) | Efficacy |
|---|---|---|
| I.26 from this patent | 500 | 100 |
|  | 100 | 100 |
| 53 from WO2012/052491 | 500 | 77 |
|  | 100 | 0 |

Example 53 disclosed in international patent WO2012/052491 corresponds to [3-(difluoromethyl)-5-fluoro-1-methyl-1H-pyrazol-4-yl][2-(1-phenylpropyl)pyrrolidin-1-yl]methanone.

These results show that the compounds according to the invention have a much better biological activity than the structurally closest compounds claimed in WO2012/052491.

Under the same conditions, total to average (at least 50%) protection is observed at a dose of 500 and 100 ppm of active ingredient with compounds of examples 1.26 and 1.27, whereas high (at least 80%) to no protection, is observed at a dose of 500 and 100 ppm of active ingredient with the uncyclized analogue 1.2 disclosed in patent application WO-2010/086311, as in table G2:

TABLE G2

| Example | dose (ppm) | Efficacy |
|---|---|---|
| I.26 from this patent | 500 | 100 |
|  | 100 | 100 |
| I.27 from this patent | 500 | 100 |
|  | 100 | 56 |
| I.2 from WO-2010/086311 | 500 | 88 |
|  | 100 | 0 |

Example I.2 disclosed in international patent WO-2010/086311 corresponds to N-cyclopropyl-5-fluoro-1,3-dimethyl-N-[1-(1,2,3,4-tetrahydronaphthalen-1-yl)ethyl]-1H-pyrazole-4-carboxamide.

These results show that the compounds according to the invention have a much better biological activity than the structurally closest compounds claimed in WO-2010/086311.

The invention claimed is:
1. A compound of formula (I)

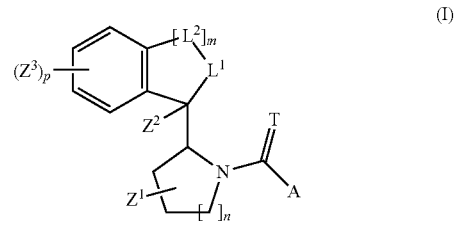

wherein:
A is a carbo-linked, unsaturated or partially saturated, 5-membered heterocyclyl group that can be substituted by up to four groups R that can be the same or different;
T is O or S;
n is 1 or 2;
m is 1, 2 or 3;
p is 1, 2, 3 or 4;
$L^1$ and $L^2$ are independently $CZ^4Z^5$, $NZ^6$, O, S, S(O) or $S(O)_2$;
$Z^1$ is a hydrogen atom, or substituted or non-substituted $C_1$-$C_8$-alkyl;
$Z^2$ is a hydrogen atom, a halogen atom, hydroxyl group, cyano, substituted or non-substituted $C_1$-$C_8$-alkyl, substituted or non-substituted $C_1$-$C_8$-alkoxy, $C_1$-$C_8$-halogenoalkyl comprising up to 9 halogen atoms that can be the same or different, amino or $C_1$-$C_8$-alkylamino;
$Z^3$ is a hydrogen atom; a halogen atom; nitro; cyano; isonitrile; hydroxy; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-halogenoalkyl having 1 to 9 halogen atoms; substituted or non-substituted $C_2$-$C_8$-alkenyl; $C_2$-$C_8$-halogenoalkenyl having 1 to 9 halogen atoms; substituted or non-substituted $C_2$-$C_8$-alkynyl; $C_2$-$C_8$-halogenoalkynyl having 1 to 9 halogen atoms; substituted or non-substituted $C_1$-$C_8$-alkoxy; $C_1$-$C_8$-halogenoalkoxy having 1 to 9 halogen atoms; substituted or non-substituted $C_1$-$C_8$-alkylsulfanyl; $C_1$-$C_8$-halogenoalkylsulfanyl having 1 to 9 halogen atoms; substituted or non-substituted $C_1$-$C_8$-alkylsulfinyl; $C_1$-$C_8$-halogenoalkylsulfinyl having 1 to 9 halogen atoms; substituted or non-substituted $C_1$-$C_8$-alkylsulfonyl; $C_1$-$C_8$-halogenoalkylsulfonyl having 1 to 9 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-halogenoalkenyloxy having 1 to 9 halogen atoms; substituted or non-substituted $C_3$-$C_8$-alkynyloxy; $C_2$-$C_8$-halogenoalkynyloxy having 1 to 9 halogen atoms; substituted or non-substituted $C_3$-$C_7$-cycloalkyl; $C_3$-$C_7$-halogenocycloalkyl having 1 to 9 halogen atoms; substituted or non-substituted $C_4$-$C_7$-cycloalkenyl; $C_4$-$C_7$-halogenocycloalkenyl having 1 to 9 halogen atoms; substituted or non-substituted ($C_3$-$C_7$-cycloalkyl)-$C_1$-$C_8$-alkyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted $C_1$-$C_8$-alkylcarbonyl; $C_1$-$C_8$-halogenoalkylcarbonyl having 1 to 9 halogen atoms; substituted or non-substituted $C_1$-$C_8$-alkylcarbonyloxy; $C_1$-$C_8$-halogenoalkylcarbonyloxy having 1 to 9 halogen atoms; substituted or non-substituted $C_1$-$C_8$-alkylcarbonylamino; $C_1$-$C_8$-halogenoalkylcarbonylamino having 1 to 9 halogen atoms; substituted or non-substituted $C_1$-$C_8$-alkoxycarbonyl; $C_1$-$C_8$-halogenoalkoxycarbonyl having 1 to 9 halogen atoms; substituted or non-substituted $C_1$-$C_8$-alkyloxycarbonyloxy; $C_1$-$C_8$-halogenoalkoxycarbonyloxy having 1 to 9 halogen atoms; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl that can be substituted by up to 6 groups Q which can be the same or different; aryl-$C_1$-$C_8$-alkyl that can be substituted by up to 6 groups Q which can be the same or different; aryl-$C_2$-$C_8$-alkenyl that can be substituted by up to 6 groups Q which can be the same or different; aryl-$C_2$-$C_8$-alkynyl that can be substituted by up to 6 groups Q which can be the same or different; aryloxy that can be substituted by up to 6 groups Q which can be the same or different; arylsulfanyl that can be substituted by up to 6 groups Q which can be the same or different; or arylamino that can be substituted by up to 6 groups Q which can be the same or different; aryl-$C_1$-$C_8$-alkyloxy that can be substituted by up to 6 groups Q which can be the same or different; aryl-$C_1$-$C_8$-alkylsulfanyl that can be substituted by up to 6 groups Q which can be the same or different; aryl-$C_1$-$C_8$-alkylamino that can be substituted by up to 6 groups Q which can be the same or different; pyridinyl which can be substituted by up to 4 groups Q; pyridinyloxy which can be substituted by up to 4 groups Q;

$Z^4$ and $Z^5$ are independently a hydrogen atom, a halogen atom, cyano, nitro, substituted or non-substituted $C_1$-$C_8$-alkyl, $C_1$-$C_8$-halogenoalkyl comprising up to 9 halogen atoms that can be the same or different, substituted or non-substituted $C_1$-$C_8$-alkoxy, $C_1$-$C_8$-halogenoalkoxy comprising up to 9 halogen atoms that can be the same or different, substituted or non-substituted $C_1$-$C_8$-alkoxy-$C_1$-$C_8$-alkyl, substituted or non-substituted $C_2$-$C_8$-alkenyl, $C_2$-$C_8$-halogenoalkenyl comprising up to 9 halogen atoms that can be the same or different, substituted or non-substituted $C_2$-$C_8$-alkynyl, $C_2$-$C_8$-halogenoalkynyl comprising up to 9 halogen atoms that can be the same or different, substituted or non-substituted $C_3$-$C_7$-cycloalkyl, substituted or non-substituted $C_3$-$C_7$-cycloalkyl-$C_1$-$C_8$-alkyl, $C_3$-$C_7$-halogenocycloalkyl comprising up to 9 halogen atoms that can be the same or different, formyl, substituted or non-substituted $C_1$-$C_8$-alkylcarbonyl, $C_1$-$C_8$-halogenoalkylcarbonyl comprising up to 9 halogen atoms that can be the same or different, substituted or non-substituted $C_1$-$C_8$-alkylsulfanyl, $C_1$-$C_8$-halogenoalkylsulfanyl comprising up to 9 halogen atoms that can be the same or different, substituted or non-substituted $C_1$-$C_8$-alkylsulfinyl, $C_1$-$C_8$-halogenoalkylsulfinyl comprising up to 9 halogen atoms that can be the same or different, substituted or non-substituted $C_1$-$C_8$-alkylsulfonyl, or $C_1$-$C_8$-halogenoalkylsulfonyl comprising up to 9 halogen atoms that can be the same or different;

$Z^6$ is a hydrogen atom, substituted or non-substituted $C_1$-$C_8$-alkyl, $C_1$-$C_8$-halogenoalkyl comprising up to 9 halogen atoms that can be the same or different, substituted or non-substituted $C_1$-$C_8$-alkoxy-$C_1$-$C_8$-alkyl, substituted or non-substituted $C_2$-$C_8$-alkenyl, $C_2$-$C_8$-halogenoalkenyl comprising up to 9 halogen atoms that can be the same or different, substituted or non-substituted $C_2$-$C_8$-alkynyl, $C_3$-$C_8$-halogenoalkynyl comprising up to 9 halogen atoms that can be the same or different, substituted or non-substituted $C_3$-$C_7$-cycloalkyl, substituted or non-substituted $C_3$-$C_7$-cycloalkyl-$C_1$-$C_8$-alkyl, $C_3$-$C_7$-halogenocycloalkyl comprising up to 9 halogen atoms that can be the same or different, formyl, substituted or non-substituted $C_1$-$C_8$-alkylcarbonyl, $C_1$-$C_8$-halogenoalkylcarbonyl comprising up to 9 halogen atoms that can be the same or different, substituted or non-substituted $C_1$-$C_8$-alkoxycarbonyl, substituted or non-substituted $C_1$-$C_8$-alkylsulfonyl, $C_1$-$C_8$-halogenoalkylsulfonyl comprising up to 9 halogen atoms that can be the same or different, phenylsulfonyl can be substituted by up to 5 groups Q that can be the same or different, or benzyl that can be substituted by up to 5 groups Q that can be the same or different;

each Q is independently a halogen atom, cyano, nitro, substituted or non-substituted $C_1$-$C_8$-alkyl, $C_1$-$C_8$-halogenoalkyl comprising up to 9 halogen atoms that can be the same or different, substituted or non-substituted $C_1$-$C_8$-alkoxy, $C_1$-$C_8$-halogenoalkoxy comprising up to 9 halogen atoms that can be the same or different, substituted or non-substituted $C_1$-$C_8$-alkylsulfanyl, $C_1$-$C_8$-halogenoalkylsulfanyl comprising up to 9 halogen atoms that can be the same or different, substituted or non-substituted tri ($C_1$-$C_8$)alkylsilyl, substituted or non-substituted tri ($C_1$-$C_8$)alkylsilyl-$C_1$-$C_8$-alkyl, substituted or non-substituted ($C_1$-$C_8$-alkoxyimino)-$C_1$-$C_8$-alkyl, or substituted or non-substituted (benzyloxyimino)-$C_1$-$C_8$-alkyl; and each R is independently hydrogen atom; halogen atom; nitro; cyano; hydroxy; amino; sulfanyl; pentafluoro-$\lambda^6$-sulfanyl; substituted or non-substituted ($C_1$-$C_8$-alkoxyimino)-$C_1$-$C_8$-alkyl; substituted or non-substituted (benzyloxyimino)-$C_1$-$C_8$-alkyl; substituted or non-substituted $C_1$-$C_8$-alkyl; $C_1$-$C_8$-halogenoalkyl having 1 to 9 halogen atoms; substituted or non-substituted $C_2$-$C_8$-alkenyl; $C_2$-$C_8$-halogenoalkenyl having 1 to 9 halogen atoms; substituted or non-substituted $C_2$-$C_8$-alkynyl; $C_2$-$C_8$-halogenoalkynyl having 1 to 9 halogen atoms; substituted or non-substituted $C_1$-$C_8$-alkoxy; $C_1$-$C_8$-halogenoalkoxy having 1 to 9 halogen atoms; substituted or non-substituted $C_1$-$C_8$-alkylsulfanyl; $C_1$-$C_8$-halogenoalkylsulfanyl having 1 to 9 halogen atoms; substituted or non-substituted $C_1$-$C_8$-alkylsulfinyl; $C_1$-$C_8$-halogenoalkylsulfinyl having 1 to 9 halogen atoms; substituted or non-substituted $C_1$-$C_8$-alkylsulfonyl; $C_1$-$C_8$-halogenoalkylsulfonyl having 1 to 9 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; substituted or non-substituted $C_3$-$C_8$-alkynyloxy; substituted or non-substituted $C_3$-$C_7$-cycloalkyl; $C_3$-$C_7$-halogenocycloalkyl having 1 to 9 halogen atoms; substituted or non-substituted tri($C_1$-$C_8$)alkylsilyl; substituted or non-substituted $C_1$-$C_8$-alkylcarbonyl; $C_1$-$C_8$-halogenoalkylcarbonyl having 1 to 9 halogen atoms; substituted or non-substituted $C_1$-$C_8$-alkoxycarbonyl; $C_1$-$C_8$-halogenoalkoxycarbonyl having 1 to 9 halogen atoms; substituted or non-substituted $C_1$-$C_8$-alkylcarbamoyl; substituted or non-substituted di-$C_1$-$C_8$-alkylcarbamoyl; phenoxy; phenylsulfanyl; phenylamino; benzyloxy; benzylsulfanyl; or benzylamino;
or a salt, an N-oxide, a metal complex, a metalloid complex, an optically active isomer, or a geometric isomer thereof.

2. The compound according to claim 1, or a salt, an N-oxide, a metal complex, a metalloid complex, an optically active isomer, or a geometric isomer thereof, wherein A is selected from the group consisting of:
a heterocycle of formula ($A^1$)

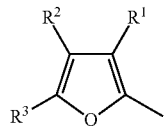

wherein:
$R^1$, $R^2$, and $R^3$ are independently a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or $C_1$-$C_5$-halogenoalkoxy comprising up to 9 halogen atoms that can be the same or different;
a heterocycle of formula ($A^2$)

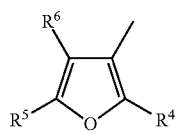

wherein:
$R^4$, $R^5$, and $R^6$ are independently a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or $C_1$-$C_5$-halogenoalkoxy comprising up to 9 halogen atoms that can be the same or different;
a heterocycle of formula ($A^3$)

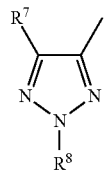

wherein:
$R^7$ is a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or $C_1$-$C_5$-halogenoalkoxy comprising up to 9 halogen atoms that can be the same or different;
$R^8$ is a hydrogen atom or a substituted or non-substituted $C_1$-$C_5$-alkyl;
a heterocycle of formula ($A^4$)

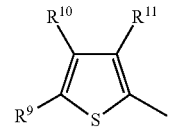

wherein:
$R^9$, $R^{10}$, and $R^{11}$ are independently a hydrogen atom; a halogen atom; substituted or non-substituted $C_1$-$C_5$-alkyl; amino; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different or $C_1$-$C_5$-halogenoalkoxy comprising up to 9 halogen atoms that can be the same or different;
a heterocycle of formula ($A^5$)

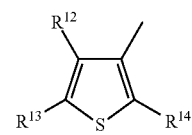

wherein:
$R^{12}$ and $R^{13}$ are independently a hydrogen atom; a halogen atom; substituted or non-substituted $C_1$-$C_5$-alkyl; substituted or non-substituted $C_1$-$C_5$-alkoxy; amino; $C_1$-$C_5$-halogenoalkyl comprising up to 9 halogen atoms that can be the same or different or $C_1$-$C_5$-halogenoalkoxy comprising up to 9 halogen atoms that can be the same or different;
$R^{14}$ is a hydrogen atom; a halogen atom; substituted or non-substituted $C_1$-$C_5$-alkyl; substituted or non-substituted $C_1$-$C_5$-alkoxy; amino; $C_1$-$C_5$-halogenoalkyl comprising up to 9 halogen atoms that can be the same or different or $C_1$-$C_5$-halogenoalkoxy comprising up to 9 halogen atoms that can be the same or different;

a heterocycle of formula ($A^6$)

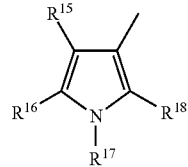

($A^6$)

wherein:

$R^{15}$ is a hydrogen atom; a halogen atom; a cyano; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{16}$ and $R^{18}$ are independently a hydrogen atom; a halogen atom; substituted or non-substituted $C_1$-$C_5$-alkoxycarbonyl; substituted or non-substituted $C_1$-$C_5$-alkyl; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{17}$ is a hydrogen atom or substituted or non-substituted $C_1$-$C_5$-alkyl;

a heterocycle of formula ($A^7$)

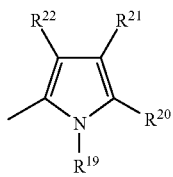

($A^7$)

wherein:

$R^{19}$ is a hydrogen atom or a $C_1$-$C_5$-alkyl $R^{20}$, $R^{21}$, and $R^{22}$ are independently a hydrogen atom; a halogen atom; substituted or non-substituted $C_1$-$C_5$-alkyl or $C_1$-$C_5$-halogenoalkyl comprising up to 9 halogen atoms that can be the same or different;

a heterocycle of formula ($A^8$)

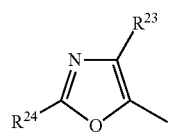

($A^8$)

wherein:

$R^{23}$ is a hydrogen atom; a halogen atom; substituted or non-substituted $C_1$-$C_5$-alkyl or $C_1$-$C_5$-halogenoalkyl comprising up to 9 halogen atoms that can be the same or different;

$R^{24}$ is a hydrogen atom or substituted or non-substituted $C_1$-$C_5$-alkyl or $C_1$-$C_5$-halogenoalkyl comprising up to 9 halogen atoms that can be the same or different;

a heterocycle of formula ($A^9$)

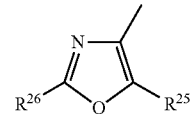

($A^9$)

wherein:

$R^{25}$ is a hydrogen atom; a halogen atom; substituted or non-substituted $C_1$-$C_5$-alkyl or $C_1$-$C_5$-halogenoalkyl comprising up to 9 halogen atoms that can be the same or different;

$R^{26}$ is a hydrogen atom; substituted or non-substituted $C_1$-$C_5$-alkyl or $C_1$-$C_5$-halogenoalkyl comprising up to 9 halogen atoms that can be the same or different;

a heterocycle of formula ($A^{10}$)

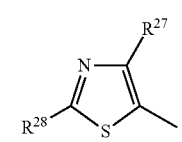

($A^{10}$)

wherein:

$R^{27}$ is a hydrogen atom; a halogen atom; substituted or non-substituted $C_1$-$C_5$-alkyl or $C_1$-$C_5$-halogenoalkyl comprising up to 9 halogen atoms that can be the same or different;

$R^{28}$ is a hydrogen atom; a halogen atom; substituted or non-substituted $C_1$-$C_5$-alkyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or substituted or non-substituted di($C_1$-$C_5$-alkyl)amino;

a heterocycle of formula ($A^{11}$)

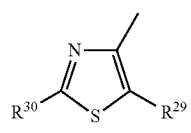

($A^{11}$)

wherein:

$R^{29}$ is a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{30}$ is a hydrogen atom; substituted or non-substituted $C_1$-$C_5$-alkyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or substituted or non-substituted di($C_1$-$C_5$-alkyl)amino;

a heterocycle of formula (A$^{12}$)

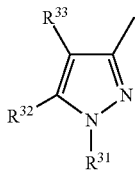

(A$^{12}$)

wherein:
R$^{31}$ is a hydrogen atom or a substituted or non-substituted C$_1$-C$_5$-alkyl
R$^{32}$ is a hydrogen atom; a halogen atom; substituted or non-substituted C$_1$-C$_5$-alkyl or C$_1$-C$_5$-halogenoalkyl comprising up to 9 halogen atoms that can be the same or different;
R$^{33}$ is a hydrogen atom; a halogen atom; a nitro; substituted or non-substituted C$_1$-C$_5$-alkyl; substituted or non-substituted C$_1$-C$_5$-alkoxy; C$_1$-C$_5$-halogenoalkoxy comprising up to 9 halogen atoms that can be the same or different or C$_1$-C$_5$-halogenoalkyl comprising up to 9 halogen atoms that can be the same or different;
a heterocycle of formula (A$^{13}$)

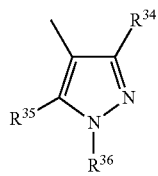

(A$^{13}$)

wherein:
R$^{34}$ is a hydrogen atom; a halogen atom; substituted or non-substituted C$_1$-C$_5$-alkyl; substituted or non-substituted C$_3$-C$_5$-cycloalkyl; C$_1$-C$_5$-halogenoalkyl comprising up to 9 halogen atoms that can be the same or different; substituted or non-substituted C$_1$-C$_5$-alkoxy; substituted or non-substituted C$_2$-C$_5$-alkynyloxy or C$_1$-C$_5$-halogenoalkoxy comprising up to 9 halogen atoms that can be the same or different;
R$^{35}$ is a hydrogen atom; a halogen atom; substituted or non-substituted C$_1$-C$_5$-alkyl; a cyano; substituted or non-substituted C$_1$-C$_5$-alkoxy; substituted or non-substituted C$_1$-C$_5$-alkylsulfanyl; C$_1$-C$_5$-halogenoalkyl comprising up to 9 halogen atoms that can be the same or different; C$_1$-C$_5$-halogenoalkoxy comprising up to 9 halogen atoms that can be the same or different; amino; substituted or non-substituted C$_1$-C$_5$-alkylamino or substituted or non-substituted di(C$_1$-C$_5$-alkyl)amino;
R$^{36}$ is a hydrogen atom or non-substituted C$_1$-C$_5$-alkyl;
a heterocycle of formula (A$^{14}$)

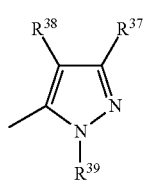

(A$^{14}$)

wherein:
R$^{37}$ and R$^{38}$ are independently a hydrogen atom; a halogen atom; substituted or non-substituted C$_1$-C$_5$-alkyl; C$_1$-C$_5$-halogenoalkyl comprising up to 9 halogen atoms that can be the same or different; substituted or non-substituted C$_1$-C$_5$-alkoxy or a substituted or non-substituted C$_1$-C$_5$-alkylsulfanyl;
R$^{39}$ is a hydrogen atom or substituted or non-substituted C$_1$-C$_5$-alkyl;
a heterocycle of formula (A$^{15}$)

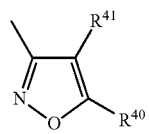

(A$^{15}$)

wherein:
R$^{40}$ and R$^{41}$ are independently a hydrogen atom; a halogen atom; substituted or non-substituted C$_1$-C$_5$-alkyl or C$_1$-C$_5$-halogenoalkyl comprising up to 9 halogen atoms that can be the same or different;
a heterocycle of formula (A$^{16}$)

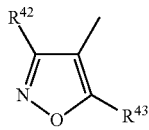

(A$^{16}$)

wherein:
R$^{42}$ and R$^{43}$ are independently a hydrogen atom; a halogen atom; substituted or non-substituted C$_1$-C$_5$-alkyl; C$_1$-C$_5$-halogenoalkyl comprising up to 9 halogen atoms that can be the same or different or amino;
a heterocycle of formula (A$^{17}$)

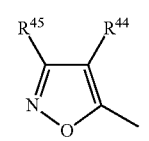

(A$^{17}$)

wherein:
R$^{44}$ and R$^{45}$ are independently a hydrogen atom; a halogen atom; substituted or non-substituted C$_1$-C$_5$-alkyl or C$_1$-C$_5$-halogenoalkyl comprising up to 9 halogen atoms that can be the same or different;
a heterocycle of formula (A$^{18}$)

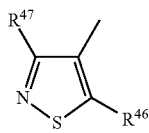

(A$^{18}$)

wherein:

$R^{47}$ is a hydrogen atom; a halogen atom; substituted or non-substituted $C_1$-$C_5$-alkyl or $C_1$-$C_5$-halogenoalkyl comprising up to 9 halogen atoms that can be the same or different;

$R^{46}$ is a hydrogen atom; a halogen atom; substituted or non-substituted $C_1$-$C_5$-alkyl; $C_1$-$C_5$-halogenoalkyl comprising up to 9 halogen atoms that can be the same or different or substituted or non-substituted $C_1$-$C_5$-alkylsulfanyl;

a heterocycle of formula ($A^{19}$)

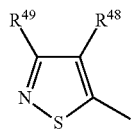

wherein:

$R^{48}$ and $R^{49}$ are independently a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

a heterocycle of formula ($A^{20}$)

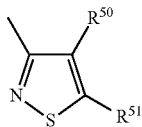

wherein:

$R^{50}$ and $R^{51}$ are independently a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

a heterocycle of formula ($A^{21}$)

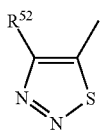

wherein:

$R^{52}$ is a hydrogen atom; a halogen atom; substituted or non-substituted $C_1$-$C_5$-alkyl or $C_1$-$C_5$-halogenoalkyl comprising up to 9 halogen atoms that can be the same or different;

a heterocycle of formula ($A^{22}$)

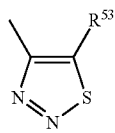

wherein:

$R^{53}$ is a hydrogen atom; a halogen atom; substituted or non-substituted $C_1$-$C_5$-alkyl or $C_1$-$C_5$-halogenoalkyl comprising up to 9 halogen atoms that can be the same or different;

a heterocycle of formula ($A^{23}$)

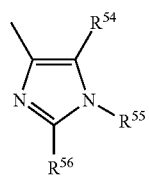

wherein:

$R^{54}$ and $R^{56}$ are independently a hydrogen atom; a halogen atom; substituted or non-substituted $C_1$-$C_5$-alkyl or $C_1$-$C_5$-halogenoalkyl comprising up to 9 halogen atoms that can be the same or different;

$R^{55}$ is a hydrogen atom or substituted or non-substituted $C_1$-$C_5$-alkyl;

a heterocycle of formula ($A^{24}$)

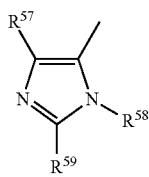

wherein:

$R^{57}$ and $R^{59}$ are independently a hydrogen atom; a halogen atom; substituted or non-substituted $C_1$-$C_5$-alkyl or $C_1$-$C_5$-halogenoalkyl comprising up to 9 halogen atoms that can be the same or different;

$R^{58}$ is a hydrogen atom or substituted or non-substituted $C_1$-$C_5$-alkyl;

a heterocycle of formula ($A^{25}$)

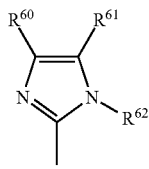

wherein:

$R^{60}$ and $R^{61}$ are independently a hydrogen atom; a halogen atom; substituted or non-substituted $C_1$-$C_5$-alkyl or $C_1$-$C_5$-halogenoalkyl comprising up to 9 halogen atoms that can be the same or different;

$R^{62}$ is a hydrogen atom or substituted or non-substituted $C_1$-$C_5$-alkyl; and a heterocycle of formula ($A^{26}$)

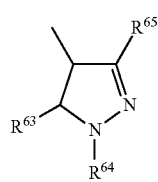

wherein:
$R^{65}$ is a hydrogen atom; a halogen atom; substituted or non-substituted $C_1$-$C_5$-alkyl; substituted or non-substituted $C_3$-$C_5$-cycloalkyl; $C_1$-$C_5$-halogenoalkyl comprising up to 9 halogen atoms that can be the same or different; substituted or non-substituted $C_1$-$C_5$-alkoxy; substituted or non-substituted $C_2$-$C_5$-alkynyloxy or $C_1$-$C_5$-halogenoalkoxy comprising up to 9 halogen atoms that can be the same or different;
$R^{63}$ is a hydrogen atom; a halogen atom; substituted or non-substituted $C_1$-$C_5$-alkyl; a cyano; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or di($C_1$-$C_5$-alkyl)amino;
$R^{64}$ is a hydrogen atom or substituted or non-substituted $C_1$-$C_5$-alkyl.

3. The compound according to claim 2, or a salt, an N-oxide, a metal complex, a metalloid complex, an optically active isomer, or a geometric isomer thereof, wherein A is selected from the group consisting of $A^2$; $A^5$; $A^6$; $A^{10}$ and $A^{13}$.

4. The compound according to claim 3, or a salt, an N-oxide, a metal complex, a metalloid complex, an optically active isomer, or a geometric isomer thereof, wherein
A is $A^{13}$, wherein
$R^{34}$ is a substituted or non-substituted $C_1$-$C_5$-alkyl, $C_1$-$C_5$-halogenoalkyl comprising up to 9 halogen atoms that can be the same or different; substituted or non-substituted $C_1$-$C_5$-alkoxy;
$R^{35}$ is a hydrogen atom or a halogen atom, and
$R^{36}$ is a substituted or non-substituted $C_1$-$C_5$-alkyl.

5. The compound according to claim 1, or a salt, an N-oxide, a metal complex, a metalloid complex, an optically active isomer, or a geometric isomer thereof, wherein
A is $A^{13}$, wherein
$R^{34}$ is $C_1$-$C_5$-alkyl, $C_1$-$C_5$-halogenoalkyl comprising up to 3 halogen atoms that can be the same or different;
$R^{35}$ is a hydrogen atom; a chlorine atom; or a fluorine atom, and
$R^{36}$ is a methyl.

6. The compound according to claim 1, or a salt, an N-oxide, a metal complex, a metalloid complex, an optically active isomer, or a geometric isomer thereof, wherein T is O.

7. The compound according to claim 1, or a salt, an N-oxide, a metal complex, a metalloid complex, an optically active isomer, or a geometric isomer thereof, wherein m is 1 or 2.

8. The compound according to claim 1, or a salt, an N-oxide, a metal complex, a metalloid complex, an optically active isomer, or a geometric isomer thereof, wherein $L^1$ is $CZ^4Z^5$.

9. The compound according to claim 1, or a salt, an N-oxide, a metal complex, a metalloid complex, an optically active isomer, or a geometric isomer thereof, wherein $L^2$ is $CZ^4Z^5$, O or S.

10. The compound according to claim 9, or a salt, an N-oxide, a metal complex, a metalloid complex, an optically active isomer, or a geometric isomer thereof, wherein $L^2$ is $CZ^4Z^5$.

11. The compound according to claim 1, or a salt, an N-oxide, a metal complex, a metalloid complex, an optically active isomer, or a geometric isomer thereof, wherein $L^2$ is O.

12. The compound according to claim 1, or a salt, an N-oxide, a metal complex, a metalloid complex, an optically active isomer, or a geometric isomer thereof, wherein $Z^1$ or $Z^2$ or both are a hydrogen atom.

13. The compound according to claim 1, or a salt, an N-oxide, a metal complex, a metalloid complex, an optically active isomer, or a geometric isomer thereof, wherein $Z^3$ is a hydrogen atom, a halogen atom, $C_1$-$C_8$-alkyl, $C_1$-$C_8$-halogenoalkyl comprising up to 9 halogen atoms that can be the same or different, $C_1$-$C_8$-alkoxy or $C_1$-$C_8$-halogenoalkoxy comprising up to 9 halogen atoms that can be the same or different.

14. The compound according to claim 1, or a salt, an N-oxide, a metal complex, a metalloid complex, an optically active isomer, or a geometric isomer thereof, wherein $Z^4$ and $Z^5$ are independently a hydrogen atom or $C_1$-$C_8$-alkyl.

15. The compound according to claim 14, or a salt, an N-oxide, a metal complex, a metalloid complex, an optically active isomer, or a geometric isomer thereof, wherein $Z^4$ and $Z^5$ both are a hydrogen atom.

16. A fungicide composition comprising, as an active ingredient, an effective amount of a compound of formula (I) according to claim 1, or a salt, an N-oxide, a metal complex, a metalloid complex, an optically active isomer, or a geometric isomer thereof, and an agriculturally acceptable support, carrier or filler.

17. A fungicide composition according to claim 16, comprising at least one further active ingredient selected from the group consisting of insecticides, attractants, sterilants, bactericides, acaricides, nematicides, fungicides, growth regulators, herbicides, fertilizers, safeners, biologicals and semiochemicals.

18. A method for controlling phytopathogenic fungi of crops, comprising applying an agronomically effective and substantially non-phytotoxic quantity of a compound according to claim 1, or a salt, an N-oxide, a metal complex, a metalloid complex, an optically active isomer, or a geometric isomer thereof, to the soil where plants grow or are capable of growing, to the leaves and/or the fruit of plants or to the seeds of plants.

19. A process for producing compositions for controlling phytopathogenic harmful fungi, comprising mixing a compound of formula (I) according to claim 1, or a salt, an N-oxide, a metal complex, a metalloid complex, an optically active isomer, or a geometric isomer thereof, with extenders and/or surfactants.

20. A method for controlling phytopathogenic fungi of crops, comprising applying an agronomically effective and substantially non-phytotoxic quantity of a compound according to claim 1, or a salt, an N-oxide, a metal complex, a metalloid complex, an optically active isomer, or a geometric isomer thereof, to plants, seeds, transgenic plants or transgenic seeds.

21. A method for controlling phytopathogenic fungi of crops, comprising applying an agronomically effective and substantially non-phytotoxic quantity of a composition according to claim 16, to the soil where plants grow or are capable of growing, to the leaves and/or the fruit of plants or to the seeds of plants.

\* \* \* \* \*